US007253179B2

(12) United States Patent
Chen et al.

(10) Patent No.: US 7,253,179 B2
(45) Date of Patent: Aug. 7, 2007

(54) FUSED HETEROCYCLIC COMPOUNDS

(75) Inventors: Xi Chen, Palo Alto, CA (US); Xiaoqi Chen, San Mateo, CA (US); Pingchen Fan, Fremont, CA (US); Juan Jaen, Burlingame, CA (US); Leping Li, Burlingame, CA (US); Jeffrey Thomas Mihalic, San Francisco, CA (US)

(73) Assignee: Amgen Inc., Thousand Oaks, CA (US)

( * ) Notice: Subject to any disclaimer, the term of this patent is extended or adjusted under 35 U.S.C. 154(b) by 469 days.

(21) Appl. No.: 10/705,173

(22) Filed: Nov. 6, 2003

(65) Prior Publication Data

US 2004/0147538 A1 Jul. 29, 2004

Related U.S. Application Data

(60) Provisional application No. 60/424,456, filed on Nov. 6, 2002.

(51) Int. Cl.
*A61K 31/4745* (2006.01)
*C07D 471/02* (2006.01)

(52) U.S. Cl. ........................................ 514/285; 546/70
(58) Field of Classification Search ................ 514/285; 546/70
See application file for complete search history.

(56) References Cited

U.S. PATENT DOCUMENTS

| 4,115,538 | A | 9/1978 | Satoh et al. |
|---|---|---|---|
| 5,049,655 | A | 9/1991 | Vaughan et al. |
| 5,272,146 | A | 12/1993 | Haugwitz et al. |
| 5,436,128 | A | 7/1995 | Harpold et al. |
| 5,441,956 | A | 8/1995 | Vecchietti et al. |
| 5,449,766 | A | 9/1995 | Vaughan et al. |
| 5,457,208 | A | 10/1995 | Portoghese et al. |
| 5,530,095 | A | 6/1996 | Vaughan et al. |
| 5,849,708 | A | 12/1998 | Maratos-Flier |
| 6,033,872 | A | 3/2000 | Bergsma et al. |
| 6,858,619 | B2* | 2/2005 | Chen et al. ............... 514/285 |
| 2003/0023085 | A1 | 1/2003 | Chen et al. |
| 2003/0176694 | A1 | 9/2003 | Chen et al. |
| 2003/0199549 | A1 | 10/2003 | Burnett et al. |

FOREIGN PATENT DOCUMENTS

| EP | 0 257 701 | 3/1988 |
|---|---|---|
| EP | 02 73 4135 | 4/2005 |
| JP | 4-368384 | 12/1992 |
| JP | 2001226269 | 8/2001 |
| WO | WO91/07966 | 6/1991 |
| WO | WO94/07896 | 4/1994 |
| WO | WO95/13071 | 5/1995 |
| WO | WO96/23793 | 8/1996 |
| WO | WO98/31684 | 7/1998 |
| WO | WO99/28492 | 6/1999 |
| WO | WO99/64002 | 12/1999 |
| WO | WO00/15793 | 3/2000 |
| WO | WO00/21577 | 4/2000 |
| WO | WO00/22129 | 4/2000 |
| WO | WO00/39279 | 7/2000 |
| WO | WO00/40725 | 7/2000 |
| WO | WO00/49046 | 8/2000 |
| WO | WO00/49170 | 8/2000 |
| WO | WO00/70347 | 11/2000 |
| WO | WO00/75166 | 12/2000 |
| WO | WO01/05947 | 1/2001 |
| WO | WO01/07606 | 2/2001 |
| WO | WO01/07611 | 2/2001 |
| WO | WO01/21169 | 3/2001 |
| WO | WO01/21577 | 3/2001 |
| WO | WO01/36479 | 5/2001 |
| WO | WO01/68706 | 9/2001 |
| WO | WO01/70975 | 9/2001 |
| WO | WO01/87834 | 11/2001 |
| WO | WO02/02744 | 1/2002 |
| WO | WO02/03070 | 1/2002 |
| WO | WO02/04433 | 1/2002 |
| WO | WO02/06245 | 1/2002 |
| WO | WO02/32897 | 4/2002 |
| WO | WO02/051809 | 7/2002 |
| WO | WO02/057233 | 7/2002 |
| WO | WO02/076929 | 10/2002 |
| WO | WO02/076947 | 10/2002 |
| WO | WO02/083134 | 10/2002 |
| WO | WO02/094799 | 11/2002 |
| WO | WO02089729 | 11/2002 |
| WO | WO03/060475 | 7/2003 |

(Continued)

FOREIGN PATENT DOCUMENTS

WO PCT/US03/35543 4/2004

OTHER PUBLICATIONS

Berridge, et al. "Inositol Triphosphate, a Novel Second Messenger In Cellular Signal Transduction", Nature (1984) 312:315-321.
Chambers, et al. "Melanin-concentrating hormone is the cognate ligand for the orphan G-protein-coupled receptor SLC-1", Nature (1999) 400: 261-265.
Felley-Bosco, et al. "Constitutive Expression of Inducible Nitric Oxide Synthase in Human Brochial Epithelial Cells Induces c-fos and Stimulates the cGMP Pathway", Am J. Respir Cell. Mol. Biol. (1994) 11: 159-164.
Gonzalez, et al., "alpha-Melanocyte-stimulating hormone (alpha-MSH) and melanin-concentrating hormone (MCH) modify monoaminergic levels in the preoptic area of the rat" *Peptides* (1997) 18:387-392.

(Continued)

*Primary Examiner*—Charanjit S. Aulakh
(74) *Attorney, Agent, or Firm*—Jones Day

(57) ABSTRACT

Compounds, compositions and methods are provided that are useful in the treatment and/or prevention of a condition or disorder mediated by a G-protein coupled receptor. In particular, the compounds of the invention are useful in the treatment and/or prevention of eating disorders, obesity, anxiety disorders and mood disorders.

35 Claims, 1 Drawing Sheet

OTHER PUBLICATIONS

Gonzalez, et al., "Behavioral Effects of α-MSH and MCH After Central Administration in the Female Rat" *Peptides* (1996) 17(1):171-177.

Monzon, et al., "Response to Novelty After I.C.V. Injection of Melanin-Concentrating Hormone (MCH) in Rats" *Physiol. Behav.* (1999) 67(5):813-817.

Offerman, et al. "$G\alpha_{15}$ and $G\alpha_{16}$ Couple A Wide Variety of Receptors to Phospholipase C", The J. of Biological chemistry (1995), 270(25) pp. 15175-15180.

Rai, et al., "Synthesis, P{hysicochemical Properties, and Evaluation of N-Substituted-2-Alkyl-3-Hydroxy-4(1H)-Pyridones" J.. Med. Chem. (1998) 41:3347-3359.

Saito, et al. "Molecular characterization of the melanin-concentrating-hormone receptor", *Nature*(1999) 400: 265-269.

Saito, et al., "Melanin-concentrating hormone receptor: an orphan receptor fits the key" *Trends Endocrinol. Metab.* (2000) 11(8):299-303.

Seyferth, et al., "Some Reactions of Dimethylphosphono-Substituted Diazoalkanes. $(MeO)_2P(O)CR$ Transfer to Olefins and 1,3-Dipolar Additions of $(MeO)_2P(O)C(N_2)R^1$ ", J. Org. Chem. (1971) 36(10): 1379-1386.

Shimada, et al., "Mice Lacking melanin-concentrating hormone are Hypophagic and Lean", *Nature* (1998) 396: 670-674.

Wilkie, et al., "Characterization of G-Protein α Subunits in the $G_q$ Class: Expression in Murine Tissues and In Stromal and Hematopoietic Cell Lines", Proc. Natl. Acad. Sci. USA (1991) 88: pp. 10049-10053.

Aceto, MD et al., "Dependence studies of new compounds in the Rhesus monkey, rat and mouse", (1997) Department of Pharmacology and Toxicology, Medical College of Virginia Commonwealth University, pp. 363-407.

Bergman et al., 1980 ACTA Chemica Scandinavica, Series B; Organic Chemistry and Biochemistry B34(10):763-66.

Blechert, S. et al., "Domino reactions—New concepts in the synthesis of indole alkaloids and other polycyclic indole derivatives", (1995) Insitut Für Organische Chemie, Sekr. C3, Technische Universität Berlin, Straβe des 17 Juni 135, D-10623 Berlin, Germany pp. 592-604.

Boutin et al., (2002) "Melanin-Concentrating Hormone and its Receptors: State of the Art," Can, J. of Physio. and Pharmacol. 80: 388-395.

Chambers et al., "Melanin-concentrating hormone is the cognate ligand for the orphan G-protein-coupled receptor SLC-1" *Nature*, (1999) 400:261-65.

Fujii, H. et al., "A novel abnormal rearrangement in the fishcer indole synthesis", (1997) *Heterocycles* 45:2109-2112.

Gouyette, A. et al., "Synthesis, DNA intercalation and antitumor activity of 9-hdroxy-11-demethylellipticine and some derivatives. Comparison with the corresponding ellipticines", (1980) *Euro. J. Med. Chem.* 15:503-510.

Guillonneau, C. et al., "Synthesis of 9-*O*-substituted derivatives of 9-hydroxy-5,6-dimethyl-6H-pyrido[4,3-*b*]carbazole-1-carboxylic acid (2-(dimethylamino)ethyl)amide and their 10-and 11-methyl analogues with improved antitumor activity", (1990) *J. Med. Chem.* 42:2191-2203.

Ishikura et al., "A Novel Entry to Pyrido [4,3-b] Carbazole: An Efficient Synthesis of Ellipticine", Chemical Abstract, vol. 132, Abstract 237230, 2000.

Jones, RM et al., "5'-Guanidinonaltrindole, a highly selective and potent k-opioid receptor antagonist" (2000) *Euro. J. Med. Chem.* 396:49-52.

Langlois et al., (975) Tetrahedron Letters 11: 955-958.

Lipkowski, AW et al., "Benzomorphan alkaloids: natural peptidomimetics of opioid peptide pharmacophores", (1995) *Letters in Peptide Science,* 2:177-181.

Olmsted, SL et al., "A remarkable change of opioid receptor selectivity on the attachment of a peptidomimetic κ address element to the δ antagonist, naltrindole: 5'-[($N^2$-alkylamidino)methyl]naltrindole derivatives as a novel class of κ opioid receptor antagonists" (1993) *J. Med. Chem.* 36:179-180.

Portoghese, PS et al., "Naltrindole 5'-isothiocyanate: a nonequilibrium, highly selective δ opioid receptor antagonist" (1990) *J. Med. Chem.* 33:1547-1548.

Portoghese, PS et al., "Design of peptidomimetic δ opioid receptor antagonists using the message-address concept" (1990) *J. Med. Chem.* 33:1714-1720.

Portoghese, PS et al., "Application of the message-address concept in the design of highly potent and selective non-peptide δ opioid receptor antagonists", (1988) *J. Med. Chem.* 31:281-282.

Portoghese, PS et al., "7'-substituted amino acid conjugates of naltrindole. Hydrophillic groups as determinants of selective antagonism of $\delta_1$ opioid receptor-mediated antinociception in mice." (1995) *J. Med.Chem.* 38:402-407.

Rastogi, et al. 1987 "Synthesis, Neuroleptic & Antiinflammatory Activities of 4a, 11a-cis-&trans-2-[γ-(p-Fluorobenzoyl)proppyl]-1,2,3,4,4a,5,11,11 a-octahydro-6H-pyrido[4,3-b]carbazoles & Related Derivatives," *India Journal of Chemistry* 26B: 335-340.

Série G "Chimie Organiqe.—Une nouvelle synthèse du système 6 H-pyrido-(4.3b) carbaxolique", (1972) *C.R. Acad. Sc. Paris,* t. 274:1948-1949.

Stevens, WC et al., "Potent and selective indolomorphinan antagonists of the kappa-opioid receptor", (2000) *J. Med. Chem.* 43:2759-2769.

Borowsky et al., "Antidepressant, anxiolytic and anorectic effects of a melanin-concentrating hormone-1 receptor antagonist," *Nature Medicine,* Aug. 2002, 8:825-830.

Forray, "The MCH receptor family: feeding brain disorders?," *Current Opinion in Pharmacology,* 2003, 3:85-89.

Sainsbury, "The synthesis of 6*H*-pyridol[4,3-*b*]carbazoles," *Synthesis,* 1976, 7:437-448.

*Stedman's Medical Dictionary,* 26th Edition, 1995, pp. 814 and 1634, Williams & Wilkins, Baltimore MD, USA.

Sainsbury, Malcom, 1977 "The Synthesis of 6*H*-Pyrido[4,3-*b*]Carbazoles" *Synthesis,* 7: 437-448.

\* cited by examiner

FUSED HETEROCYCLIC COMPOUNDS

This application claims the benefit under 35 U.S.C. § 119 of U.S. provisional application No. 60/424,456, the contents of which are hereby incorporated by reference in their entirety.

FIELD OF THE INVENTION

The present invention relates to compounds, compositions and methods useful in the treatment or prevention of conditions and disorders associated with eating behavior, energy homeostasis and anxiety.

BACKGROUND OF THE INVENTION

G-protein coupled receptors play important roles in diverse signaling processes, including those involved with sensory and hormonal signal transduction. Eating disorders, which represent a major health concern throughout the world, have been linked to GPCR regulation. On the one hand, disorders such as obesity, the excess deposition of fat in the subcutaneous tissues, manifest themselves by an increase in body weight. Individuals who are obese often have, or are susceptible to, medical abnormalities including respiratory difficulties, cardiovascular disease, diabetes and hypertension. On the other hand, disorders like cachexia, the general lack of nutrition and wasting associated with chronic disease and/or emotional disturbance, are associated with a decrease in body weight.

The neuropeptide melanin-concentrating hormone (MCH), a cyclic hypothalamic peptide involved in the regulation of several functions in the brain, has previously been found to be a major regulator of eating behavior and energy homeostasis. It has previously been determined that MCH is the natural ligand for the 353-amino acid orphan G-protein-coupled-receptor (GPCR) termed SLC-1 (also known as GPR24). Subsequent to this determination, SLC-1, which is sequentially homologous to the somatostatin receptors, is frequently referred to as melanin-concentrating hormone receptor (MCH receptor, MCHR or MCHR1) (see Chambers et al., *Nature* 400:261-65 (1999); Saito et al., *Nature* 400:265-69 (1999); and Saito et al., *TEM* 11(8):299-303 (2000)).

Compelling evidence exists that MCH is involved in regulation of eating behavior. First, intracerebral administration of MCH in rats resulted in stimulation of feeding. Next, mRNA corresponding to the MCH precursor is up-regulated in the hypothalamus of genetically obese mice and of fasted animals. Finally, mice deficient in MCH are leaner and have a decreased food intake relative to normal mice. MCH is believed to exert its activity by binding to MCHR, resulting in the mobilization of intracellular calcium and a concomitant reduction in cAMP levels (see Chambers et al., *Nature* 400:261-65 (1999); Shimada et al. *Nature* 396:670-74 (1998)). MCH also activates inwardly rectifying potassium channels, and MCHR has been found to interact with both Gαi protein and Gαq protein (Saito et al., *TEM* 11(8):299-303 (2000)). Moreover, analysis of the tissue localization of MCHR indicates that it is expressed in those regions of the brain involved in olfactory learning and reinforcement. The cumulative data suggest that modulators of MCHR should have an effect on neuronal regulation of food intake (see Saito et al., *Nature* 400:265-69 (1999)).

MCH has been shown to modulate behaviors other than feeding, such as anxiety (Gonzales et al. (1996) *Peptides* 17:171-177; Monzon et al. (1999) *Physiol. Behav.* 67:813-817).

The identification of MCHR modulators is useful for the study of physiological processes mediated by MCHR and the development of therapeutic agents for the treatment or prevention of conditions and disorders associated with weight regulation, learning, anxiety and other neuronal-related functions.

SUMMARY OF THE INVENTION

The present invention provides fused heterocyclic compounds and compositions, and methods of use thereof to treat or prevent conditions and disorders mediated by MCHR. In particular, the present invention provides compounds, compositions and methods for treating or preventing conditions and disorders associated with eating behavior, energy homeostasis and anxiety.

The compounds provided herein have the formula (I):

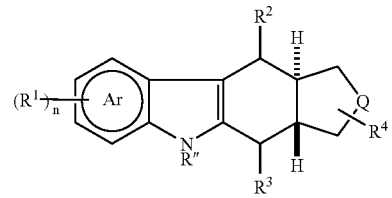

wherein

represents a single or fused aryl or heteroaryl ring;

Q is —N(R)— or —N(R)—($C_1$-$C_3$)alkylene-;

R is

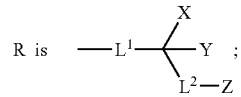

$L^1$ is a bond, ($C_1$-$C_4$)alkylene, ($C_1$-$C_4$)alkylenoxy and ($C_1$-$C_4$)alkylenamino;

$L^2$ is a bond, ($C_1$-$C_4$)alkylene, ($C_2$-$C_4$)alkenylene, ($C_2$-$C_4$)alkynylene, ($C_1$-$C_4$)alkylenoxy (e.g. —OCH$_2$CH$_2$—) or ($C_1$-$C_4$)alkylenamino (e.g. —NH—CH$_2$CH$_2$—);

R" is hydrogen or ($C_1$-$C_8$)alkyl;

each $R^1$ is independently selected from the group consisting of halogen, ($C_1$-$C_8$)alkyl, ($C_2$-$C_8$)alkenyl, ($C_2$-$C_8$)alkynyl, fluoro($C_1$-$C_4$)alkyl, —OR$^5$, —SR$^5$, fluoro($C_1$-$C_4$)alkoxy, aryl, aryl($C_1$-$C_4$)alkyl, —NO$_2$, —NR$^5$R$^6$, —C(O)R$^5$, —CO$_2$R$^5$, —C(O)NR$^5$R$^6$, —N(R$^6$)C(O)R$^5$, —N(R$^6$)CO$_2$R$^5$, —N(R$^7$)C(O)NR$^5$R$^6$, —S(O)$_m$NR$^5$R$^6$, —S(O)$_m$R$^5$, —CN and —N(R$^6$)S(O)$_m$R$^5$;

$R^2$ and $R^3$ are independently selected from the group consisting of hydrogen, halogen, ($C_1$-$C_8$)alkyl, ($C_2$-$C_8$)alkenyl, ($C_2$-$C_8$)alkynyl, fluoro($C_1$-$C_4$)alkyl, —OR$^8$, —SR$^8$, fluoro($C_1$-$C_4$)alkoxy, aryl, aryl($C_1$-$C_4$)alkyl, —NO$_2$, —NR$^8$R$^9$, =O, —C(O)R$^8$, —CO$_2$R$^8$, —C(O)NR$^8$R$^9$, —N(R$^9$)C(O)R$^8$, —N(R$^9$)CO$_2$R$^8$, —N(R$^{10}$)C(O)NR$^8$R$^9$, —S(O)$_m$NR$^8$R$^9$, —S(O)$_m$R$^8$, —CN and —N(R$^9$)S(O)$_m$R$^8$;

$R^4$ is selected from the group consisting of hydrogen, —OR$^{11}$, —C(O)R$^{11}$, —CO$_2$R$^{11}$, —C(O)NR$^{11}$R$^{12}$, —CN, ($C_1$-$C_4$)alkyl and aryl;

X and Y are independently selected from the group consisting of ($C_1$-$C_8$)alkyl, ($C_2$-$C_8$)alkenyl, ($C_2$-$C_8$)alkynyl, —$CO_2R^{13}$ and —$C(O)NR^{13}R^{14}$;

optionally, X and Y may be combined to form a 3-, 4-, 5-, 6- or 7-membered ring containing from 0 to 2 heteroatoms independently selected from the group consisting of N, O and S;

Z is selected from the group consisting of —$OR^{15}$, —$NR^{15}R^{16}$, —$NR^{15}R^{18}$, —$C(O)R^{15}$, —$CO_2R^{15}$, —$R^{18}$, —$C(O)NR^{15}R^{16}$, —$C(O)NR^{15}R^{18}$, —$SO_2NR^{15}R^{16}$, —$SO_2NR^{15}R^{18}$, —$NR^{16}SO_2R^{15}$, —$N(R^{15})N(R^{16})SO_2R^{17}$, —$C(O)N(R^{16})OR^{15}$, hydroxy($C_1$-$C_8$)alkyl, fluoro($C_1$-$C_4$)alkyl, heteroaryl, —$C(=NOR^{15})NR^{16}R^{17}$, —$C(R^{16}))=NOR^{15}$, —$NR^{16}(OR^{15})$, —$C(O)NR^{17}C(O)NR^{15}R^{16}$, —$NR^{17}C(O)NR^{16}C(O)R^{15}$ and —$NR^{17}C(O)NR^{15}R^{16}$;

$R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are independently selected from the group consisting of hydrogen, ($C_1$-$C_8$)alkyl, ($C_2$-$C_8$)alkenyl, ($C_2$-$C_8$)alkynyl, cyclo($C_3$-$C_6$)alkyl, fluoro($C_1$-$C_4$)alkyl, hetero($C_1$-$C_4$)alkyl, cyclohetero($C_3$-$C_6$)alkyl, aryl and aryl($C_1$-$C_4$)alkyl;

$R^{18}$ is a 5- or 6-membered ring containing from 0 to 4 heteroatoms selected from the group consisting of N, O and S (e.g. tetrazole);

optionally, when two R groups selected from the group consisting of $R^5$, $R^6$, $R^8$, $R^9$, $R^{11}$, $R^{12}$, $R^{13}$, $R^{14}$, $R^{15}$, $R^{16}$ and $R^{17}$ are attached to the same nitrogen atom, the R groups may be combined to form a 3-, 4-, 5-, 6- or 7-membered ring containing the nitrogen atom and from 0 to 2 additional heteroatoms selected from the group consisting of N, O and S;

the subscript m is 1 or 2; and
the subscript n is 0, 1 or 2.
In certain embodiments represents a benzene, naphthalene, pyrrole, pyrazole, imidazole, pyrazine, oxazole, isoxazole, thiazole, furan, thiophene, pyridine, pyrimidine, benzothiazole, purine, benzimidazole, indole, isoquinoline, quinoxaline or quinoline ring.

In certain embodiments represents a benzene ring.
In certain embodiments Q is —N(R)—.
In further embodiments, $R^3$ is hydrogen or =O.
In particular embodiments, represents a benzene ring, R" is hydrogen and $R^3$ is hydrogen.

Further compounds provided herein have the formula (II):

wherein $L^1$ is a bond, ($C_1$-$C_4$)alkylene, ($C_1$-$C_4$)alkylenoxy and ($C_1$-$C_4$)alkylenamino;

$L^2$ is a bond, ($C_1$-$C_4$)alkylene, ($C_2$-$C_4$)alkenylene, ($C_2$-$C_4$)alkynylene, ($C_1$-$C_4$)alkylenoxy (e.g —$OCH_2CH_2$—) or ($C_1$-$C_4$)alkylenamino (e.g. —$NH$—$CH_2CH_2$—);

R" is hydrogen or ($C_1$-$C_8$)alkyl;

each $R^1$ is independently selected from the group consisting of halogen, ($C_1$-$C_8$)alkyl, ($C_2$-$C_8$)alkenyl, ($C_2$-$C_8$)alkynyl, fluoro($C_1$-$C_4$)alkyl, —$OR^5$, —$SR^5$, fluoro($C_1$-$C_4$)alkoxy, aryl, aryl($C_1$-$C_4$)alkyl, —$NO_2$, —$NR^5R^6$, —$C(O)R^5$, —$CO_2R^5$, —$C(O)NR^5R^6$, —$N(R^6)C(O)R^5$, —$N(R^6)CO_2R^5$, —$N(R^7)C(O)NR^5R^6$, —$S(O)_mNR^5R^6$, —$S(O)_mR^5$, —CN and —$N(R^6)S(O)_mR^5$;

$R^2$ is selected from the group consisting of hydrogen, halogen, ($C_1$-$C_8$)alkyl, ($C_2$-$C_8$)alkenyl, ($C_2$-$C_8$)alkynyl, fluoro($C_1$-$C_4$)alkyl, —$OR^8$, —$SR^8$, fluoro($C_1$-$C_4$)alkoxy, aryl, aryl($C_1$-$C_4$)alkyl, —$NO_2$, —$NR^8R^9$, =O, —$C(O)R^8$, —$CO_2R^8$, —$C(O)NR^8R^9$, —$N(R^9)C(O)R^8$, —$N(R^9)CO_2R^8$, —$N(R^{10})C(O)NR^8R^9$, —$S(O)_mNR^8R^9$, —$S(O)_mR^8$, —CN and —$N(R^9)S(O)_mR^8$;

$R^4$ is selected from the group consisting of hydrogen, —$OR^{11}$, —$C(O)R^{11}$, —$CO_2R^{11}$, —$C(O)NR^{11}R^{12}$, —CN, ($C_1$-$C_4$)alkyl and aryl;

X and Y are independently selected from the group consisting of ($C_1$-$C_8$)alkyl, ($C_2$-$C_8$)alkenyl, ($C_2$-$C_8$)alkynyl, —$CO_2R^{13}$ and —$C(O)NR^{13}R^{14}$;

optionally, X and Y may be combined to form a 3-, 4-, 5-, 6- or 7-membered ring containing from 0 to 2 heteroatoms independently selected from the group consisting of N, O and S;

Z is selected from the group consisting of —$OR^{15}$, —$NR^{15}R^{16}$, —$NR^{15}R^{18}$, —$C(O)R^{15}$, —$CO_2R^{15}$, —$R^{18}$, —$C(O)NR^{15}R^{16}$, —$C(O)NR^{15}R^{18}$, —$SO_2NR^{15}R^{16}$, —$SO_2NR^{15}R^{18}$, $NR^{16}SO_2R^{15}$, —$N(R^{15})N(R^{16})SO_2R^{17}$, —$C(O)N(R^{16})OR^{15}$, hydroxy($C_1$-$C_8$)alkyl, fluoro($C_1$-$C_4$)alkyl, heteroaryl, —$C(=NOR^{15})NR^{16}R^{17}$, —$C(R^{16})=NOR^{15}$, —$NR^{16}(OR^{15})$, —$C(O)NR^{17}C(O)NR^{15}R^{16}$, —$NR^{17}C(O)NR^{16}C(O)R^{15}$ and —$NR^{17}C(O)NR^{15}R^{16}$;

$R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are independently selected from the group consisting of hydrogen, ($C_1$-$C_8$)alkyl, ($C_2$-$C_8$)alkenyl, ($C_2$-$C_8$)alkynyl, cyclo($C_3$-$C_6$)alkyl, fluoro($C_1$-$C_4$)alkyl, hetero($C_1$-$C_4$)alkyl, cyclohetero($C_3$-$C_6$)alkyl, aryl and aryl($C_1$-$C_4$)alkyl;

$R^{18}$ is a 5- or 6-membered ring containing from 0 to 4 heteroatoms selected from the group consisting of N, O and S (e.g. tetrazole);

optionally, when two R groups selected from the group consisting of $R^5$, $R^6$, $R^8$, $R^9$, $R^{11}$, $R^{12}$, $R^{13}$, $R^{14}$, $R^{15}$, $R^{16}$ and $R^{17}$ are attached to the same nitrogen atom, the R groups may be combined to form a 3-, 4-, 5-, 6- or 7-membered ring containing the nitrogen atom and from 0 to 2 additional heteroatoms selected from the group consisting of N, O and S;

the subscript m is 1 or 2; and the subscript n is 0, 1 or 2.

The compounds provided in the above formulas are meant to include all pharmaceutically acceptable salts, hydrates, solvates or prodrugs thereof.

The pharmaceutical compositions provided herein comprise a pharmaceutically acceptable carrier or excipient in combination with a compound of formula I or II.

Methods for treating or preventing a condition or disorder selected from the group consisting of obesity, an eating disorder, an anxiety disorder and a mood disorder are provided herein. The methods comprise administering to a subject in need thereof a therapeutically effective amount of one of the foregoing compounds or pharmaceutical compositions.

Other objects, features and advantages of the present invention will become apparent to those skilled in the art from the following description and claims.

DETAILED DESCRIPTION OF THE INVENTION

Abbreviations and Definitions

Figure 1:
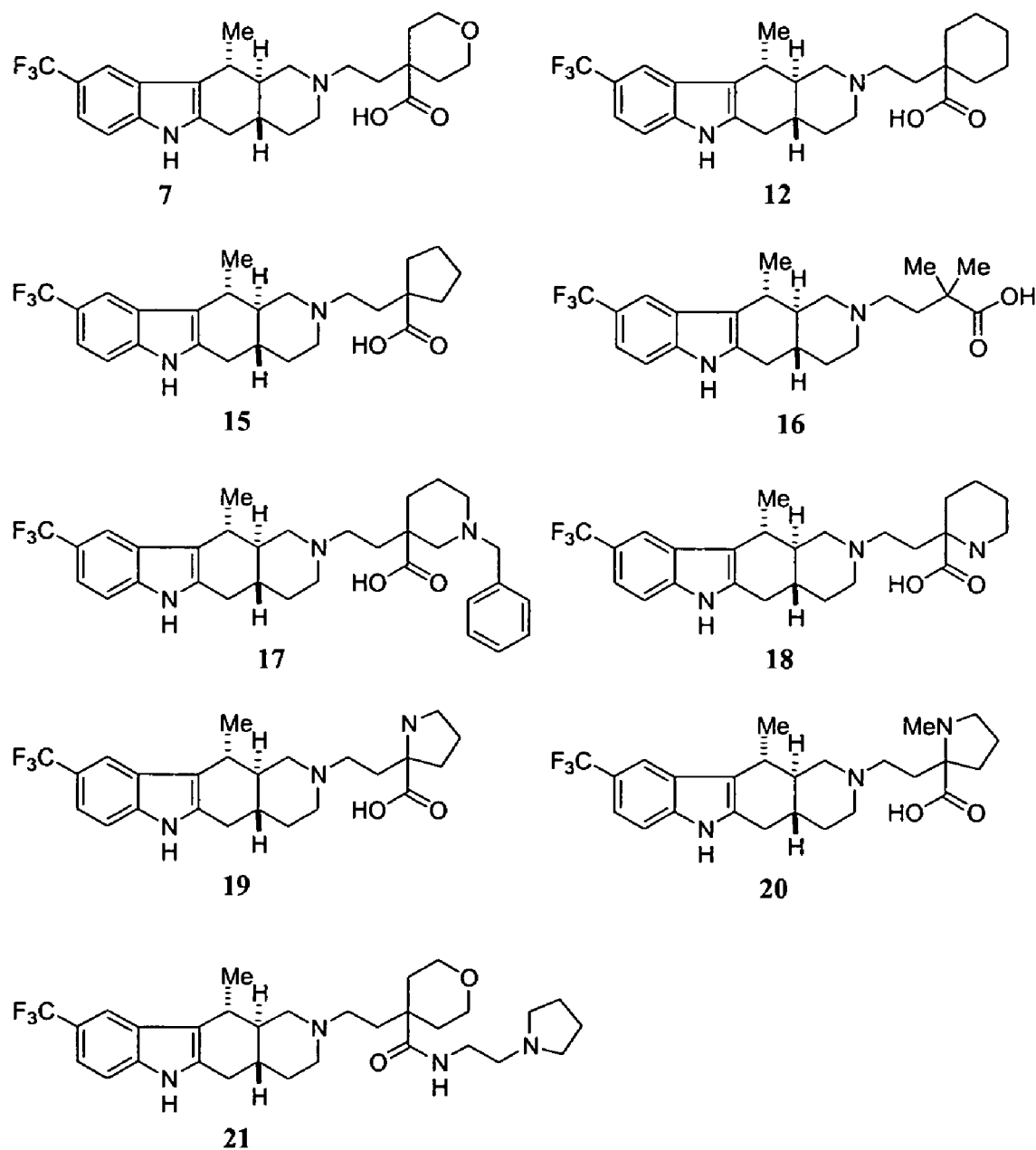
FIG. 1 provides the structures of exemplary compounds of the invention.

The abbreviations used herein are conventional, unless otherwise defined.

The term "MCHR" refers to the melanin-concentrating hormone receptor protein 1 (MCHR1), unless otherwise stated.

The terms "treat", "treating" and "treatment" refer to a method of alleviating or abrogating a disease and/or its attendant symptoms.

The terms "prevent", "preventing" and "prevention" refer to a method of decreasing the probability or eliminating the possibility that a disease will be contracted.

As used herein, the term "MCHR-mediated condition or disorder" and the like refers to a condition or disorder characterized by inappropriate, e.g., less than or greater than normal, MCHR activity. An MCHR-mediated condition or disorder may be completely or partially mediated by inappropriate MCHR activity. However, an MCHR-mediated condition or disorder is one in which modulation of MCHR results in some effect on the underlying condition or disease (e.g., an MCHR antagonist results in some improvement in patient well-being in at least some patients). Exemplary MCHR-mediated conditions and disorders include obesity, eating disorders and other behavioral disorders, such as anxiety disorders and mood disorders.

The term "therapeutically effective amount" refers to that amount of the compound being administered sufficient to prevent development of or alleviate to some extent one or more of the symptoms of the condition or disorder being treated.

As used herein, the term "obesity" refers to the excessive accumulation of body fat. Obesity may have genetic, environmental (e.g., expending less energy than is consumed) and regulatory determinants. Cardiovascular disorders, lipid disorders and metabolic disorders, such as hypertension, hyperlidemia, coronary artery disease and diabetes, are commonly associated with obesity.

As used herein, the terms "eating disorder", "feeding disorder", and the like refer to an emotional and/or behavioral disturbance associated with an excessive decrease in body weight and/or inappropriate efforts to avoid weight gain, e.g., fasting, self-induced vomiting, laxative or diuretic abuse. Depression is commonly associated with eating disorders. Exemplary eating disorders include anorexia nervosa and bulimia.

As used herein, the term "anxiety disorder" refers to an emotional and/or behavioral disturbance characterized by persistent and pervasive worry or restlessness, tension or irritability about, e.g., health, work, money or family, for no clear reason. An anxiety disorder may be accompanied by tachycardia or dyspnea. Exemplary anxiety disorders include anxiety, generalized anxiety disorder, panic attacks, panic disorder and obsessive-compulsive disorder (OCD).

As used herein, the term "mood disorder" refers to an emotional and/or behavioral disturbance characterized by persistent and pervasive bouts of euphoria and/or depression. Exemplary mood disorders include depression and bipolar disorders. Anxiety is frequently associated with mood disorders, such as depression.

The term "modulate" refers to the ability of a compound to increase or decrease the function, or activity, of MCHR. Modulation, as described herein, includes the antagonism or agonism of MCHR, either directly or indirectly. Antagonist are compounds that, e.g., partially or totally block stimulation, decrease, prevent, delay activation, inactivate, inhibit, desensitize, or down-regulate signal transduction. Agonists are compounds that, e.g., stimulate, increase, activate, open, facilitate, enhance activation, sensitize or up-regulate signal transduction.

The term "alkyl," by itself or as part of another substituent, means, unless otherwise stated, a straight or branched chain, or cyclic hydrocarbon radical, or combination thereof, which is fully saturated, having the number of carbon atoms designated (i.e. $C_1$-$C_8$ means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. As used herein, ($C_1$-$C_8$)alkyl refers to an alkyl group having from one to eight carbon atoms and includes, e.g., ($C_1$-$C_4$)alkyl.

The term "alkenyl", by itself or as part of another substituent, means a straight or branched chain, or cyclic hydrocarbon radical, or combination thereof, which may be mono- or polyunsaturated, having the number of carbon atoms designated (i.e. $C_2$-$C_8$ means two to eight carbons) and one or more double bonds. Examples of alkenyl groups include vinyl, allyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. $C_2$-$C_8$ means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having seven or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$ Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., $C_3$-$C_8$ means three to eight carbons) and a heterocycloalkyl group consists of the number of atoms designated (i.e., $C_2$-$C_8$ means two to eight carbons) and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo($C_1$-$C_4$)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). Accordingly, the term "fluoro($C_1$-$C_4$)alkyl" includes fluoromethyl, trifluoromethyl, 2,2,2-trifluoroethyl, pentafluoroethyl, 1,1-difluoroethyl, and the like. The term "perhaloalkyl" means, unless otherwise stated, alkyl substituted with (2m'+1) halogen atoms, where m' is the total number of carbon atoms in the alkyl group. For example the term "perhalo($C_1$-$C_4$)alkyl" is meant to include trifluoromethyl, pentachloroethyl, 1,1,1-trifluoro-2-bromo-2-chloroethyl, and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl and 4-biphenyl.

The term "heteroaryl" refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R"', —OC(O)R', —C(O)R', —CO$_2$R', —CONR'R", —OC(O)NR'R", —NR"C(O)R', —NR'—C(O)NR"R"', —NR'—SO$_2$NR"R"', —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R', —CN and —NO$_2$, in a number ranging from zero to three, with those groups having zero, one or two substituents being particularly preferred. R', R" and R"' each independently refer to hydrogen, unsubstituted ($C_1$-$C_8$)alkyl and heteroalkyl, fluoro($C_1$-$C_4$)alkyl, unsubstituted aryl, aryl substituted with one to three halogens, unsubstituted alkyl, alkoxy or thioalkoxy groups, or aryl($C_1$-$C_4$)alkyl groups.

When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —$CF_3$ and —$CH_2CF_3$).

Preferred substituents for the alkyl and heteroalkyl radicals are selected from: —OR', =O, —NR'R", —SR', halogen, —SiR'R"R''', —OC(O)R', —C(O)R', —$CO_2$R', —CONR'R", —OC(O)NR'R", —NR"C(O)R', —NR"$CO_2$R', —NR'—$SO_2$NR"R''', —S(O)R', —$SO_2$R', —$SO_2$NR'R", —NR"$SO_2$R', —CN and —$NO_2$, where R' and R" are as defined above. Further preferred substituents are selected from: —OR', =O, —NR'R", halogen, —OC(O)R', —$CO_2$R', —CONR'R", —OC(O)NR'R", —NR"C(O)R', —NR"$CO_2$R', —NR'—$SO_2$NR"R''', —$SO_2$R', —$SO_2$NR'R", —NR"$SO_2$R', —CN and —$NO_2$ Similarly, substituents for the aryl and heteroaryl groups are varied and selected from: halogen, —OR', —OC(O)R', —NR'R", —SR', —R', —CN, —$NO_2$, —$CO_2$R', —CONR'R", —C(O)R', —OC(O)NR'R", —NR"C(O)R', —NR"$CO_2$R', —NR'—C(O)NR"R''', —NR'—$SO_2$NR"R''', —NH—C($NH_2$)=NH, —NR'C($NH_2$)=NH, —NH—C($NH_2$)=NR', —S(O)R', —$SO_2$R', —$SO_2$NR'R", —NR"$SO_2$R', —$N_3$, —CH(Ph)$_2$, perfluoro($C_1$-$C_4$)alkoxy and perfluoro($C_1$-$C_4$)alkyl, in a number ranging from zero to the total number of open valences on the aromatic ring system; and where R', R" and R''' are independently selected from hydrogen, ($C_1$-$C_8$)alkyl and heteroalkyl, unsubstituted aryl and heteroaryl, (unsubstituted aryl)-($C_1$-$C_4$)alkyl and (unsubstituted aryl)oxy-($C_1$-$C_4$)alkyl. Typically, an aryl or heteroaryl group will have from zero to three substituents, with those groups having two or fewer substituents being preferred in the present invention. More preferably, an aryl or heteroaryl group will be unsubstituted or monosubstituted. Most preferably, an aryl or heteroaryl group will be unsubstituted.

Preferred substituents for aryl and heteroaryl groups are selected from: halogen, —OR', —OC(O)R', —NR'R", —SR', —R', —CN, —$NO_2$, —$CO_2$R', —CONR'R", —C(O)R', —OC(O)NR'R", —NR"C(O)R', —S(O)R', —$SO_2$R', —$SO_2$NR'R", —NR"$SO_2$R', —$N_3$, —CH(Ph)$_2$, perfluoro($C_1$-$C_4$)alkoxy and perfluoro($C_1$-$C_4$)alkyl, where R' and R" are as defined above. Further preferred substituents are selected from: halogen, —OR', —OC(O)R', —NR'R", —R', —CN, —$NO_2$, —$CO_2$R', —CONR'R", —NR"C(O)R', —$SO_2$R', —$SO_2$NR'R", —NR"$SO_2$R', perfluoro($C_1$-$C_4$)alkoxy and perfluoro($C_1$-$C_4$)alkyl As used herein, the substituent —$CO_2$H, includes bioisosteric replacements therefor, such as:

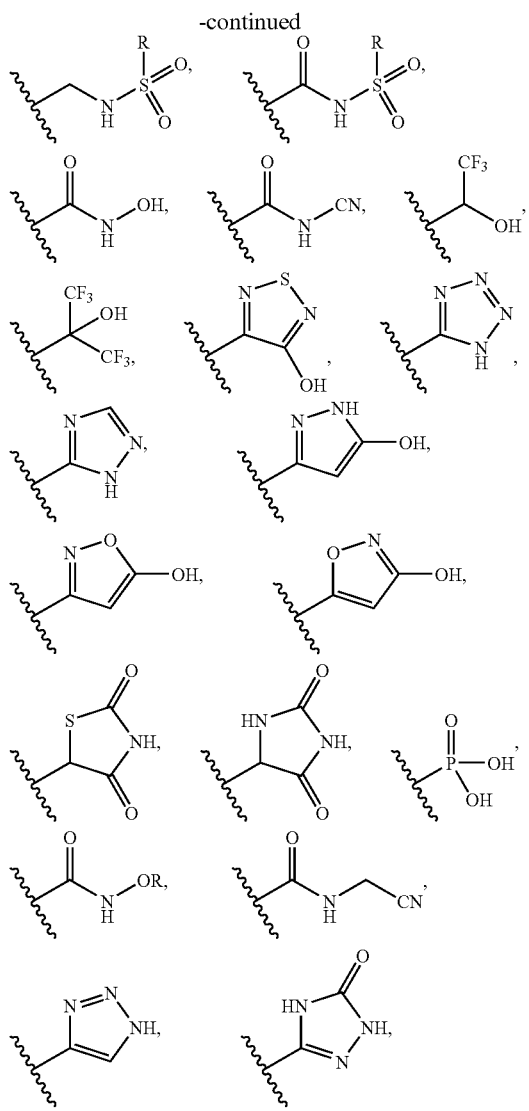

and the like. See, e.g., *The Practice of Medicinal Chemistry*; Wermuth, C. G., Ed.; Academic Press: New York, 1996; p. 203.

Two of the substituents on adjacent atoms of the aryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula -A-(CH$_2$)$_r$—B—, wherein A and B are independently —CH$_2$—, —O—, —NH—, —S—, —S(O)—, —SO$_2$—, —SO$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —SO$_2$—, or —SO$_2$NR'—. The substituent R' in —NR'— and —SO$_2$NR'— is selected from the group consisting of hydrogen or unsubstituted ($C_1$-$C_6$) alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al. (1977) *J. Pharm. Sci.* 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, enantiomers, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

EMBODIMENTS OF THE INVENTION

MCHR (GenBank Accession No. U71092) is expressed in brain, at moderate levels in the eye and skeletal muscle, and in low levels in tongue and the pituitary gland. Evidence suggests that MCHR is involved in, inter alia, olfactory learning, regulation of feeding behavior and energy metabolism, regulation of the hypothalmic-pituitary-adrenocortical axis following stress, arousal and the sensation of anxiety (Saito et al., *TEM* 11(8):299-303 (2000)). The compounds of the present invention inhibit MCHR activity, and thus, are useful in, for example, the treatment or prevention of disorders associated with these processes.

Compounds

In one aspect, the present invention provides compounds represented by the formula (I):

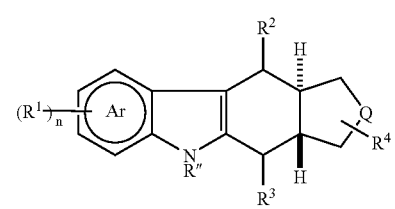

wherein or a pharmaceutically acceptable salt, hydrate, solvate or prodrug thereof. In formula I,

represents a single or fused aryl or heteroaryl ring. For instance,

can represent benzene, naphthalene, pyrrole, pyrazole, imidazole, pyrazine, oxazole, isoxazole, thiazole, furan, thiophene, pyridine, pyrimidine, benzothiazole, purine, benzimidazole, indole, isoquinoline, quinoxaline or quinoline ring. In preferred embodiments,

represents benzene.

The symbol Q represents —N(R)— or —N(R)—($C_1$-$C_3$)alkylene-. In certain embodiments the symbol Q represents —N(R)—.

The symbol R represents

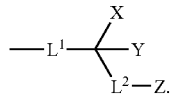

The symbol $L^1$ represents a divalent linkage selected from a bond, ($C_1$-$C_4$)alkylene, ($C_1$-$C_4$)alkylenoxy and ($C_1$-$C_4$)alkylenamino. Exemplary $L^1$ groups are a single bond, methylene, ethylene, n-propylene and n-butylene. The symbol $L^2$ represents a divelent linkage selected from a bond, ($C_1$-$C_4$)alkylene, ($C_2$-$C_4$)alkenylene, ($C_2$-$C_4$)alkynylene, ($C_1$-$C_4$)alkylenoxy and ($C_1$-$C_4$)alkylenamino. Exemplary $L^2$ groups are a single bond, methylene, ethylene, n-propylene and n-butylene.

The letters X and Y represent independently ($C_1$-$C_8$)alkyl, ($C_2$-$C_8$)alkenyl, ($C_2$-$C_8$)alkynyl, —$CO_2R^{13}$ or —C(O)$NR^{13}R^{14}$. Optionally, X and Y may be combined to form a 3-, 4-, 5-, 6- or 7-membered ring containing from 0 to 2 heteroatoms selected from N, O and S.

The letter Z represents —$OR^{12}$, —$N^{12}R^{13}$, —$CO_2R^{12}$, —$R^{15}$, —C(O)$NR^{12}R^{13}$, —C(O)$NR^{12}R^{15}$, —$SO_2NR^{12}R^{13}$, —$NR^{13}SO_2R^{15}$, —$N(R^{12})N(R^{13})SO_2R^{14}$, —C(O)N($R^{13}$)$OR^{12}$, fluoro($C_1$-$C_4$)alkyl, heteroaryl, —C(=$NOR^{12}$)$NR^{13}R^{14}$, —C($R^{13}$)=$NOR^{12}$, —$NR^{13}$($OR^{12}$), —C(O)$NR^{14}$C(O)$NR^{12}R^{13}$, —$NR^{14}$C(O)$NR^{13}$C(O)$R^{12}$ and —$NR^{14}$C(O)$NR^{12}R^{13}$. Exemplary —C(X)(Y)($L^2$Z) groups are:

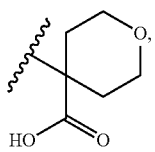

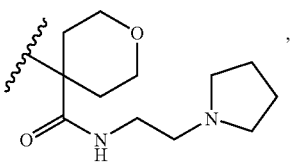

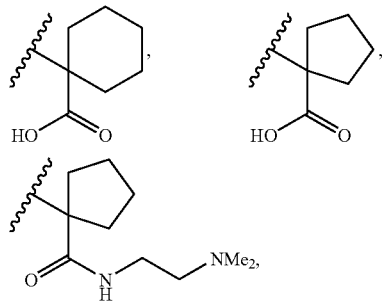

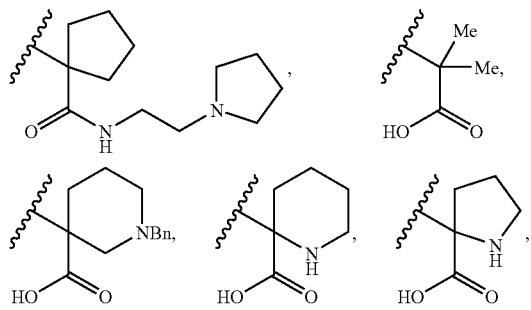

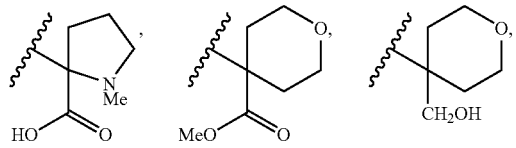

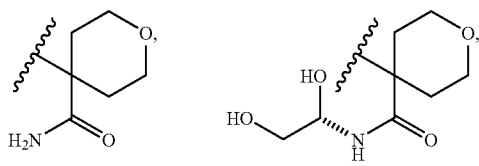

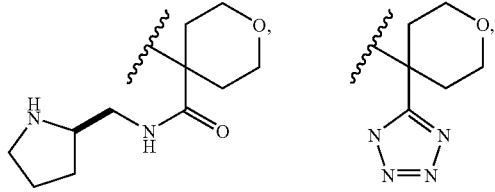

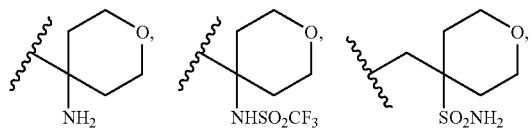

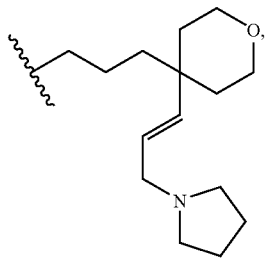

-continued

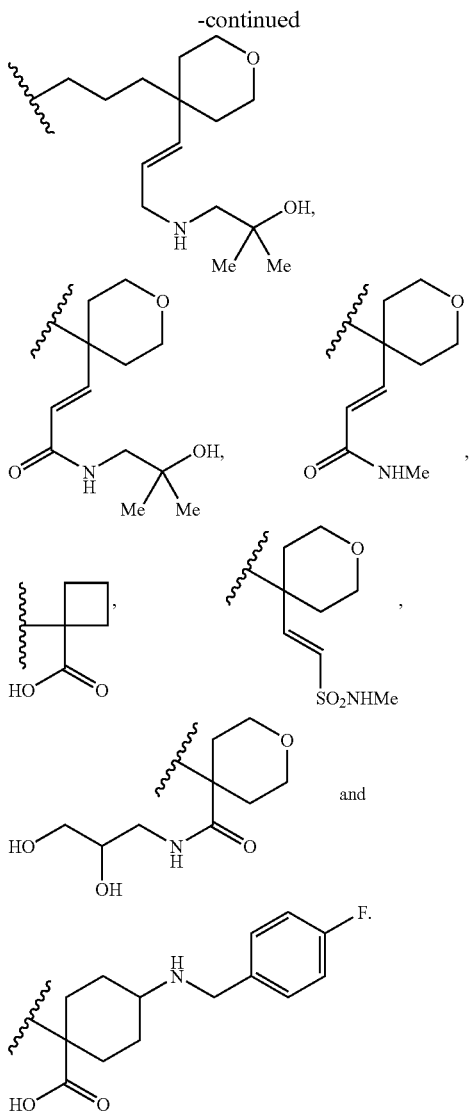

R" is hydrogen or $(C_1-C_8)$alkyl.

Each $R^1$ is independently halogen, $(C_1-C_8)$alkyl, $(C_2-C_8)$alkenyl, $(C_2-C_8)$alkynyl, fluoro$(C_1-C_4)$alkyl, —OR$^5$, —SR$^5$, fluoro$(C_1-C_4)$alkoxy, aryl, aryl$(C_1-C_4)$alkyl, —NO$_2$, —NR$^5$R$^6$, —C(O)R$^5$, —CO$_2$R$^5$, —C(O)NR$^5$R$^6$, —N(R$^6$)C(O)R$^5$, —N(R$^6$)CO$_2$R$^5$, —N(R$^7$)C(O)NR$^5$R$^6$, —S(O)$_m$NR$^5$R$^6$, —S(O)$_m$R$^5$, —CN or —N(R$^6$)S(O)$_m$R$^5$. Exemplary $R^1$ groups are Cl and CF$_3$.

$R^2$ and $R^3$ are independently selected from hydrogen, halogen, $(C_1-C_8)$alkyl, $(C_2-C_8)$alkenyl, $(C_2-C_8)$alkynyl, fluoro$(C_1-C_4)$alkyl, —OR$^8$, —SR$^8$, fluor$(C_1-C_4)$alkoxy, aryl, aryl$(C_1-C_4)$alkyl, —NO$_2$, —NR$^8$R$^9$, =O, —C(O)R$^8$, —CO$_2$R$^8$, —C(O)NR$^8$R$^9$, —N(R$^9$)C(O)R$^8$, —N(R$^9$)CO$_2$R$^8$, —N(R$^{10}$)C(O)NR$^8$R$^9$, —S(O)$_m$NR$^8$R$^9$, —S(O)$_m$R$^8$, —CN and —N(R$^9$)S(O)R$^8$. Exemplary $R^2$ groups are methyl, isopropyl, trifluoromethyl, hydroxy, methoxy, hydroxymethyl, trifluoromethoxy, phenyl and =O. In certain embodiments, $R^3$ is hydrogen or =O.

$R^4$ is hydrogen, —OR$^{11}$, —C(O)R$^{11}$, —CO$_2$R$^{11}$, —C(O)NR$^{11}$R$^{12}$, —CN, $(C_1-C_4)$alkyl or aryl.

$R^5$, $R^6$, $R^7$, $R^8$, $R^9$, $R^{10}$, $R^{11}$, $R^{12}$, $R^{13}$, $R^{14}$, $R^{16}$ and $R^{17}$ are independently selected from hydrogen, $(C_1-C_8)$alkyl, $(C_2-C_8)$alkenyl, $(C_2-C_8)$alkynyl, fluoro$(C_1-C_4)$alkyl, hetero$(C_1-C_4)$alkyl, aryl and aryl$(C_1-C_4)$alkyl and $R^{18}$ is a 5- or 6-membered ring containing from 1 to 3 heteroatoms selected from N, O and S. The subscript m is 1 or 2 and the subscript n is 0, 1 or 2. Optionally, when two R groups selected from the group consisting of $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are attached to the same nitrogen atom, the R groups may be combined to form a 3-, 4-, 5-, 6- or 7-membered ring containing the nitrogen atom and from 0 to 2 additional heteroatoms selected from N, O and S.

In particular embodiments,

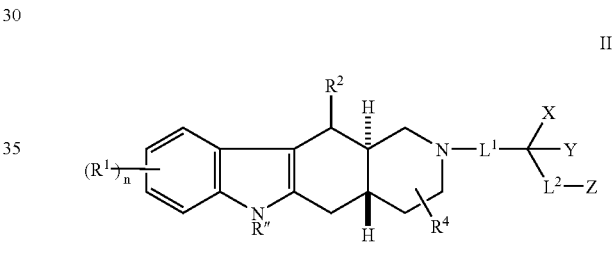

represents a benzene ring, R" is hydrogen and $R^3$ is hydrogen.

In another aspect, the present invention provides compounds of formula (II):

$$\text{(II)}$$

or a pharmaceutically acceptable salt, hydrate, solvate or prodrug thereof. In formula II, the symbol $L^1$ represents a divalent linkage selected from a bond, $(C_1-C_4)$alkylene, $(C_1-C_4)$alkylenoxy and $(C_1-C_4)$alkylenamino. Exemplary $L^1$ groups are a single bond, methylene, ethylene, n-propylene and n-butylene. The symbol $L^2$ represents a divalent linkage selected from a bond, $(C_1-C_4)$alkylene, $(C_2-C_4)$alkenylene, $(C_2-C_4)$alkynylene, $(C_1-C_4)$alkylenoxy and $(C_1-C_4)$alkylenamino. Exemplary $L^2$ groups are a single bond, methylene, ethylene, n-propylene and n-butylene.

The letters X and Y represent independently $(C_1-C_8)$alkyl, $(C_2-C_8)$alkenyl, $(C_2-C_8)$alkynyl, —CO$_2$R$^{13}$ or —C(O)NR$^{13}$R$^{14}$. Optionally, X and Y may be combined to form a 3-, 4-, 5-, 6- or 7-membered ring containing from 0 to 2 heteroatoms selected from N, O and S.

The letter Z represents —OR$^{12}$, —NR$^{12}$R$^{13}$, —CO$_2$R$^{13}$, —R$^{15}$, —C(O)NR$^{12}$R$^{13}$, —C(O)NR$^{12}$R$^{15}$, —SO$_2$NR$^{13}$R$^{13}$, —NR$^{13}$SO$_2$R$^{15}$, —N(R$^{12}$)N(R$^{13}$)SO$_2$R$^{14}$, —C(O)N(R$^{13}$)OR$^{12}$, fluoro$(C_1-C_4)$alkyl, heteroaryl, —C(=NOR$^{12}$)NR$^{13}$R$^{14}$, —C(R$^3$)=NOR$^{12}$, —NR$^{13}$(OR$^{12}$), —C(O)NR$^{14}$C(O)NR$^{12}$R$^{13}$, —NR$^{14}$C(O)NR$^{13}$C(O)R$^{12}$ and —NR$^{14}$C(O)NR$^{12}$R$^{13}$. Exemplary —C(X)(Y)(L$^2$Z) groups are:

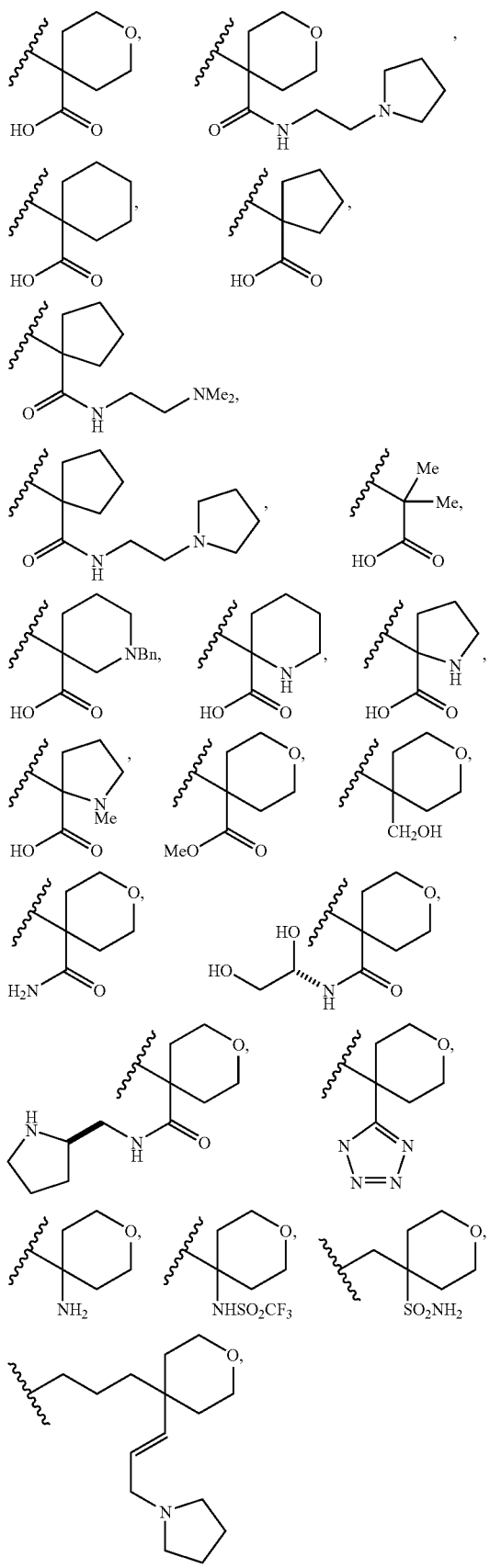
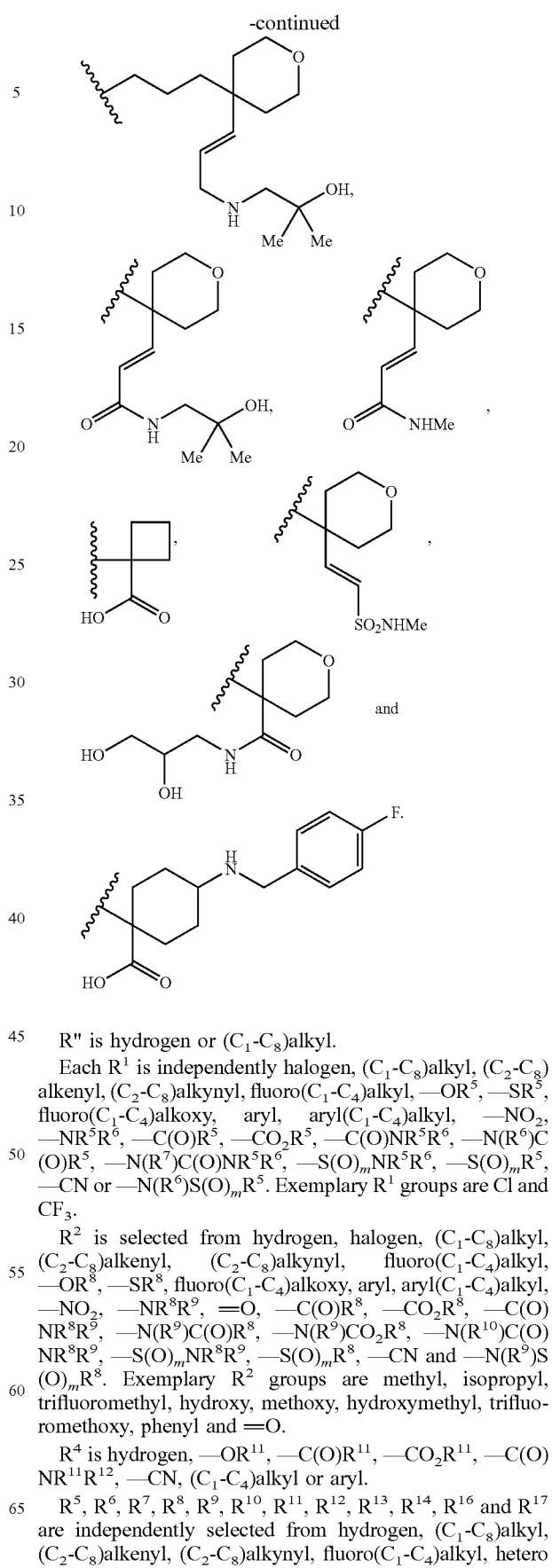

R" is hydrogen or $(C_1-C_8)$alkyl.

Each $R^1$ is independently halogen, $(C_1-C_8)$alkyl, $(C_2-C_8)$alkenyl, $(C_2-C_8)$alkynyl, fluoro$(C_1-C_4)$alkyl, —$OR^5$, —$SR^5$, fluoro$(C_1-C_4)$alkoxy, aryl, aryl$(C_1-C_4)$alkyl, —$NO_2$, —$NR^5R^6$, —$C(O)R^5$, —$CO_2R^5$, —$C(O)NR^5R^6$, —$N(R^6)C(O)R^5$, —$N(R^7)C(O)NR^5R^6$, —$S(O)_mNR^5R^6$, —$S(O)_mR^5$, —CN or —$N(R^6)S(O)_mR^5$. Exemplary $R^1$ groups are Cl and $CF_3$.

$R^2$ is selected from hydrogen, halogen, $(C_1-C_8)$alkyl, $(C_2-C_8)$alkenyl, $(C_2-C_8)$alkynyl, fluoro$(C_1-C_4)$alkyl, —$OR^8$, —$SR^8$, fluoro$(C_1-C_4)$alkoxy, aryl, aryl$(C_1-C_4)$alkyl, —$NO_2$, —$NR^8R^9$, =O, —$C(O)R^8$, —$CO_2R^8$, —$C(O)NR^8R^9$, —$N(R^9)C(O)R^8$, —$N(R^9)CO_2R^8$, —$N(R^{10})C(O)NR^8R^9$, —$S(O)_mNR^8R^9$, —$S(O)_mR^8$, —CN and —$N(R^9)S(O)_mR^8$. Exemplary $R^2$ groups are methyl, isopropyl, trifluoromethyl, hydroxy, methoxy, hydroxymethyl, trifluoromethoxy, phenyl and =O.

$R^4$ is hydrogen, —$OR^{11}$, —$C(O)R^{11}$, —$CO_2R^{11}$, —$C(O)NR^{11}R^{12}$, —CN, $(C_1-C_4)$alkyl or aryl.

$R^5$, $R^6$, $R^7$, $R^8$, $R^9$, $R^{10}$, $R^{11}$, $R^{12}$, $R^{13}$, $R^{14}$, $R^{16}$ and $R^{17}$ are independently selected from hydrogen, $(C_1-C_8)$alkyl, $(C_2-C_8)$alkenyl, $(C_2-C_8)$alkynyl, fluoro$(C_1-C_4)$alkyl, hetero ($C_1$-$C_4$)alkyl, aryl and aryl($C_1$-$C_4$)alkyl and $R^{18}$ is a 5- or 6-membered ring containing from 1 to 3 heteroatoms selected from N, O and S. The subscript m is 1 or 2 and the subscript n is 0, 1 or 2. Optionally, when two R groups selected from the group consisting $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are attached to the same nitrogen atom, the R groups may be combined to form a 3-, 4-, 5-, 6- or 7-membered ring containing the nitrogen atom and from 0 to 2 additional heteroatoms selected from N, O and S.

Compounds of the invention feature a pyrido[4,3-b]carbazole-derived ring, minimally substituted at the 2- and 11-positions. The ring numbering system used herein is illustrated below.

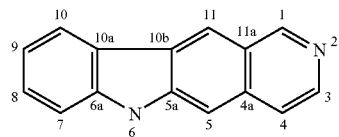

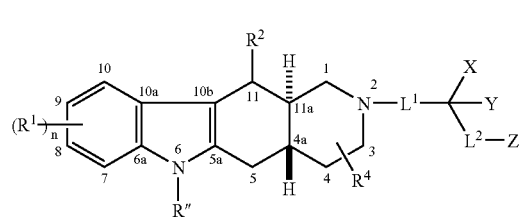

One of skill in the art will understand that formula II encompasses two enantiomers. The enantiomers have the structural orientations represented by the following formulae:

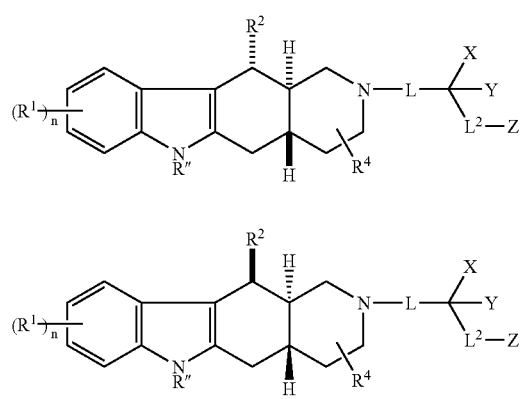

Within formula I or II above, a number of groups of embodiments are preferred, described below.

In one group of preferred embodiments, $L^1$ is ($C_1$-$C_4$) alkylene. In a preferred embodiment, $L^1$ is unsubstituted ($C_1$-$C_4$)alkylene or —$(CH_2)_p$—, wherein the subscript p is an integer of from 1 to 4. In a further preferred embodiment, p is 1, 2 or 3. In a still further preferred embodiment, p is 2 or 3. In a particularly preferred embodiment, p is 2.

One group of preferred embodiments is represented by the formula (III):

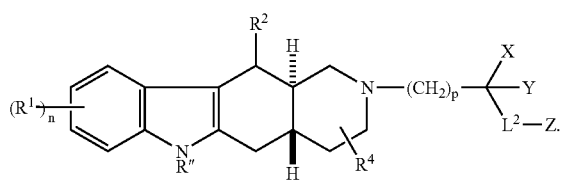

In a preferred embodiment, X and Y are combined to form a 3-, 4-, 5-, 6- or 7-membered ring containing from 0 to 2 heteroatoms selected from O, N and S. In a further preferred embodiment, X and Y are combined to form a 5- or 6-membered ring containing from 0 to 2 heteroatoms selected from O, N and S. In a particularly preferred embodiment, X and Y are combined to form a 5- or 6-membered ring containing 0 heteroatoms, 1 nitrogen atom or 1 oxygen atom.

In another preferred embodiment, $L^2$ is a bond and Z is —$CO_2R^{15}$ or —$CO_2NR^{15}R^{16}$.

In another group of preferred embodiments, R" is hydrogen.

In another group of preferred embodiments, R" is substituted ($C_1$-$C_8$)alkyl. In a preferred embodiment, R" is ($C_1$-$C_8$)alkyl substituted with hydroxy, alkylamino (e.g., —NHMe) or carboxy (—$CO_2H$). In a particularly preferred embodiment, R" is ($C_3$-$C_8$)alkyl substituted with hydroxy, alkylamino or carboxy.

In another group of preferred embodiments, $R^1$ is independently halogen, ($C_1$-$C_4$)alkyl, fluoro($C_1$-$C_4$)alkyl, —$OR^5$, fluoro($C_1$-$C_4$)alkoxy, —$CO_2R^5$, —$S(O)_mNR^5R^6$, —$S(O)_nR^5$ or —CN. In a further preferred embodiment, $R^1$ is independently halogen or fluoro($C_1$-$C_4$)alkyl. In a still further preferred embodiment, $R^1$ is halogen or fluoro($C_1$-$C_4$)alkyl and the subscript n is 0 or 1. In a particularly preferred embodiment, $R^1$ is fluoro($C_1$-$C_4$)alkyl and the subscript n is 0 or 1.

In another group of preferred embodiments, $R^2$ is ($C_1$-$C_4$)alkyl or aryl.

In another group of preferred embodiments, $R^4$ is hydrogen.

Also particularly preferred are those embodiments that combine two or more of these preferred groups. Accordingly, in one group of particularly preferred embodiments, R" and $R^4$ are hydrogen.

In another group of particularly preferred embodiments, R" and $R^4$ are hydrogen and $R^2$ is ($C_1$-$C_4$)alkyl or aryl.

In another group of particularly preferred embodiments, R" and $R^4$ are hydrogen, $R^2$ is independently halogen, ($C_1$-$C_4$)alkyl, fluoro($C_1$-$C_4$)alkyl, —$OR^5$, fluoro($C_1$-$C_4$) alkoxy, —$CO_2R^5$, —$S(O)_nNR^5R^6$, —$S(O)R^5$ or —CN and $R^2$ is ($C_1$-$C_4$)alkyl or aryl. In a particularly preferred embodiment, R" and $R^4$ are hydrogen, $R^1$ is halogen or fluoro($C_1$-$C_4$)alkyl, n is 1 and $R^2$ is ($C_1$-$C_4$)alkyl or aryl. In a more particularly preferred embodiment, R" and $R^4$ are hydrogen, $R^1$ is fluoro($C_1$-$C_4$)alkyl, n is 1 and $R^2$ is ($C_1$-$C_4$) alkyl or aryl.

One group of particularly preferred embodiments is represented by the formula (IV):

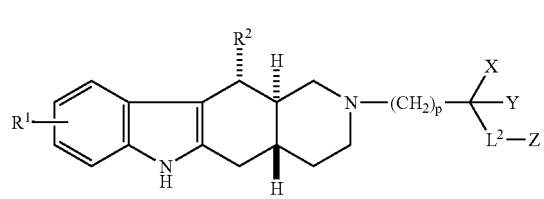

wherein p, $R^1$, $R^2$, $L^2$, X, Y and Z have the meanings and preferred groupings provided above.

In a particularly preferred embodiment, X and Y are combined to form a 3-, 4-, 5-, 6- or 7-membered ring containing from 0 to 2 heteroatoms selected from O, N and S, $L^2$ is a bond and Z is —$CO_2R^1$ or —$CO_2NR^{15}R^{16}$.

In another particularly preferred embodiment, X and Y are combined to form a 3-, 4-, 5-, 6- or 7-membered ring containing from 0 to 2 heteroatoms selected from O, N and S and $R^1$ is independently halogen, $(C_1-C_4)$alkyl, fluoro$(C_1-C_4)$alkyl, —$OR^5$, fluoro$(C_1-C_4)$alkoxy, —$CO_2R^5$, —$S(O)_mNR^5R^6$, —$S(O)_mR^5$ or —CN.

In another particularly preferred embodiment embodiment, X and Y are combined to form a 3-, 4-, 5-, 6- or 7-membered ring containing from 0 to 2 heteroatoms selected from O, N and S and $R^2$ is $(C_1-C_4)$alkyl or aryl.

In another particularly preferred embodiment embodiment, X and Y are combined to form a 3-, 4-, 5-, 6- or 7-membered ring containing from 0 to 2 heteroatoms selected from O, N and S, $R^1$ is independently halogen, $(C_1-C_4)$alkyl, fluoro$(C_1-C_4)$alkyl, —$OR^5$, fluoro$(C_1-C_4)$ alkoxy, —$CO_2R^5$, —$S(O)_mNR^5R^6$, —$S(O)_mR^5$ or —CN and $R^2$ is $(C_1-C_4)$alkyl or aryl.

In another particularly preferred embodiment $R^1$ is independently halogen, $(C_1-C_4)$alkyl, fluoro$(C_1-C_4)$alkyl, —$OR^5$, fluoro$(C_1-C_4)$alkoxy, —$CO_2R^5$, —$S(O)_mNR^5R^6$, —$S(O)_mR^5$ or —CN and $R^2$ is $(C_1-C_4)$alkyl or aryl.

In another particularly preferred embodiment embodiment, $R^1$ is independently halogen, $(C_1-C_4)$alkyl, fluoro$(C_1-C_4)$alkyl, —$OR^5$, fluoro$(C_1-C_4)$alkoxy, —$CO_2R^5$, —$S(O)_mNR^5R^6$, —$S(O)_mR^5$ or —CN, $L^2$ is a bond and Z is —$CO_2R^{15}$ or —$CO_2NR^{15}R^{16}$.

In another particularly preferred embodiment embodiment, $R^2$ is $(C_1-C_4)$alkyl or aryl, $L^2$ is a bond and Z is —$CO^2R^{15}$ or —$CO_2NR^{15}R^{16}$.

In another particularly preferred embodiment embodiment, $R^1$ is independently halogen, $(C_1-C_4)$alkyl, fluoro$(C_1-C_4)$alkyl, —$OR^5$, fluoro$(C_1-C_4)$alkoxy, —$CO_2R^5$, —$S(O)_mNR^5R^6$, —$S(O)_mR^5$ or —CN, $R^2$ is $(C_1-C_4)$alkyl or aryl, $L^2$ is a bond and Z is —$CO_2R^{15}$ or —$CO_2NR^{15}R^{16}$.

In a particular embodiment, the present invention provides the following compounds:

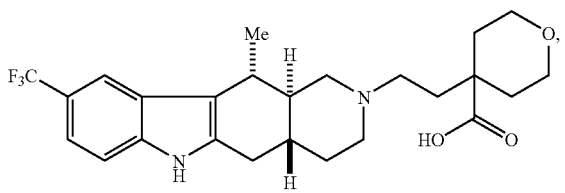

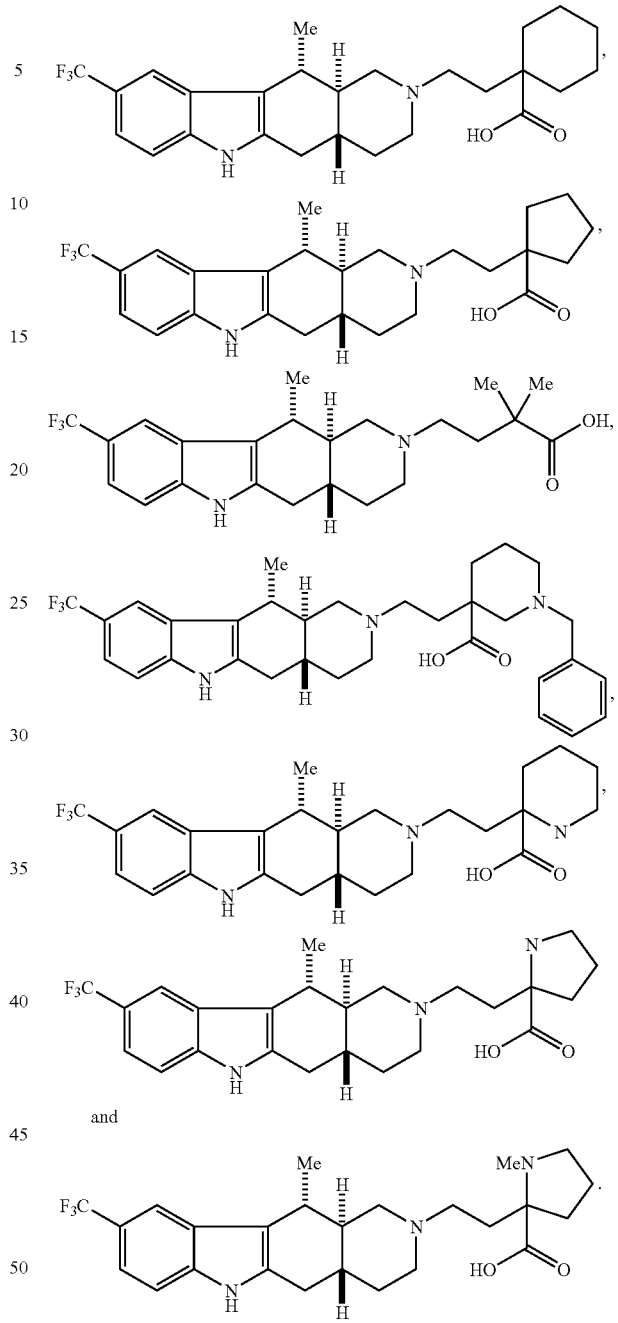

and

In further particular embodiments, the present invention provides pharmaceutically acceptable salts of the above compounds. For example, in a certain embodiment the present invention provides benzenesulfonic acid salts of the above compounds.

Compositions

In another aspect, the present invention provides pharmaceutical compositions comprising one or more compounds of the invention in combination with a diagnostically or pharmaceutically acceptable carrier or excipient. The subject compositions are useful for treating or preventing conditions and disorders mediated by MCHR, such as obesity and eating disorders, e.g., anorexia nervosa. The compounds of the present invention can be prepared and administered in a wide variety of oral and parenteral dosage forms. Thus, the compounds of the present invention can be administered by injection, for example, intravenously, intramuscularly, intracutaneously, subcutaneously, intraduodenally or intraperitoneally. Also, the compounds described herein can be administered by inhalation, for example, intranasally. Additionally, the compounds of the present invention can be administered transdermally. Other routes of administration are also contemplated for use with the compounds of the present invention, including depot administration and rectal administration.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from about 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

In therapeutic use for the treatment or prevention of conditions and disorders associated with MCHR, the compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The compositions may be advantageously combined and/or used in combination with agents useful in the treatment and/or prevention of obesity and eating disorders and pathologies associated therewith (e.g., cardiovascular disease and hypertension). In many instances, administration of the subject compounds or compositions in conjunction with these alternative agents enhances the efficacy of such agents. Accordingly, in some instances, the present compounds, when combined or administered in combination with, e.g., anti-obesity agents, can be used in dosages which are less than the expected amounts when used alone, or less than the calculated amounts for combination therapy.

Suitable agents for combination therapy include those that are currently commercially available and those that are in development or will be developed. Exemplary agents useful in the treatment of obesity include $\beta_3$ adrenergic receptor agonists, leptin or derivatives thereof and neuropeptide Y antagonists. Exemplary agents useful in the treatment of anxiety and/or mood disorders include benzodiazepines, e.g., alprazolam, chlordiazepoxide, clonazepam, clorazepate, diazepam, lorazepam, oxazepam, and the like; heterocyclic antidepressants, e.g, amitriptyline, nortriptyline, imipramine, desipramine, doxepin, trimipramine, clomipramine, protryptyline, amoxapine and maprotiline; monoamine oxidase inhibitors (MAOIs), e.g., phenelzine and tranylcypromine; serotonin reuptake inhibitors (SRIs); selective serotonin reuptake inhibitors (SSRIs), e.g., fluoxetine, fluvoxamine, paroxetine and sertraline; serotonergic-noradrenergic antidepressants, e.g., venlafaxine; 5-HT2 antagonists, e.g., trazadone, nefazodone and mirtazapine; and catecholaminergic antidepressants, e.g., buprorion.

Methods of Use

In yet another aspect, the present invention provides methods of using one or more compounds of the invention to treat or prevent a condition or disorder associated with eating behavior, energy homeostasis or anxiety. Exemplary conditions and disorders associated with eating behavior, energy homeostasis and anxiety include eating disorders, such as anorexia nervosa and bulimia, obesity, anxiety disorders, e.g., generalized anxiety disorder, panic attacks, panic disorder and obsessive-compulsive disorder (OCD), and mood disorders, e.g., depression and bipolar disorders. Methods of using a compound of the invention to treat or prevent a condition or disorder associated with eating behavior include methods of modifying eating behavior or food intake, for example, stimulating or suppressing eating behavior or increasing or decreasing food intake. The methods comprise administering to a subject in need thereof a therapeutically effective amount of a compound of the invention.

In another aspect, the present invention provides methods of using a compound of the invention to treat or prevent a condition or disorder mediated by MCHR. The methods comprise administering to a subject in need thereof a therapeutically effective amount of a compound of the invention.

In still another aspect, the present invention provides methods of using a compound of the invention to modulate MCHR. The methods comprise contacting a cell with a compound of the invention.

The compounds of the invention may also modulate G-protein coupled receptors related to MCHR, e.g., MCHR2 (see International Publication Nos. WO 00/49046 and WO 01/07606).

Preparation of the Compounds

The present invention provides a process for the preparation of a compound of formula I.

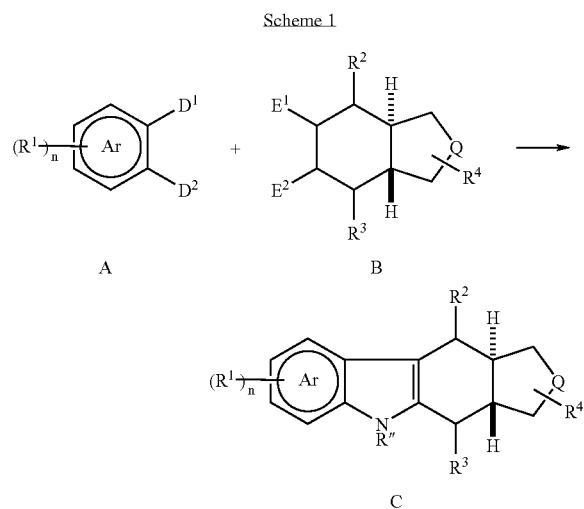

Scheme 1

A general synthetic route is depicted in Scheme 1, which outlines the condensation of substituted aryl moiety A, with a bicyclic structure B to produce a compound of formula C, wherein the variables are as defined as above. In formula A, $D^1$ is hydrogen, halogen, —C(O)$R^7$, —CO$_2R^8$ or —C(O)NR$^5R^6$, wherein $R^5$, $R^6$, $R^7$ and $R^8$ are defined as above, and $D^2$ is a bond, —N(R")—, —N(protecting group)-, —S— or —O—, wherein R" is defined as above and protecting group is an amino protecting group. Conventional amino protecting groups consist of known groups which are used to protectively block an amino group during the synthesis procedures described herein. These conventional blocking groups are readily removable, i.e., they can be removed, if desired, by procedures which will not cause cleavage or other disruption of the remaining portions of the molecule. Suitable protecting groups for the compounds of the present invention will be recognized from the present application taking into account the level of skill in the art, and with reference to standard textbooks, such as Greene, T. W. et al,. *Protective Groups in Organic Synthesis*, Wiley, New York (1991).

In formula B, $E^1$ is hydrogen, —C(O)$R^7$, —CO$_2R^8$ or —C(O)NR$^5R^6$, wherein $R^5$, $R^6$, $R^7$ and $R^8$ are defined as above, and $E^2$ is =O or —NR$^5R^6$, wherein $R^5$ and $R^6$ are defined as above. When a compound of formula A, wherein $D^1$ is hydrogen and $D^2$ is —N(R")— or —N(protecting group)-, —S—, or —O—, reacts with a compound of formula B, wherein $E^1$ is hydrogen and $E^2$ is =O or a protected version thereof (e.g., an acetal), under the typical Fisher indolization conditions, a compound of formula C is produced.

One of skill in the art will understand that the synthesis provided above can be modified to use different starting materials and alternate reagents to accomplish the desired transformations. For example, a compound of formula A, wherein $D^1$ is a leaving group such as Cl, Br, I or toluenesulfonate, can react with a compound of formula B, wherein $E^2$ is =O or a protected version thereof, via a palladium-catalyzed coupling reaction to produce a compound of formula C. Also, a compound of formula A, wherein $D^1$ is a leaving group and $D^2$ is a nitro group, can react with a compound of formula B, wherein $E^1$ is CO$_2$R and wherein $E^2$ is =O or a protected version thereof, to produce a compound of formula C. Accordingly, the synthesis and reagents described herein are all expressed as non-limiting embodiments.

Materials represented by formula A are available commercially (Aldrich Chemical), or can be obtained synthetically following literature procedures.

One way to prepare compounds represented by formula B is by the Robinson annulation process between a cyclic ketone and a substituted enone followed by saturation of the double bond. One of the skill in the art will readily appreciate that other methods are available. The relative stereochemistry and absolute stereochemistry can be controlled in the process. The individual forms of compounds of formula B, e.g., diastereomers and enantiomers, can be formed by stereocontrolled reactions, or may be separated, e.g., by chromatographic techniques (diastereomers) and by resolution (enantiomers).

Analysis of the Compounds

The activity of MCHR polypeptides can be assessed using a variety of in vitro and in vivo assays to determine functional, chemical and physical effects, e.g., measuring ligand binding (e.g., radioactive ligand binding), second messenger (e.g., cAMP, cGMP, IP$_3$, DAG, or Ca$^{2+}$) levels, ion flux, phosphorylation levels, transcription levels, neurotransmitter levels, and the like. Furthermore, such assays can be used to test for antagonists and agonists of MCHR. Screening assays may be used to identify modulators that can be used as therapeutic agents, e.g., antagonists of MCHR activity.

Modulators of MCHR activity can be tested using MCHR polypeptides as described above, either recombinant or naturally occurring (e.g., endogenous). The protein can be isolated, expressed in a cell, expressed in a membrane derived from a cell, expressed in tissue or in an animal, either recombinant or naturally occurring. For example, kidney cells, liver cells, colon cells, transformed cells, or membranes can be used. Modulation is tested using one of the in vitro or in vivo assays described herein. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Gene amplification can also be examined. Furthermore, ligand-binding domains of the protein of interest can be used in vitro in soluble or solid state reactions to assay for ligand binding.

Ligand binding to MCHR, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

MCHR-G-protein interactions can also be examined, by, for example, analysis of binding of the G-protein to MCHR or its release from MCHR can be examined. For example, in the absence of GTP, an activator will lead to the formation of a tight complex of a G protein (all three subunits) with MCHR. This complex can be detected in a variety of ways, as noted above. Such an assay can be modified to search for antagonists. In one embodiment, an activator is added to MCHR and G protein in the absence of GTP, allowed to form a tight complex, and then screened for antagonists by looking at dissociation of the MCHR-G protein complex. In the presence of GTP, release of the alpha subunit of the G protein from the other two G protein subunits serves as a criterion of activation.

An activated or inhibited G-protein will in turn alter the properties of downstream effectors such as proteins, enzymes and channels. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Activated MCHR becomes a substrate for kinases that phosphorylate the C-terminal tail of the receptor (and possibly other sites as well). Thus, activators will promote the transfer of $^{32}P$ from gamma-labeled ATP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors. For a general review of GPCR signal transduction and methods of assaying signal transduction, see, e.g., *Methods in Enzymology*, vols. 237 and 238 (1994) and volume 96 (1983); Bourne et al., *Nature* 10:349:117-27 (1991); Bourne et al., Nature 348:125-32 (1990); Pitcher et al., *Annu. Rev. Biochem.* 67:653-92 (1998).

Samples or assays that are treated with a potential MCHR antagonist or agonist are compared to control samples without the test compound, to examine the extent of modulation. Control samples (untreated with agonists or antagonist) are assigned a relative MCHR activity value of 100. Inhibition of MCHR is achieved when the MCHR activity value relative to the control is about 90%, optionally 50%, optionally 25-0%. Activation of MCHR is achieved when the MCHR activity value relative to the control is 110%, optionally 150%, 200-500%, or 1000-2000%.

Changes in ion flux may be assessed by determining changes in polarization (i.e., electrical potential) of the cell or membrane expressing MCHR. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336: 1575-1595 (1997)). Whole cell currents are conveniently determined using the standard methodology (see, e.g., Hamil et al., *PFlugers. Archiv.* 391:85 (1981). Other known assays include radiolabeled ion flux assays and fluorescence assays using voltage-sensitive dyes (see, e.g., Vestergarrd-Bogind et al., *J. Membrane Biol.* 88:67-75 (1988); Gonzales & Tsien, *Chem. Biol.* 4:269-277 (1997); Daniel et al., *J. Pharmacol. Meth.* 25:185-193 (1991); Holevinsky et al., *J. Membrane Biology* 137:59-70 (1994)). Generally, the compounds to be tested are present in the range from 1 pM to 100 mM.

The effects of the test compounds upon the function of the polypeptides can be measured by examining any of the parameters described above. Any suitable physiological change that affects MCHR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3 or cAMP.

Preferred assays for MCHR include cells that are loaded with ion- or voltage-sensitive dyes to report receptor activity. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion-sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as $G\alpha 15$ and $G\alpha 16$ can be used in the assay of choice (Willie et al., *Proc. Natl Acad. Sci. USA* 88:10049-10053 (1991)). Such promiscuous G-proteins allow coupling of a wide range of receptors to signal transduction pathways in heterologous cells.

Receptor activation typically initiates subsequent intracellular events, e.g., increases in second messengers such as IP3, which releases intracellular stores of calcium ions. Activation of some G-protein coupled receptors stimulates the formation of inositol triphosphate (IP3) through phospholipase C-mediated hydrolysis of phosphatidylinositol (Berridge & Irvine, *Nature* 312:315-21 (1984)). IP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting downstream effectors such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *Proc. Natl. Acad. Sci. U.S.A.* 88:9868-9872 (1991) and Dhallan et al., *Nature* 347:184-187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In one embodiment, changes in intracellular cAMP or cGMP can be measured using immunoassays. The method described in Offermanns & Simon, *J. Biol. Chem.* 270: 15175-15180 (1995) may be used to determine the level of cAMP. Also, the method described in Felley-Bosco et al., *Am. J. Resp. Cell and Mol. Biol.* 11:159-164 (1994) may be used to determine the level of cGMP. Further, an assay kit for measuring cAMP and/or cGMP is described in U.S. Pat. No. 4,115,538, herein incorporated by reference. In another embodiment, phosphatidyl inositol (PI) hydrolysis can be analyzed according to U.S. Pat. No. 5,436,128, herein incorporated by reference.

In another embodiment, transcription levels can be measured to assess the effects of a test compound on signal transduction. A host cell containing the protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using a reporter gene may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, *Nature Biotechnology* 15:961-964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant (or non-recombinant) cell line was prepared but which had not been modified by introduction of heterologous DNA. Any difference in the amount of transcription indicates that the test compound has in some manner altered the activity of the protein of interest.

The following examples are provided by way of illustration only and not by way of limitation. Those of skill in the art will readily recognize a variety of noncritical parameters that could be changed or modified to yield essentially similar results.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses). A single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM $NH_4OAc$ in acetonitrile/water as delivery solvent. Analytical HPLC analysis was conducted on a Hewlett-Packard Series 1050 system equipped with a C18 reverse phase column (4.6 mm×150 mm) manufactured by Shiseido Co., Japan. Gradient elution was performed using variable percentage of acetonitrile and water (each with 0.1% trifluoroacetic acid added) as a mobile phase. Optical purity analysis was also conducted on a Hewlett-Packard Series 1050 system equipped with a chiral HLPC column (ChiralPak AD, 4.6 mm×150 mm) purchased from Chiral Technology. Isopropanol (3%) and hexane (97%) containing 0.1% diethylamine was used as a mobile phase.

Example 1

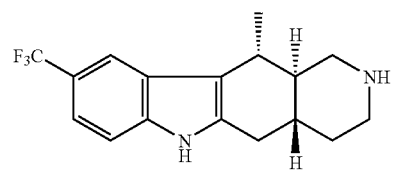

Compound 4 was prepared in 4 steps, as follows.

Step 1. Robinson Annulation. A mixture of N-benzyl-4-piperidone (500 g, 2.65 mol) and pyrrolidine (330 mL, d 0.852, 3.96 mol) in toluene (2 L) was heated at refluxing while water from elimination was removed with a Dean- Stark trap. After 8 h, 70 mL of water were collected, and the volume of collected water ceased to increase further. GC analysis revealed the presence of the starting N-benzyl-4-piperidone and product enamine. The solvent and excess pyrrolidine were evaporated under reduced pressure (vacuum, 60 torr; heating bath, 50° C.). The residue was dissolved in 500 mL of toluene, and evaporated again to give a dark oil (630 g).

The resulting enamine was dissolved in anhydrous dioxane (2 L) and filtered into a 5-L three-necked flask equipped with a mechanic stirrer, a condenser and an addition funnel. 3-Penten-2-one (333 g, 2.78 mol) was added to the reaction vessel in 20 min. The reaction mixture was heated to reflux for 25 h. After cooled to near r.t., NaOMe (6.7 g, 0.125 mol) was added and the mixture was heated to reflux for 6 h. A premixed solution of AcONa (200 g) in 400 mL water and glacial AcOH (400 mL) was added to the reaction mixture after cooling to near room temperature. The reaction mixture was heated to reflux for an additional 5 h. Approximately 1 L of solvent (and possibly pyrrolidine) was distilled out, the rest of the reaction mixture was cooled to r.t, brought to slightly basic (pH 8-9) with 2 N NaOH (2.5 L). After layer separation, aqueous phase was extracted with AcOEt (3 L). The organic extracts were combined, washed with brine, and filtered through a short silica gel plug to give a dark clear solution. The filtrate was concentrated under reduced pressure to a thick oil (670 g). This material was used in the resolution step directly.

Step 2. Resolution

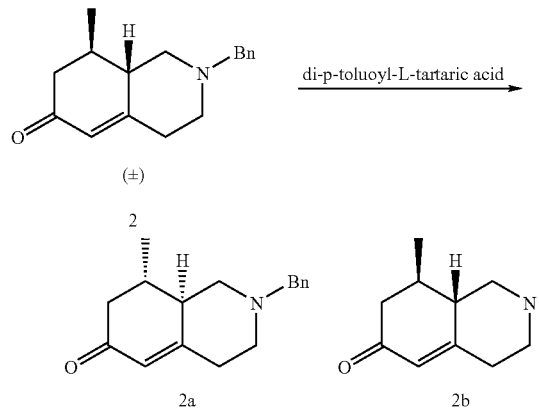

To a stirred hot solution of the racemic isoquinolinone free base (626 g, 2.45 mol) in 95% ethanol (800 mL) was added solution of di-O-p-toluoyl-L-tartaric acid (945 g, 2.45 mol) in hot ethanol (1500 mL). Precipitation of the less soluble diasteromeric salt occurred generally as soon of the mixing was completed. The mixture was heated in a hot water bath (80° C.) with gentle stirring for 1 h and allowed to cool to r.t. slowly (typically overnight). The precipitate was collected by filtration and rinsed wih cold 95% ethanol (800 mL). The solid (off-white) was triturated in hot 95% ethanol (1500 mL) and collected after cooling (typically after standing at r.t. overnight) by filtration and washed with cold ethanol. An off-white solid (340 g, ca. 98% ee) was obtained after two triturations.

Compound 2a was liberated from the salt by neutralization with NaOH and extraction with AcOEt.

Step 3. Hydrogenation

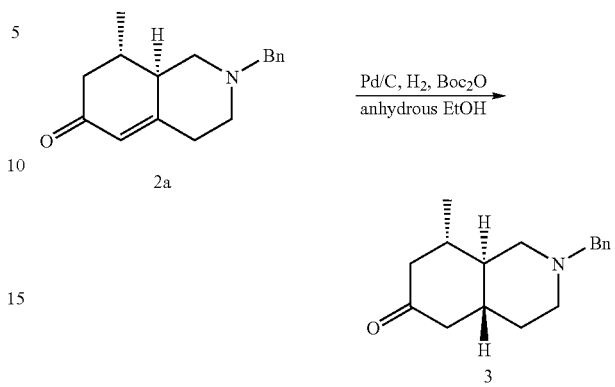

A flask for the Parr shaker hydrogenation apparatus was charged with the N-benzylisoqinolinone compound from previous step (120 g, 0.47 mol), 10% Pd/C (12 g, contains 50% water), di-t-butyl dicarbonate (133 g, 0.61 mol), and ethanol (1200 mL, 200 proof). The reactions took place under a hydrogen pressure of 60 psi. The hydrogen pressure dropped quickly in the first 2 h, frequent recharges were needed. The reaction was typically left to go undisturbed for 8 h or longer. No further $H_2$ consumption was observed. The reaction mixture was filtered through a Celite pad, rinsed with ethanol. Filtrate was concentrated to the product as a thick oil, which solidified on standing to give a white solid. This material was used in the next step without further purification.

Step 4. Fisher indole synthesis

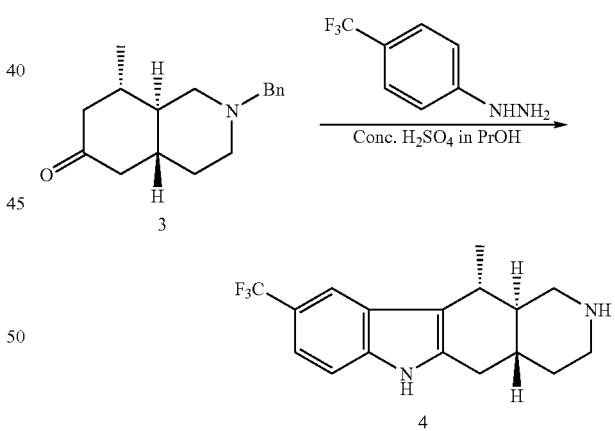

The solution of the N-Boc-isoquinolinone compound from previous step in propanol (200 mL) was placed in a pressure resistant vessel. Concentrated $H_2SO_4$ (13 mL) was added slowly. Gas release took place immediately and subsided after 45 min. 4-Trifluorophenylhydrazine (16.56 g, 94.0 mmol) was added. The mixture was stirred for 1 h at r.t followed by 3 h at refluxing or until gas evolution stopped. At this time, MS analysis indicted hydrozone as the major component of the reaction mixture. The reaction vessel was capped and heated at 90° C. for 36 h until the completion of reaction, as monitored by TLC (10: 1:0.1, $CH_2Cl_2$/MeOH/$NH_4OH$), and ES-MS in positive mode. At the completion of the reaction, the reaction mixture was poured to a stirred solution of 1 N NaOH (some precipitates were formed). The mixture was extracted with dichloromethane three times. The combined organic extracts were washed with water, dried over NaSO$_4$, filtered, and concentrated to give a solid. The residue was triturated with CH$_2$Cl$_2$. The solid was collected by filtration. The product could be purified by chromatography on silica gel column with a gradient elution of increasing polarity from 20:1:0.1 to 6:1:0.1 CH$_2$Cl$_2$/MeOH/NH$_4$OH to obtain compound 4 as the major product.
$^1$H NMR δ 11.2 (s, 1H), 7.80 (s, 1H), 7.43 (d, J=5.4 Hz, 1H), 7.28 (d, J=5.4 Hz, 1H), 3.40 (d, J=6.0 Hz, 1H), 3.01 (d, J=8.0 Hz, 1H), 2.75 (d, J=10 Hz, 1H), 2.60 (m, 2H), 2.40 (m, 2H), 1.82 (d, J=8 Hz, 1H), 1.56 (m, 1H), 1.38 (d, J=5.4 Hz, 3H), 1.25 (m, 2H). MS (ES): 309 [M+H]$^+$.

Example 2

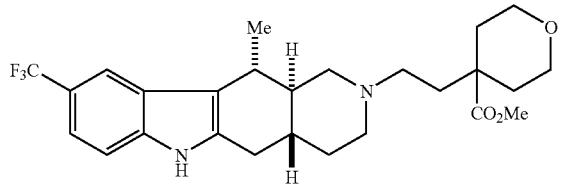

5

Compound 5 was synthesized in 3 steps, as follows.

Step 1. To a 500 mL flask containing iPr$_2$NH (16.82 mL, 120 mmol) in THF (200 mL) at −78° C. was added n-BuLi (48 mL, 2.5 M/hexanes, 120 mmol). After stirring for 30 min at −78° C., 4-Tetrahydro-pyran-4-carboxylic acid methyl ester (11.86 mL, 100 mmol) was added. After stirring for an additional 45 min, HMPA (10 mL) and allyl iodide (11.9 mL, 130 mmol) were added. The reaction was maintained for 20 min at the low temperature and allowed to warm up to r.t. The reaction mixture was poured into water and extracted with ether. The organic layer was washed with brine, dried with anhydrous Na$_2$SO$_4$, concentrated by rotary evaporation and purified by flash chromatography on silica gel with a gradient elution of 20-30% EtOAc/hexanes to yield a clear oil (16.6 g).

Step 2. The above alkylation product (15.26 g, 83 mmol) was stirred with NaIO$_4$ (39.0 g, 182 mmol) and OsO$_4$ (70 mg) in iPrOH (400 mL) and H$_2$O (400 mL) overnight. The reaction mixture was poured into water and extracted with EtOAc. The organic layer was separated, washed with brine, dried with anhydrous Na$_2$SO$_4$, concentrated by rotary evaporation and purified by flash chromatography on silica gel with a gradient elution of 40-70% EtOAc/hexanes to yield the product, 4-(2-oxo-ethyl)-tetrahydropyran-4-carboxylic acid methyl ester, as an oil (8.8 g).

Step 3. The above aldehyde (1.86 g, 10 mmol) was stirred with amine 4 (3.08 g, 10 mmol) and NaBH(OAc)$_3$ (8.48 g, 40 mmol) in ClCH$_2$CH$_2$Cl (50 mL) overnight. It was poured into a dilute aq. ammonia solution and extracted with EtOAc. The organic layer was separated, washed with brine, dried with anhydrous Na$_2$SO$_4$, concentrated by rotary evaporation and purified by flash chromatography on silica gel with a gradient elution of EtOAc, 10% MeOH/EtOAc, 10% MeOH/CH$_2$Cl$_2$, 20% MeOH/CH$_2$Cl$_2$ and 30% MeOH/CH$_2$Cl$_2$ to yield 5 as a solid (3.0 g). $^1$H NMR δ (DMSO, 400 MHz), 11.20 (s, 1H), 7.88 (s, 1H), 7.44 (d, J=8.5 Hz, 1H), 7.30 (d, J=8.5 Hz, 1H), 3.73 (m, 1H), 3.68 (s, 3H), 3.33 (m, 2H), 3.22 (m, 1H), 2.88 (m, 1H), 2.75 (m, 1H), 2.60 (m, 1H), 2.42 (m, 1H), 2.26 (m, 2H), 1.98 (m, 2H), 1.7-1.95 (m, 5H), 1.51 (m, 2H), 1.38 (d, J=6.5 Hz, 3H), 1.39 (m, 1H), 1.20 (m, 1H). MS (ES): 479 [M+H].

Example 3

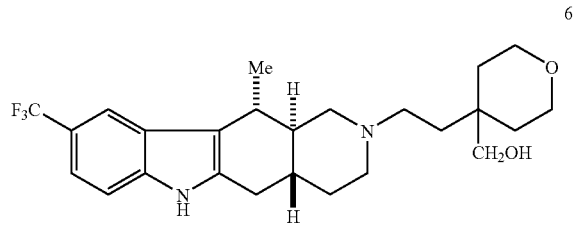

6

A sample of compound 5 (0.080 g, 0.17 mmol) in TBF (2 mL) was reduced with LiAlH$_4$ (0.400 mL, 1M/THF, 0.40 mmol) in TBF (2 mL). At the completion of the reduction, the reaction was quenched with an aqueous solution of 10% Na$_2$SO$_4$. The precipitate was removed by filtration, and the organic filtrate was washed with brine, dried with anhydrous Na$_2$SO$_4$, concentrated by rotary evaporation. Purification by flash chromatography on silica gel with a gradient elution of 5-30% MeOH/CH$_2$Cl$_2$ to yield 6 as a white solid (0.065 g). $^1$H NMR δ (DMSO, 400 MHz), 11.22 (s, 1H), 7.79 (s, 1H), 7.44 (d, J=8.5 Hz, 1H), 7.29 (d, J=8.5 Hz, 1 H), 5.35 (s, 1H), 3.56 (m, 4H), 3.31 (m, 3H), 3.02 (m, 1H), 2.74 (m, 1H), 2.62 (m, 1H), 2.43 (m, 3H), 1.95 (m, 1H), 1.86 (m, 1H), 1.75 (m, 1H), 1.60 (m, 2H), 1.25-1.5 (m, 10H). MS (ES): 451 [M+H].

Example 4

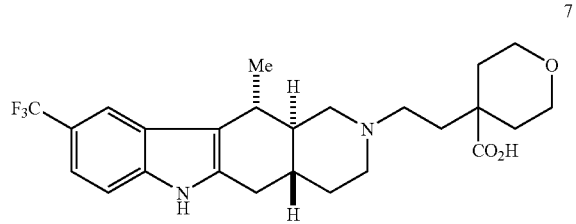

7

A mixture of ester 5 (0.80 g, 1.7 mmol) and LiOH.H$_2$O (0.80 g, 19 mmol) in dioxane (10 mL) and water (5 mL) was heated at refluxing for 7 h. The reaction mixture was cooled. On acidification with HOAc (to pH ca. 5) white precipitate was formed. The solid was collected by filtration, rinsed with water and finally with ether to yield the compound 7 as white solid (0.50 g). $^1$H NMR δ (DMSO, 500 MHz), 11.21 (s, 1H), 7.79 (s, 1H), 7.44 (d, J=8.5 Hz, 1H), 7.29 (d, J=8.5 Hz, 1 H), 3.71 (m, 2H), 3.31 (m, 2H), 2.97 (m, 1H), 2.75 (m, 1H), 2.62 (m, 1H), 2.44 (m, 4 H), 1.6-2.05 (m, 8H), 1.2-1.5 (m, 8H). MS (ES): 465 [M+H].

Example 5

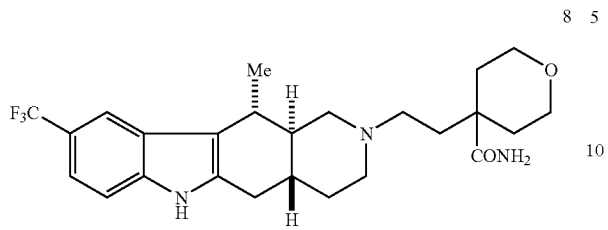

To a mixture of acid 7 (1.86 g, 4 mmol) in CH₂Cl₂ (60 mL) with 4 drops of DMF was added oxalyl chloride (17 mL, 2M in CH₂Cl₂, 34 mmol). After stirring at r.t for 1 h, the mixture was concentrated and pumped under high vacuum to obtain a solid. To this solid was added sat. solution of NH₄OH in CH₂Cl₂ (60 mL). The mixture was stirred overnight and directly loaded onto a chromatographic column with a gradient elution of 10-20% MeOH/CH₂Cl₂ with increasing percentage (0-10%) of NH₄OH added to yield compound 8 as a white solid (1.674 g). $^1$H NMR δ (DMSO, 400 MHz), 11.28 (s, 1H), 7.80 (s, 1H), 7.45 (d, J=8.5 Hz, 1H), 7.29 (d, J=8.5 Hz, 1H), 7.00 (s, br, 2H), 3.67 (m, 2H), 3.38 (m, 5H), 2.6-3.0 (m, 3H), 2.43 (m, 1H), 2.20 (m, 1H), 1.99 (m, 3H), 1.6-1.9 (m, 4H), 1.35-1.5 (m, 7H). MS (ES): 464 [M+H].

Example 6

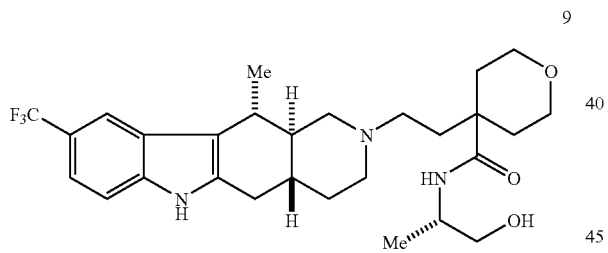

To a mixture of acid 7 (0.120 g, 0.256 mmol), DMF (2 drops) in CH₂Cl₂ (2 mL) was added (COCl)₂ (1.2 mL, 2M/CH₂Cl₂, 2.4 mmol). When the gas release ceased, the mixture was placed under high vacuum to obtain a solid. This solid was resuspended in CH₂Cl₂ (2 mL), to it was added (S)(+) 2-amino-1-propanol (0.100 mL, 1.7 mmol) and NEt₃ (0.140 mL, 1 mmol). After 1 h stirring at r.t., the mixture was poured into saturated solution of NaHCO₃ and extracted with EtOAc. The organic layer was separated, washed with brine, dried with anhydrous Na₂SO₄, concentrated by rotary evaporation and purified by flash chromatography on silica gel with a gradient elution of 10-20% MeOH/CH₂Cl₂ with 0-10% NH₄OH added to yield compound 9 as a white solid (0.098 g). $^1$H NMR δ (DMSO, 400 MHz), 11.22 (s, 1H), 7.79 (s, 1H), 7.44 (d, J=8.5 Hz, 1H), 7.29 (m, 2H), 4.70 (s, 1H), 3.92 (m, 1H), 3.66 (m, 2H), 3.34 (m, 6H), 2.90 (m, 1H), 2.75 (m, 1H), 2.60 (m, 1H), 2.40 (m, 1H), 2.25 (m, 2H), 2.20 (m, 3H), 1.84 (m, 1H), 1.72 (m, 3H), 1.41 (m, 7H), 1.07 (d, J=6.6 Hz, 3H). MS (ES): 522 [M+H].

Example 7

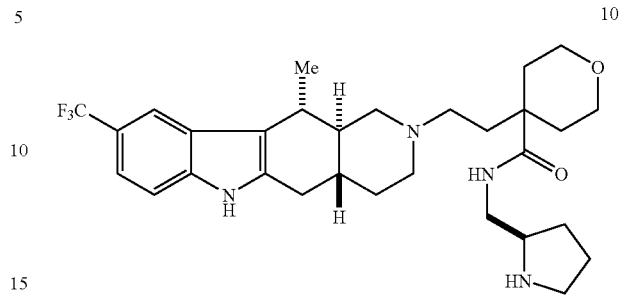

To a mixture of acid 7 (0.075 g, 0.16 mmol), DMF (2 drops) in CH₂Cl₂ (2 mL) was added (COCl)₂ (0.8 mL, 2 M/CH₂Cl₂, 1.6 mmol). When the gas release ceased, the mixture was placed under high vacuum to obtain a solid. To this solid was added CH₂Cl₂ (2 mL), (S)(+) 2-(aminomethyl)-pyrrolidine (0.20 mL, 1.87 mmol) and NEt₃ (0.170 mL, 1.2 mmol). The mixture was stirred for 1 h at r.t., poured into sat. NaHCO₃ and extracted with EtOAc. The organic layer was separated, washed with brine, dried with anhydrous Na₂SO₄, concentrated by rotary evaporation and purified by flash chromatography on silica gel with a gradient elution of 20-40% MeOH/CH₂Cl₂ in 0-10% NH₄OH to yield compound 10 as a yellowish solid (0.053 g). $^1$H NMR δ (DMSO, 400 MHz), 11.21 (s, 1H), 7.78 (s, 1H), 7.58 (m, 1H), 7.44 (d, J=8.5 Hz, 1H), 7.28 (d, J=8.5 Hz, 1H), 3.67 (m, 2H), 3.1-3.5 (m, 8H), 2.75-2.9 (m, 4H), 2.6 (m, 1H), 2.38 (m, 1H), 2.22 (m, 2H), 2.01 (m, 2H), 1.6-1.9 (m, 8H), 1.4 (m, 7H), 1.47 (m, 1H). MS (ES): 547 [M+H].

Example 8

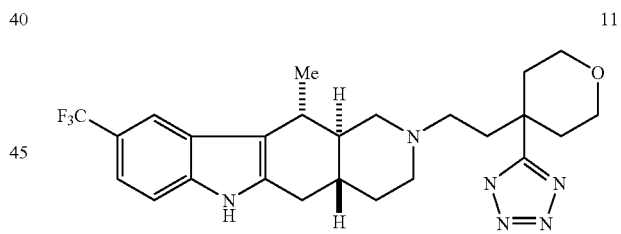

A mixture of amide 8 (0.695 g, 1.50 mmol) and POCl₃ (0.42 mL, 4.5 mmol) in anhydrous pyridine (14 mL) was heated to 120° C. in a sealed vessel for 2 h. It was cooled to r.t., poured into saturated NaHCO₃ solution and extracted with EtOAc. The organic layer was separated, washed with brine, dried with anhydrous Na₂SO₄, concentrated by rotary evaporation and purified by flash chromatography on silica gel with a gradient elution of 5-30% MeOH/CH₂Cl₂ to yield the corresponding nitrile as a yellowish solid (0.400 g).

The above nitrile was heated with Bu₃SnN₃ (0.74 mL, 2.7 mmol) in toluene (3 mL) at 120° C. in a sealed vessel for 2 days. At the completion of the reaction, the reaction mixture was cooled to r.t., acidified with 1M HCl in ether and purified by flash chromatography on silica gel with a gradient elution of 20-40% MeOH/CH₂Cl₂ in 0-10% NH₄OH to yield compound 11 as a yellowish solid (0.196 g).

$^1$H NMR δ (DMSO, 400 MHz), 11.26 (s, 1H), 7.79 (s, 1H), 7.44 (d, J=8.5 Hz, 1H), 7.30 (d, J=8.5 Hz, 1H), 3.37 (m,

3H), 3.14 (m, 4H), 3.14 (m, 1H), 2.77 (m, 1H), 2.64 (m, 3H), 2.43 (m, 2H), 2.25 (m, 3H), 2.01 (m, 2H), 1.91 (m, 1H), 1.76 (m, 2H), 1.55 (m, 1H), 1.35-1.5 (m, 4H). MS (ES): 489 [M+H].

J=8.5 Hz, 1H), 7.28 (dd, J=8.5, 1.4 Hz, 1H), 3.78 (d, J=11.6 Hz, 1H), 3.56 (d, J=11.6 Hz, 1H), 3.10 (td, J=12.2, 5.0 Hz, 1H), 2.94 (m, 2H), 2.81 (d, J=14.4 Hz, 2H), 2.65 (t, J=5.7 Hz, 1H), 2.40 (dd, J=15.7, 9.8 Hz, 1H), 2.05-1.90 (m, 5H), 1.80-1.65 (m, 3H), 1.54-1.39 (m, 3H), 1.39 (d, J=6.6 Hz, 3H), 1.38-1.22 (m, 5H). MS (ES): 463 [M+H].

Example 9

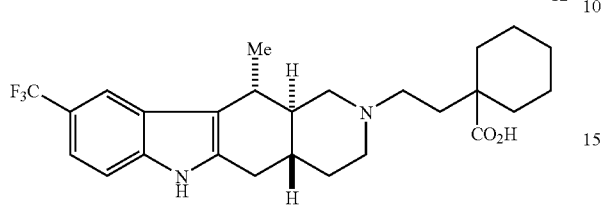

Compound 12 was prepared following the procedures detailed in Example 4, substituting 4-(2-oxo-ethyl)-tetrahydro-pyran-4-carboxylic acid methyl ester with cyclohexane carboxylic acid methyl ester. $^1$H NMR δ (d$_6$-DMSO) 12.47 (bs, 1H), 11.31 (s, 1H), 10.46 (bs, 1H), 7.78 (s, 1H), 7.44 (d, Example 10

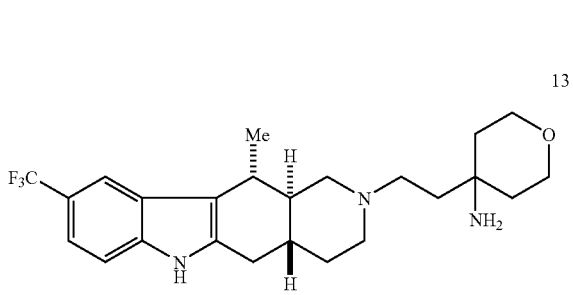

Compound 13 was synthesized in 5 steps according to the following scheme.

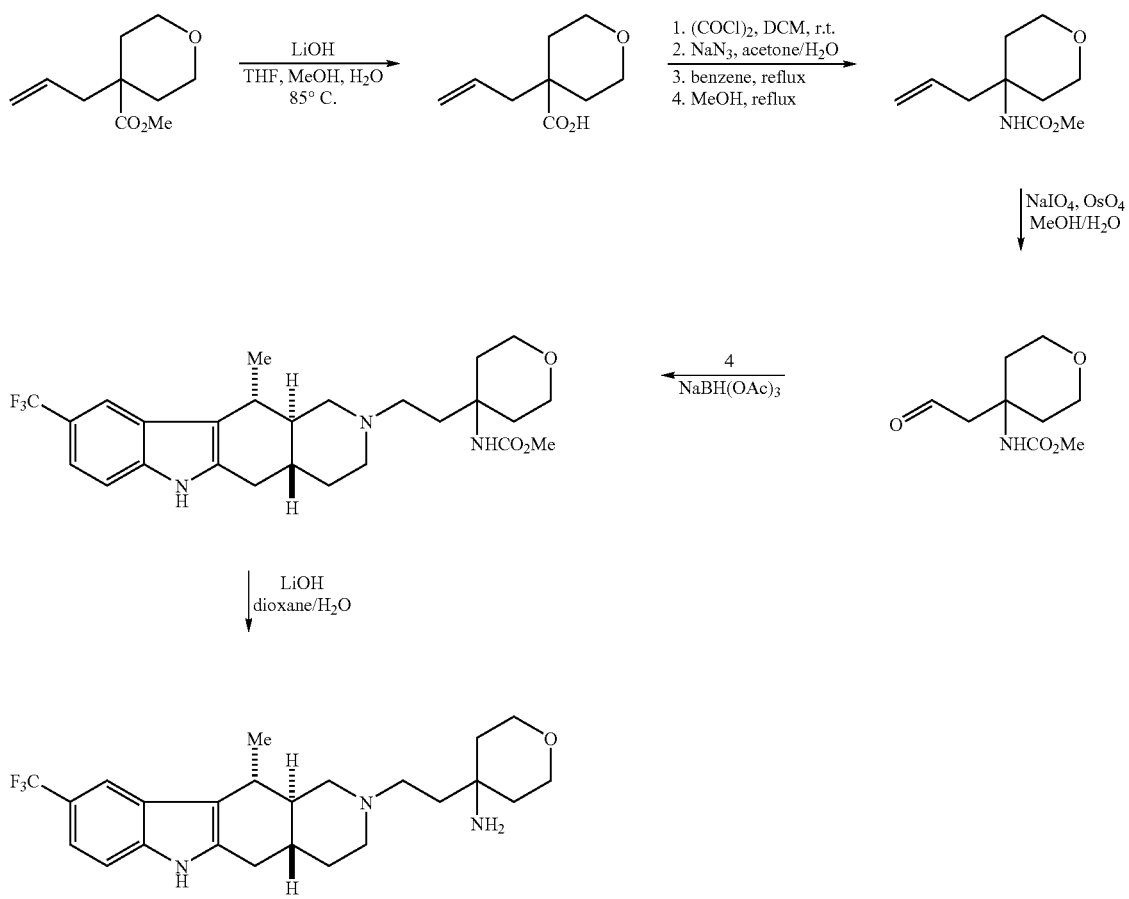

Step 1. A mixture of 4-allyl-tetrahydropyran carboxylic acid methyl ester (15.7 g, 92.4 mmol) and LiOH.H$_2$O (29 g, 688 mmol) in THF (110 mL), MeOH (110 mL) and water (5 mL) was heated to 85° C. in a sealed vessel overnight. Upon cooling to r.t., it was extracted with EtOAc, washed with water, dried with anhydrous Na$_2$SO$_4$ and concentrated by rotary evaporation to yield the corresponding carboxylic acid as a white solid (12.82 g).

Step 2. To a mixture of the above acid (12.82 g, 75.4 mmol), DMF (4 drops) in CH$_2$Cl$_2$ (300 mL) was added (COCl)$_2$ (75.4 mL, 2 M in CH$_2$Cl$_2$, 150.8 mmol). When the gas release ceased, the mixture was placed on a rotary evaporator. The obtained acid chloride (in 150 mL of dry acetone) was added to NaN$_3$ (48.75 g, 0.75 mol, in 300 mL of water) at 0° C. over 30 min. After stirring 2 h at r.t., the mixture was poured into ice-water and extracted with ether. The organic layer was separated, washed with brine, dried over anhydrous Na$_2$SO$_4$ and concentrated by rotary evaporation. The obtained azide was dissolved in 100 mL of benzene and added slowly to 100 mL of refluxing benzene. The reflux continued for another 40 min at which time no more gas was released. Benzene was distilled off and 120 mL of MeOH was added to the mixture. The mixture was heated at refluxing for 36 h, cooled to r.t. and was directly chromatographed using 40% EtOAc/hexanes as eluent. The carbamate product was obtained as a white solid (14.15 g).

Step 3. The obtained carbamate (0.498 g, 2.5 mmol) was stirred with NaIO$_4$ (1.18 g, 5.5 mmol) and OsO$_4$ (30 mg) in MeOH (5 mL) and H$_2$O (5 mL) for 15 min. The mixture was directly loaded onto a column for chromatography with a gradient elution of 70-90% EtOAc/hexanes as the eluent to yield the aldehyde product as an oil (0.48 g).

Step 4. The above aldehyde (0.38 g, 1.9 mmol) was stirred with amine 4 (0.587 g, 1.9 mmol) and NaBH(OAc)$_3$ (1.61 g, 7.6 mmol) in ClCH$_2$CH$_2$Cl (15 mL) overnight. The reaction mixture was poured into a dilute aqueous ammonia solution and extracted with EtOAc. The organic layer was separated, washed with brine, dried with anhydrous Na$_2$SO$_4$, concentrated by rotary evaporation and purified by flash chromatography on silica gel with a gradient elution of 20-40% MeOH/CH$_2$Cl$_2$ with 0-10% NH$_4$OH added to yield the coupled product as a solid (0.618 g).

Step 5. A mixture of the obtained product (0.618 g, 1.25 mmol) and LiOH.H$_2$O (3.0 g, 71.5 mmol) in dioxane (20 mL) and water (10 mL) was heated to 120° C. in a sealed vessel for 8 h. Upon cooling to r.t., it was poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 20-40% MeOH/CH$_2$Cl$_2$ with 0-10% NH$_4$OH added to yield compound 13 as a yellowish solid (0.268 g). MS (ES): 436 [M+H].

Example 11

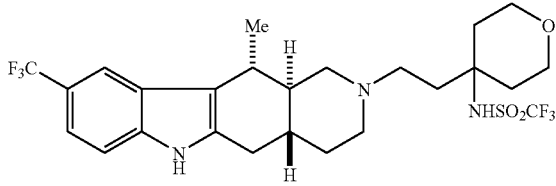

14

To a mixture of amine 13 (0.096 g, 0.22 mmol) and NEt$_3$ (0.084 mL, 0.6 mmol) in CH$_2$Cl$_2$ (1.5 mL) was added trifluoromethanesulfonyl anhydride (0.067 mL, 0.40 mmol) at 0 C. After 20 min, it was poured into saturated NaHCO$_3$ solution and extracted with EtOAc. The organic layer was separated, washed with brine, dried with anhydrous Na$_2$SO$_4$, concentrated by rotary evaporation and purified by flash chromatography on silica gel with a gradient elution of 5-20% MeOH/CH$_2$Cl$_2$ to yield compound 14 as a yellowish solid (0.077 g). $^1$H NMR δ (DMSO, 400 MHz), 11.27 (s, 1H), 7.81 (s, 1H), 7.46 (d, J=8.5 Hz, 1H), 7.30 (d, J=8.5 Hz, 1H), 3.5-4.1 (m, 10H), 2.95 (m, 2H), 2.83 (m, 1H), 2.80 (m, 1H), 2.69 (m, 1H), 2.35 (m, 2H), 2.00 (m, 5H), 1.73 (m, 3H), 1.40 (d, J=6.5 Hz, 3H). MS (ES): 568 [M+H].

Example 12

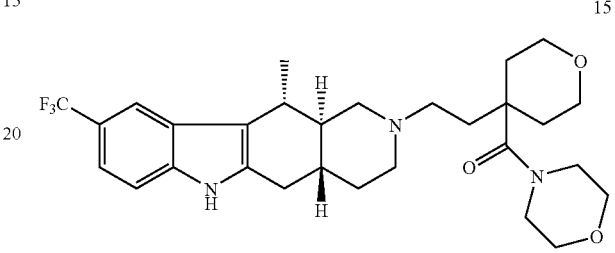

15

To a mixture of acid 7 (0.070 g, 0.15 mmol), DMF (2 drops) and DCM (2 mL) was added (COCl)$_2$ (0.6 mL, 2 M/DCM, 1.2 mmol). When the gas release ceased, solvents were evaporated to obtain a solid. To this solid was added DCM (2 mL), morpholine (0.2 mL, 2.3 mmol) and TEA (0.15 mL, 1.1 mmol). The mixture was stirred at r.t. for 1 h, poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel eluted with 20% MeOH/DCM to yield 15 as a yellowish solid (0.080 g). $^1$H NMR δ (DMSO, 500 MHz): 11.20 (s, 1H), 7.79 (s, 1H), 7.44 (d, J=8.5 Hz, 1H), 7.28 (d, J=8.5 Hz, 1H), 3.69 (m, 2H), 3.58 (m, 8H), 3.44 (m, 2H), 3.32 (m, 2H), 3.24 (m, 1H), 2.90 (m, 1H), 2.74 (m, 1H), 2.42 (m, 1H), 2.23 (m, 2H), 2.08 (m, 2H), 1.86 (m, 4H), 1.68 (m, 1H), 1.52 (m, 2H), 1.29 (m, 2H), 1.27 (d, J=8.5 Hz, 3H). MS (ES): 534 [M+H].

Example 13

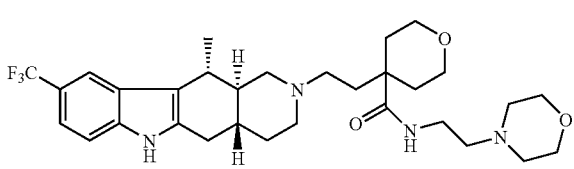

16

A mixture of acid 7 (0.306 g, 0.66 mmol), 4-(2-aminoethyl)morpholine (0.375 mL, 2.64 mmol), EDC.HCl (0.381 g, 1.98 mmol), HOBt (0.267 g, 1.98 mmol), NMP (0.44 mL, 4 mmol), DCM (5 mL) and DMF (5 mL) was stirred at r.t. for 3 h. The mixture was poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 10-20% MeOH/DCM containing 1-3% NH$_4$OH to yield 16 as a white solid (0.310 g). MS (ES): 577 [M+H].

Example 14

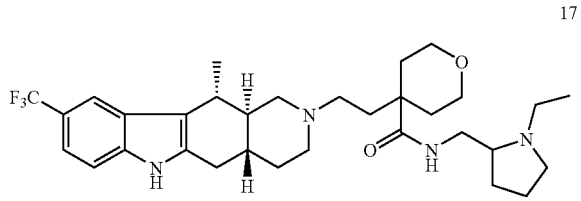

17

A mixture of acid 7 (0.102 g, 0.22 mmol), 2-aminoethyl-1-ethylpyrrolidine (0.128 g, 1 mmol), EDC.HCl (0.127 g, 0.66 mmol), HOBt (0.089 g, 0.66 mmol), NMP (0.22 mL, 2 mmol), DCM (1.5 mL) and DMF (1.5 mL) was stirred at r.t. for 8 h. The mixture was poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 10-25% MeOH/DCM containing 1-3% NH$_4$OH to yield 17 as a white solid (0.095 g). $^1$H NMR δ (DMSO, 500 MHz): 11.19 (s, 1H), 7.78 (s, 1H), 7.60 (t, J=5.5 Hz, 1H), 7.43 (d, J=8.5 Hz, 1H), 7.28 (d, J=8.5 Hz, 1H), 3.66 (m, 2H), 3.30 (m, 1H), 3.21 (m, 1H), 3.02 (m, 1H), 2.60-3.0 (m, 3H), 2.73 (m, 1H), 2.60 (m, 1H), 2.47 (m, 1H), 2.40 (m, 1H), 2.20 (m, 3H), 2.10 (m, 1H), 2.00 (m, 2H), 1.79-1.95 (m, 4H), 1.5-1.7 (m, 6H), 1.40 (m, 5H), 1.37 (d, J=6.5 Hz, 3H), 1.06 (m, 1H), 1.04 (t, J=7.5 Hz, 3H). MS (ES): 575 [M+H].

Example 15

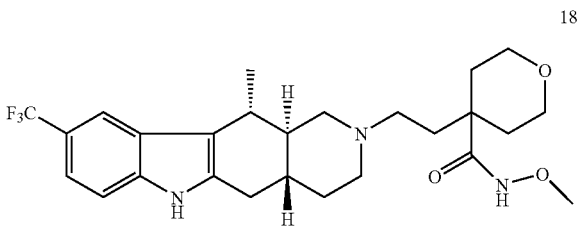

18

To a mixture of acid 7 (0.325 g, 0.7 mmol), DMF (2 drops) and DCM (8 mL) was added (COCl)$_2$ (3.6 mL, 2 M in DCM, 7.2 mmol). When the gas release ceased, the mixture was placed under high vacuum to obtain a solid. To this solid was added DCM (8 mL), MeONH$_2$.HCl (0.800 g, 9.6 mmol) and TEA (0.60 mL, 4.3 mmol). The mixture was stirred at r.t. for 1 h, poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel eluted with a gradient elution of 20-40% MeOH/DCM mixed with 0-10% NH$_4$OH to yield 18 as an off-white solid (0.24 g). $^1$H NMR δ (DMSO, 500 MHz): 11.20 (s, 1H), 11.15 (s, 1H), 7.79 (s, 1H), 7.43 (d, J=8.5 Hz, 1H), 7.28 (d, J=8.5 Hz, 1H), 3.68 (m, 2H), 3.63 (s, 3H), 3.35 (m, 2H), 3.23 (m, 1H), 2.89 (m, 1H), 2.75 (m, 1H), 2.60 (m, 1H), 2.40 (m, 1H), 2.26 (m, 2H), 1.87-2.0 (m, 3H), 1.81 (m, 1H), 1.69 (m, 3H), 1.43 (m, 4H), 1.38 (d, J=6.5 Hz, 3H), 1.19 (m, 1H). MS (ES): 494 [M+H].

Example 16

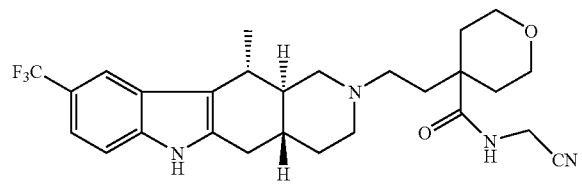

19

To a mixture of acid 7 (0.060 g, 0.13 mmol), DMF (1 drop) and DCM (2 mL) was added (COCl)$_2$ (0.6 mL, 2 M in DCM, 1.2 mmol). When the gas release ceased, the mixture was placed under high vacuum to obtain a solid. To this solid was added DCM (2 mL), NH$_2$CH$_2$CN (0.200 g, 3.6 mmol) and TEA (0.15 mL, 1.07 mmol). After stirring at r.t. for 1 h, the mixture was poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel eluted with a gradient elution of 20-40% MeOH/DCM mixed with 0-8% NH$_4$OH to yield 19 as a white solid (0.028 g). $^1$H NMR δ (DMSO, 500 MHz): 11.20 (s, 1H), 8.50 (s, 1H), 7.78 (s, 1H), 7.43 (d, J=8.5 Hz, 1H), 7.28 (d, J=8.5 Hz, 1H), 4.15 (d, J=5.5 Hz, 2H), 3.69 (m, 2H), 3.33 (s, 3H), 3.23 (m, 1), 2.88 (m, 1H), 2.75 (m, 1H), 2.60 (m, 1H), 2.40 (m, 1H), 2.22 (m, 2H), 2.00 (m, 2H), 1.6-1.95 (m, 4H), 1.50 (m, 2H), 1.39 (m, 2H), 1.37 (d, J=6.5 Hz, 3H), 1.28 (m, 1H). MS (ES): 503 [M+H].

Example 17

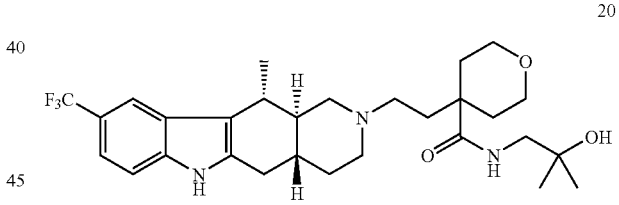

20

A mixture of acid 7 (0.102 g, 0.22 mmol), 2-aminomethyl-2-propanol (0.095 g, 0.88 mmol, prepared according to Rai, B.; Dekhordi, L. S.; Khodr, H.; Jin, Y.; Liu, Z.; R. C. Hider (1998) *J. Med. Chem.* 41:3347-3359), EDC-HCl (0.127 g, 0.66 mmol), HOBt (0.089 g, 0.66 mmol), NMP (0.11 mL, 1 mmol), DCM (2 mL) and DMF (2 mL) was stirred at r.t. overnight. The mixture was poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 20-40% MeOH/DCM mixed with 0-10% NH$_4$OH to yield 20 as a white solid (0.085 g). $^1$H NMR δ (DMSO, 500 MHz): 11.20 (s, 1H), 7.79 (s, 1H), 7.54 (m, 1H), 7.44 (d, J=8.5 Hz, 1H), 7.28 (d, J=8.5 Hz, 1H), 4.51 (s, 1H), 3.68 (m, 2H), 3.38 (m, 2H), 3.26 (m, 1H), 3.13 (d, J=6.0 Hz, 1H), 2.90 (m, 1H), 2.75 (m, 1H), 2.60 (m, 1H), 2.40 (m, 1H), 2.28 (m, 2H), 2.00 (m, 2H), 1.80 (m, 5H), 1.45 (m, 4H), 1.40 (d, J=6.5 Hz, 3H), 1.29 (m, 1H), 1.09 (s, 6H). MS (ES): 536 [M+H].

Example 18

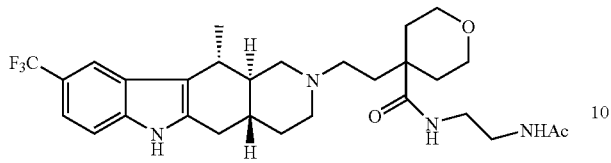

21

Synthesized in two steps: To a mixture of acid 7 (1.00 g, 2.2 mmol), DMF (3 drops) and DCM (20 mL) was added (COCl)₂ (10 mL, 2 M in DCM, 20 mmol). When the gas release ceased, the mixture was placed under a rotary evaporator followed by a high vacuum pump to obtain the corresponding acyl chloride as a solid. The acyl chloride (dissolved in 10 mL of DCM and 5 mL of DMF) was added to a flask containing NH₂CH₂CH₂NH₂ (4.42 mL, 66 mmol) in DCM (15 mL). The mixture was stirred at r.t. for 1 h, poured into saturated NaHCO₃ and extracted with EtOAc. The organic layer was separated, washed with brine, dried with anhydrous Na₂SO₄, concentrated by rotary evaporation and purified by flash chromatography on silica gel eluted with a gradient elution of 20-40% MeOH/DCM mixed with 0-10% NH₄OH to yield the corresponding aminoethyl amide as a yellowish solid.

The above amide (0.035 g, 0.07 mmol) was stirred with AcCl (0.01 mL, 0.14 mmol) and TEA (0.035 mL, 0.25 mmol) in DCM (1 mL) for 10 min. The mixture was directly loaded onto a silica gel column eluted with a gradient elution of 20-40% MeOH/DCM mixed with 0-7% NH₄OH to yield 21 as a yellowish solid (0.022 g). MS (ES): 549 [M+H].

Example 19

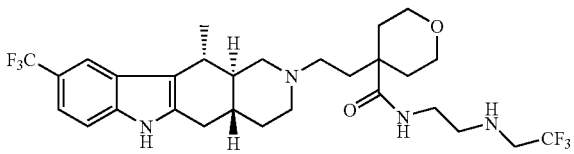

22

Synthesized in two steps: A mixture of the intermediate aminoethyl amide of Example 18 (0.67 g, 1.65 mmol), trifluoroacetic anhydride (0.292 mL, 2.1 mmol), TEA (0.42 mL, 3 mmol) and DCM (10 mL) was stirred at r.t. for 10 min. The mixture was poured into saturated NaHCO₃ and extracted with EtOAc. The organic layer was separated, washed with brine, dried with anhydrous Na₂SO₄, concentrated by rotary evaporation and purified by flash chromatography on silica gel with a gradient elution of 10-20% MeOH/DCM mixed with 1-2% NH₄OH to yield the corresponding trifluoromethyl acetamide as a yellowish solid (0.510 g).

The above amide (0.300 g, 0.5 mmol) was refluxed with LAH (0.050 g, 1.3 mmol) in THF (5 mL) for 1 h. At this time HPLC-MS indicated half completion of the reaction. A second portion of LAH (0.050 g, 1.3 mmol) was added. After refluxing for another 1 h, no more progress was observed. The mixture was poured into dilute ammonium hydroxide and extracted with EtOAc. The organic layer was separated, washed with brine, dried with anhydrous Na₂SO₄, concentrated by rotary evaporation. Flash chromatography on silica gel with a gradient elution of 20-40% MeOH/DCM mixed with 1-10% NH₄OH afforded no separation. Finally separation was achieved by preparative HPLC to yield 22 as a white solid (0.037 g). MS (ES): 589 [M+H].

Example 20

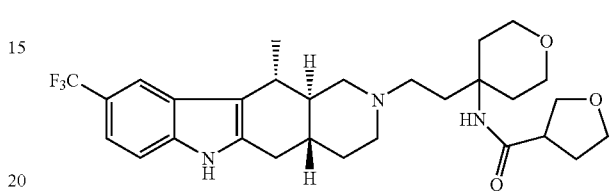

23

A mixture of amine 13 (0.090 g, 0.2 mmol), tetrahydro-3-furoic acid (0.047 g, 0.4 mmol), EDC.HCl (0.115 g, 0.6 mmol), HOBt (0.081 g, 0.6 mmol), TEA (0.140 mL, 1 mmol), DCM (1 mL) and DMF (1 mL) was stirred at r.t. overnight. The mixture was poured into saturated NaHCO₃ and extracted with EtOAc. The organic layer was separated, washed with brine, dried with anhydrous Na₂SO₄, concentrated by rotary evaporation and purified by flash chromatography on silica gel with a gradient elution of 20-40% MeOH/DCM mixed with 0-10% NH₄OH to yield 23 as a yellowish solid (0.069 g). ¹H NMR δ (DMSO, 500 MHz): 11.20 (s, 1H), 7.78 (s, 1H), 7.47 (s, br, 1H), 7.43 (d, J=8.5 Hz, 1H), 7.28 (d, J=8.5 Hz, 1H), 3.89 (t, J=7.8 Hz, 1H), 3.58-3.85 (m, 6H), 3.48 (m, 2H), 3.30 (m, 1H), 3.05 (m, 1H), 2.74 (m, 1H), 2.62 (m, 1H), 2.51 (m, 1H), 2.35 (m, 1H), 2.09 (m, 2H), 2.00 (m, 2H), 1.92 (m, 2H), 1.84 (m, 1H), 1.4-1.55 (m, 3H), 1.37 (d, J=6.5 Hz, 3H), 1.30 (m, 1H). MS (ES): 534 [M+H].

Example 21

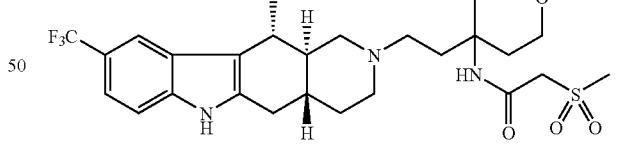

24

A mixture of amine 13 (0.065 g, 0.15 mmol), methanesulfonyl acetic acid (0.061 g, 0.45 mmol), EDC.HCl (0.086 g, 0.45 mmol), HOBt (0.061 g, 0.45 mmol), NMP (0.165 mL, 1.5 mmol), DCM (1.5 mL) and DMF (1.5 mL) was stirred at r.t. for 24 h. The mixture was poured into saturated NaHCO₃ and extracted with EtOAc. The organic layer was separated, washed with brine, dried with anhydrous Na₂SO₄, concentrated by rotary evaporation and purified by flash chromatography on silica gel with a gradient elution of 15-20% MeOH/DCM mixed with 1-2% NH₄OH to yield 24 as a white solid (0.052 g). ¹H NMR δ (DMSO, 500 MHz): 11.19 (s, 1H), 7.90 (s, 1H), 7.79 (s, 1H), 7.44 (d, J=8.5 Hz, 1H), 7.28 (d, J=8.5 Hz, 1H), 4.13 (s, 2H), 3.63 (m, 2H), 3.54

(m, 2H), 3.32 (m, 2H), 3.11 (s, 3H), 2.92 (m, 1H), 2.74 (m, 1H), 2.60 (m, 1H), 2.40 (m, 3H), 2.08 (m, 2H), 1.92 (m, 2H), 1.83 (m, 1H), 1.69 (m, 1H), 1.54 (m, 2H), 1.40 (m, 2H), 1.38 (d, J=6.5 Hz, 3H), 1.19 (m, 1H). MS (ES): 556 [M+H].

Example 22

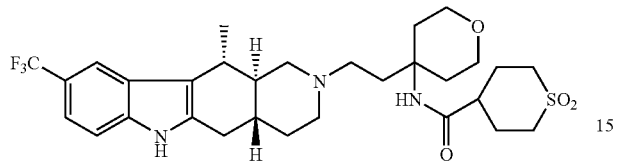

25

A mixture of amine 13 (0.097 g, 0.224 mmol), 4,4-dioxo-tetrahydrothiopyranyl carboxylic acid (0.040 g, 0.224 mmol, prepared as following), EDC.HCl (0.107 g, 0.56 mmol), HOBt (0.076 g, 0.56 mmol), NMP (0.275 mL, 2.5 mmol), DCM (1.5 mL) and DMF (1.5 mL) was stirred at r.t. overnight. The mixture was poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 20% MeOH/DCM mixed with 1-3% NH$_4$OH to yield 25 as a white solid (0.074 g).

$^1$H NMR δ (DMSO, 500 MHz): 11.19 (s, 1H), 7.78 (s, 1H), 7.50 (s, 1H), 7.43 (d, J=8.5 Hz, 1H), 7.28 (d, J=8.5 Hz, 1H), 3.62 (m, 2H), 3.48 (m, 2H), 3.25 (m, 1H), 3.14 (m, 4H), 2.90 (m, 1H), 2.74 (m, 1H), 2.58 (m, 3H), 2.2-2.45 (m, 3H), 2.09 (m, 6H), 1.8-1.98 (m, 4H), 1.65 (m, 1H), 1.43 (m, 3H), 1.38 (d, J=6.5 Hz, 3H), 1.28 (m, 1H). MS (ES): 596 [M+H].

Preparation of 4,4-dioxo-tetrahydrothiopyranyl carboxylic acid: A mixture of 2,2-dimethyl-1,3-dioxane-4,6-dione (10 g, 69.4 mmol), vinyl sulfone (8.19 g, 69.4 mmol), KOH (9.72 g, 173.6 mmol) and tBuOH (140 mL) was refluxed overnight. The supernant was decanted and 120 mL of 20% aqueous H$_2$SO$_4$ was added to the residual solid. The obtained mixture was refluxed for another 3 h, extracted with iPrOH/CHCl$_3$, dried with anhydrous Na$_2$SO$_4$ and concentrated by rotary evaporation to afford the desired 4,4-dioxo-tetrahydrothiopyranyl carboxylic acid.

Example 23

26

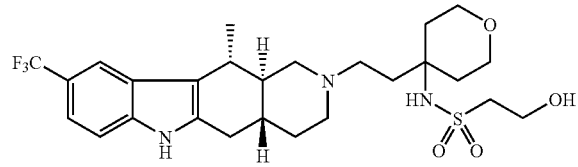

Synthesized in two steps: A mixture of amine 13 (0.100 g, 0.23 mmol), ClSO$_2$CH$_2$CO$_2$Me (0.039 g, 0.3 mmol), pyridine (0.49 mL, 0.6 mmol) and DCM (2 mL) was stirred at r.t. for 20 min. The mixture was poured into saturated NaHCO$_3$ and extracted with EtOAc. The organic layer was separated, washed with brine, dried with anhydrous Na$_2$SO$_4$, concentrated by rotary evaporation and purified by prep. HPLC to yield the corresponding sulfonamide.

The above sulfonamide (0.020 g, 0.038 mmol) was reacted with LAH (0.20 mL, 1 M in THF, 0.2 mmol) in THF (1 mL) at r.t. for 15 min. The reaction mixture was poured into dilute ammonium hydroxide and extracted with EtOAc. The organic layer was separated, washed with brine, dried with anhydrous Na$_2$SO$_4$, concentrated by rotary evaporation. Flash chromatography on silica gel with a gradient elution of 15-20% MeOH/DCM mixed with 1-3% NH$_4$OH afforded compound 26 as a white solid (0.004 g). MS (ES): 544 [M+H].

Example 24

27

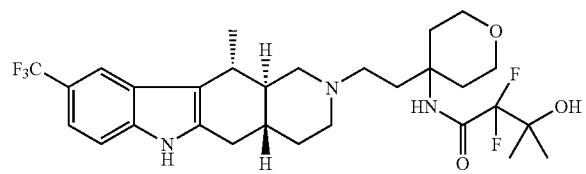

A mixture of amine 13 (0.239 g, 0.55 mmol), C(Me)$_2$(OH)CF$_2$CO$_2$H (0.085 g, 0.55 mmol, prepared according to Dolbier, Jr. W. R.; Ocampo, R. (1995) *J. Organic Chem.* 60:5378 and Hallinan, E. A.; Fried, J. (1984) *Tetrahedron Lett.* 25:2301), EDC-HCl (0.264 g, 1.37 mmol), HOBt (0.186 g, 1.37 mmol), NMP (0.44 mL, 4 mmol), DCM (3 mL) and DMF (3 mL) was stirred at r.t. for 24 h. The mixture was poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 15-20% MeOH/DCM mixed with 0-2% NH$_4$OH to yield 27 as a white solid (0.098 g). $^1$H NMR δ (DMSO, 500 MHz): 11.19 (s, 1H), 7.79 (m, 2H), 7.44 (d, J=8.5 Hz, 1H), 7.28 (d, J=8.5 Hz, 1H), 5.59 (s, 1H), 3.63 (m, 2H), 3.52 (m, 2H), 3.25 (m, 1H), 2.93 (m, 1H), 2.75 (m, 1H), 2.61 (m, 1H), 2.40 (m, 3H), 2.25 (m, 2H), 1.94 (m, 3H), 1.81 (m, 1H), 1.66 (m, 1H), 1.56 (m, 2H), 1.42 (m, 2H), 1.38 (d, J=6.5 Hz, 3H), 1.19 (m, 7H). MS (ES): 572 [M+H].

Example 25

28

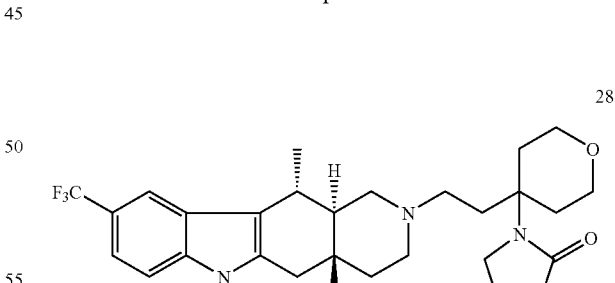

Step 1. A mixture of amine 13 (0.654 g, 1.5 mmol), OHCCH$_2$CH$_2$CH$_2$CO$_2$Et (0.260 g, 2 mmol), NaBH(OAc)$_3$ (1.27 g, 6 mmol) and ClCH$_2$CH$_2$Cl (10 mL) was stirred at r.t. overnight. The mixture was poured into dilute NH$_4$OH and extracted with EtOAc. The organic layer was separated, washed with brine, dried with anhydrous Na$_2$SO$_4$, concentrated by rotary evaporation and purified by flash chromatography on silica gel with a gradient elution of 15-20% MeOH/DCM mixed with 1-4% NH$_4$OH to yield the corresponding monoalkylated amine (0.35 g).

The product obtained above (0.35 g, 0.63 mmol) was hydrolyzed by treating with LiOH.H₂O (0.50 g, 12 mmol) in dioxane (4 mL) and H₂O (2 mL) at r.t. for 3 h. The mixture was acidified with HOAc to slightly acidic, and was concentrated to dryness.

The above acid (~0.1 mmol, contained inorganic salt) was heated with NaOAc (0.200 g) in Ac₂O (2 mL) at 105° C. for 20 min. The reaction mixture was poured into saturated NaHCO₃ and extracted with EtOAc. The organic layer was separated, washed with brine, dried with anhydrous Na₂SO₄, concentrated by rotary evaporation and purified by flash chromatography on silica gel with a gradient elution of 15-20% MeOH/DCM mixed with 0-3% NH₄OH to yield 28 as a white solid (0.040 g). ¹H NMR δ (DMSO, 500 MHz): 11.19 (s, 1H), 7.78 (s, 1H), 7.43 (d, J=8.5 Hz, 1H), 7.28 (d, J=8.5 Hz, 1H), 3.64 (m, 2H), 3.45 (m, 4H), 3.36 (m, 1H), 2.92 (m, 1H), 2.75 (m, 1H), 2.61 (m, 1H), 2.38 (m, 5H), 2.26 (t, J=8.0 Hz, 2H), 1.89 (m, 6H), 1.68 (m, 1H), 1.41 (m, 2H), 1.38 (d, J=6.5 Hz, 3H), 1.26 (m, 1H). MS (ES): 504 [M+H].

Example 26

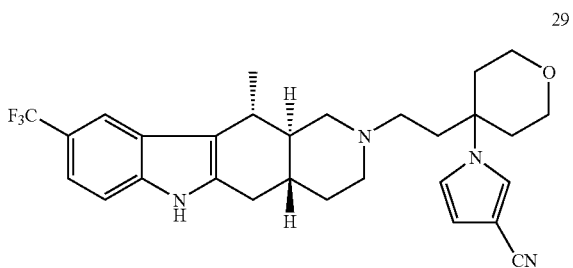

29

Synthesized in two steps: A mixture of amine 13 (0.664 g, 1.52 mmol), 2,5-dimethoxy-3-tetrahydrofuran-carboxaldehyde (0.487 g, 3.0 mmol) and HOAc (8 mL) was heated to 70° C. for 2 h. The mixture was cooled to r.t., basified with saturated NaHCO₃ and extracted with EtOAc. The organic layer was separated, washed with brine, dried with anhydrous Na₂SO₄, concentrated by rotary evaporation and purified by flash chromatography on silica gel with a gradient elution of 10-20% MeOH/DCM mixed with 0-2% NH₄OH to yield the corresponding formylpyrrole derivative (0.70 g).

The above aldehyde was converted to nitrile by the following reaction. In a vial containing NH₂OH.HCl (0.083 g, 1.2 mmol) and CH₃CN (3 mL) at 0° C. was added TEA (0.168 mL, 1.2 mmol) and the aldehyde (0.470 g, 0.91 mmol). The mixture was stirred at 0° C. for 30 min. and at r.t. for 4 h. At this time, phthalic anhydride (0.178 g, 1.2 mmol) was added and the mixture was heated to 90° C. for 1 h, poured into saturated NaHCO₃ and extracted with EtOAc. The organic layer was separated, washed with brine, dried with anhydrous Na₂SO₄, concentrated by rotary evaporation and purified by flash chromatography on silica gel with a gradient elution of 10-20% MeOH/DCM mixed with 0-1% NH₄OH to yield 29 as a yellowish solid (0.167 g). ¹H NMR δ (DMSO, 500 MHz): 11.18 (s, 1H), 7.84 (s, 1H), 7.77 (s, 1H), 7.43 (d, J=8.5 Hz, 1H), 7.28 (d, J=8.5 Hz, 1H), 7.17 (m, 1H), 6.54 (m, 1H), 3.71 (m, 2H), 3.41 (m, 2H), 3.08 (m, 1H), 2.73 (m, 2H), 2.55 (m, 2H), 2.38 (m, 1H), 2.25 (m, 2H), 1.85-2.1 (m, 6H), 1.77 (m, 2H), 1.54 (m, 1H), 1.36 (d, J=6.5 Hz, 3H), 1.23 (m, 2H). MS (ES): 511 [M+H].

Example 27

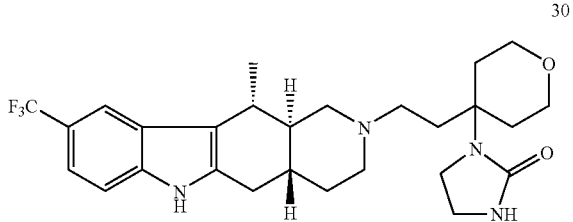

30

Synthesized in three steps: A mixture of amine 13 (0.600 g, 1.38 mmol), BocNHCH₂CHO (0.220 g, 0.38 mmol), NaBH(OAc)₃ (1.17 g, 5.5 mmol) and ClCH₂CH₂Cl (14 mL) was stirred at r.t. overnight. The mixture was poured into dilute NH₄OH and extracted with EtOAc. The organic layer was separated, washed with brine, dried with anhydrous Na₂SO₄, concentrated by rotary evaporation and purified by flash chromatography on silica gel with a gradient elution of 15-20% MeOH/DCM mixed with 1-4% NH₄OH to yield the corresponding reductive amination product (0.311 g).

The product obtained above (0.311 g, 0.537 mmol) was stirred with HCl (1.5 mL, 4 M in dioxane, 6 mmol) in 1.5 mL of DCM for 30 min. The mixture was poured into dilute NH₄OH and extracted with EtOAc. The organic layer was separated, washed with brine, dried with anhydrous Na₂SO₄, concentrated by rotary evaporation to yield the de-protected product which was directed used for the next step.

The resulted de-Boc product (0.129 g, 0.27 mmol) was refluxed with carbonyldiimidazole (0.087 g, 0.54 mmol) in DCM (8 mL) for 1 h. The reaction mixture was poured into saturated NaHCO₃ and extracted with EtOAc. The organic layer was separated, washed with brine, dried with anhydrous Na₂SO₄, concentrated by rotary evaporation and purified by flash chromatography on silica gel with a gradient elution of 15-20% MeOH/DCM mixed with 1-2% NH₄OH to yield 30 as a white solid (0.123 g). MS (ES): 505 [M+H].

Example 28

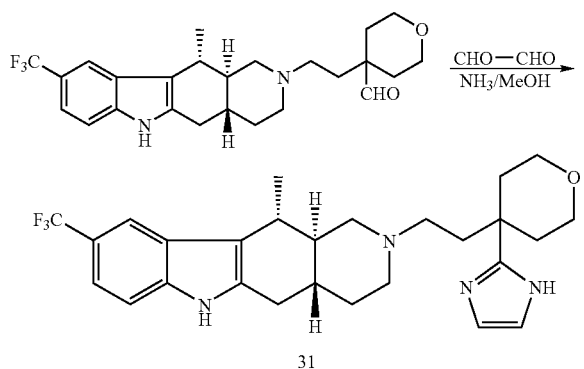

31

A sample of the alcohol compound from Example 3 was converted to the corresponding aldehyde by oxidation with SO₃.Py and DMSO. To the solution of this aldehyde (0.100 g, 0.2 mmol) in MeOH (1 mL) at 0° C. was added glyoxal (0.055 g, 0.95 mmol, 50% in water) followed by NH₃ (0.50 mL, 1 mmol, 2 M in MeOH). The mixture was allowed to warm to r.t. and stirred for 24 h. The mixture was poured into with saturated NaHCO₃ and extracted with EtOAc. The organic layer was separated, washed with brine, dried with anhydrous Na₂SO₄, concentrated by rotary evaporation and purified by flash chromatography on silica gel with a gradient elution of 15-20% MeOH/DCM with 1-4% NH₄OH added to yield 31 as a yellowish solid (0.027 g). ¹H NMR δ (DMSO, 500 MHz): 11.60 (s, br, 1H), 11.20 (s, 1H), 7.77 (s, 1H), 7.43 (d, J=8.5 Hz, 1H), 7.28 (d, J=8.5 Hz, 1H), 6.96 (s, br, 2H), 3.70 (m, 2H), 3.32 (m, 4H), 3.19 (m, 1H), 2.88 (s, 1H), 2.72 (m, 1H), 2.57 (m, 1H), 2.51 (m, 1H), 2.38 (m, 1H), 2.23 (m, 2H), 2.09 (m, 1H), 1.82 (m, 3H), 1.66 (m, 2H), 1.39 (m, 2H), 1.65 (d, J=6.5 Hz, 3H), 1.19 (m, 1H). MS (ES): 487 [M+H].

Example 29

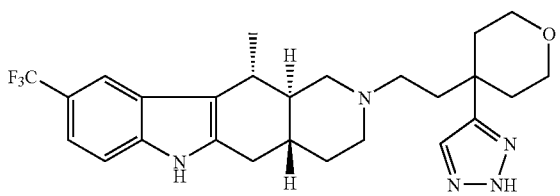

32

Synthesized in two steps: To a solution of diazomethylphosphonate (0.180 g, 1.2 mmol, Seyferth, D.; Marmor, R. S.; Hilbert, P. (1971) *J. Organic Chem.* 36:1379) in THF (6 mL) cooled to −78° C. under a nitrogen atmosphere was added KOtBu (1.8 mL, 1.8 mmol, 1.0 M in THF) dropwise. The obtained mixture was stirred for 10 min. at the low temperature. An aldehyde (0.268 g, 0.6 mmol, dissolved in THF, same one used as for the preparation of compound 31) was added to the above mixture dropwise. The mixture was stirred for 30 min. at −78° C. and another 30 min. at r.t. The reaction was quenched with water, and the mixture was poured into saturated NaHCO₃ and extracted with EtOAc. The organic layer was separated, washed with brine, dried with anhydrous Na₂SO₄, concentrated by rotary evaporation and purified by flash chromatography on silica gel eluted with gradient elution of 5-20% MeOH/DCM to yield the corresponding alkyne as a white solid (0.200 g).

The obtained alkyne (0.100 g, 0.22 mmol) was heated with TMSN₃ (1 mL) in a sealed vial at 140° C. for two days. The whole mixture was directly loaded onto a column, eluted with 15-20% MeOH/DCM mixed with 1-5% NH₄OH to yield 32 as a white solid (0.0048 g). MS (ES): 488 [M+H].

Example 30

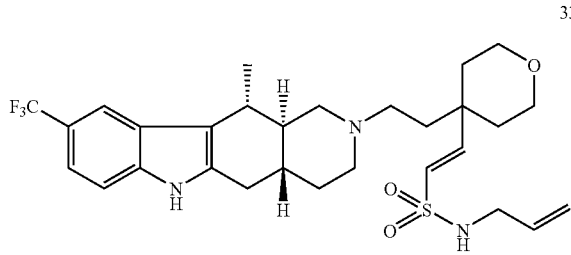

33

Lithium diisopropylamide (1.1 mL, 2.0 M, 2.2 mmol) was added to a solution of THF (0.25 M solution) containing N-allyl-N-t-butoxycarbonyl-methanesulfonamide (0.518 g, 2.2 mmol) at −78° C. After stirring for 50 min. at −78° C., the solution of the aldehyde intermediate from Example 28 in dry THF (0.470 g, 1.05 mmol) was added and the mixture was stirred at −78° C. to room temperature overnight. The reaction was treated with saturated sodium bicarbonate solution and extracted with ethyl acetate, the organic layer was washed with brine and dried, concentrated and purified by flash chromatography on silica gel eluted with 3% MeOH/DCM to yield 3 (R¹=Boc, R²=allyl) as a yellowish oil (0.25 g). The resulting oil was treated with trifloroacetic acid in DCM (0.5 M) to yield 33 as yellow film.

¹H NMR (400 MHz, CDCl3) δ 7.93 (s, 1H), 7.84 (s, 1H), 7.33 (s, 1H), 6.71 (d, J=15.6 Hz, 1H), 6.16 (d, J=15.6 Hz, 1H), 5.86 (m, 1H), 5.30 (dd, J=1.3, J=3.8 Hz, 1H), 5.27 (d, J=1.2 Hz, 1H), 5.22 (dd,, J=1.1, 10.2 Hz, 1H), 4.38 (s, 1H), 3.91 (m, 2H), 3.69 (m, 2H), 3.58 (m, 2H), 3.30 (d, J=10.5 Hz, 1H), 2.98 (d, J=10.5 Hz, 1H), 2.68 (m, 2H), 2.30-2.48 (m, 3H), 1.95 (m, 1H), 1.86 (d, J=9.1 Hz, 1H), 1.70-1.81 (m, 6H), 1.49-1.59 (m, 4H), 1.45 (d, J=6.6 Hz, 3H). ESI (MH⁺) m/z 566.

Example 31

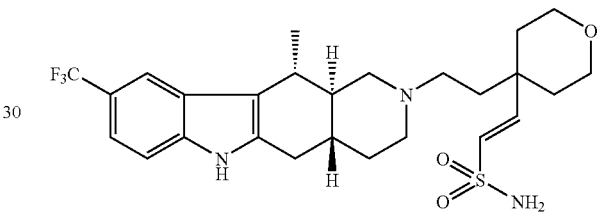

34

A sample of compound 33 (0.067 g, 0.12 mmol) was treated with tetrakis(triphenylphosphine)-plladium (0.012 g, 0.01 mmol) and 1,3-dimethyl barbituric acid (0.2 g, 1.28 mmol) in DCM at 35° C. overnight, to yield 34 as a solid (0.006 g). ¹H NMR (400 MHz, CDCl3) δ 8.04 (s, 1H), 7.92 (s, 1H), 7.33 (s, 2H), 6.77 (d, J=15.6 Hz, 1H), 6.34 (d, J=15.6 Hz, 1H), 4.68 (s, 1H), 3.77 (m, 2H), 3.69 (m, 2H), 3.3.29 (d, J=10 Hz, 1H), 2.97 (d, J=10 Hz, 1H), 2.66 (m, 2H), 2.31-2.50 (m, 3H), 1.95 (m, 1H), 1.86 (d,, J=9.1 Hz 1H), 1.70-1.81 (m, 7H), 1.49-1.59 (m, 4H), 1.45 (d, J=6.6 Hz, 3H). ESI (MH⁺) m/z 526.

Example 32

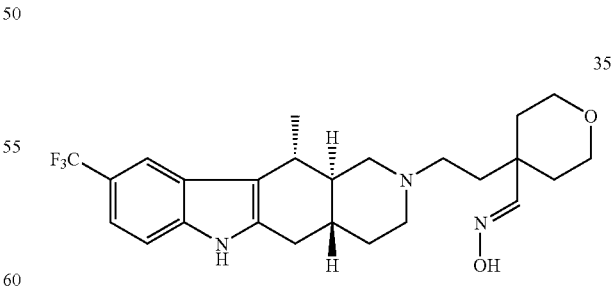

35

The mixture of aldehyde compound from Example 28 (0.1 g, 0.22 mmol), hydroxylamine hydrochloride (0.024 g, 0.33 mmol) and triethylamine (0.045 g, 0.45 mmol) in MeOH (0.2 M solution) stirred at room temperature for 5.5 h. The reaction was treated with saturated sodium bicarbonate solution and extracted with ethyl acetate, the organic layer was washed with brine and dried, concentrated, redissolved in DCM, pale yellow solid came out, rinsed the solid with more DCM, dried to yield 0.04 g 35 as pale yellow solid. $^1$H NMR (400 MHz, DMSO) δ 11.2 (s, 1H), 10.55 (s, 1H), 7.80 (s, 1H), 7.41 (d, J=9.0 Hz, 1H), 7.26 (d, J=9.0 Hz, 1H), 7.23 (s, 1H), 3.64 (br, 2H), 3.43 (m, 2H), 3.30 (s, 3H), 3.21 (d, J=10.0 Hz, 1H), 2.88 (d, J=10.0 Hz, 1H), 2.72 (dd, J=4 Hz, J=13 Hz, 1H), 2.58 (m, 1H), 2.49 (t, J=1.75 Hz, 1H), 2.39 (m, 1H), 2.26 (m, 1H), 1.86 (m, 1H), 1.72-1.80 (m, 3H), 1.62 (t, J=7.5 Hz, 2H), 1.49 (td, J=3.8, Hz J=14 Hz, 2H), 1.38 (m, 1H), 1.35 (d, J=6.6 Hz, 3H), 1.27 (m, 1H). ESI (MH$^+$) m/z 464.

Example 33

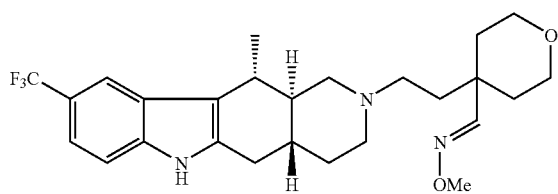

36

Synthesized in the same way as in Example 29 with the exception of replacing hydroxylamine hydrochloride with methoxyamine hydrochloride. $^1$H NMR (400 MHz, DMSO) δ 11.12 (s, 1H), 7.77 (s, 1H), 7.42 (d, J=8.3 Hz, 1H), 7.35 (s, 1H), 7.27 (d, J=8.3 Hz, 1H), 3.74 (s, 2H), 3.65 (d, J=11.4 Hz, 2H), 3.45 (t, J=11.4 Hz, 2H), 3.31 (s, 3H), 3.23 (d, J=10.6 Hz, 1H), 2.89 (d, J=8.8 Hz, 1H), 2.72 (dd, J=4 Hz, J=13 Hz, 1H), 2.59 (m, 1H), 2.49 (br, 1H), 2.39 (m, 1H), 2.28 (m, 2H), 1.80 (m, 1H), 1.72-1.80 (m, 3H), 1.66 (br, 3H), 1.50 (br, 1H), 1.40 (br, 1H), 1.36 (d, J=6.6 Hz, 3H), 1.26 (m, 1H). ESI (MH$^+$) m/z 478.

Example 34

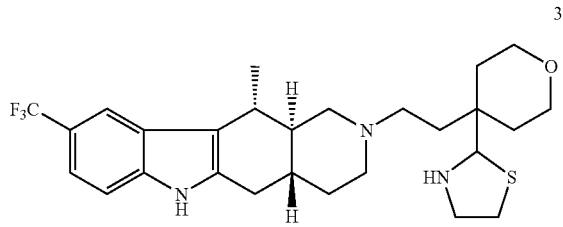

37

The mixture of aldehyde intermediate from Example 28 (0.10 g, 0.22 mmol), 2-amino-ethanethiol hydrochloride (0.062 g, 0.54 mmol) and sodium methoxide (0.078 g, 1.4 mmol) in MeOH (0.2 M solution) was stirred at room temperature overnight. The reaction was treated with saturated sodium bicarbonate solution and extracted with ethyl acetate, the organic layer was washed with brine, dried, concentrated and purified by flash chromatography on silica gel eluted with 10:1:0.1 DCM-MeOH—NH$_4$OH to yield 37 as yellow solid (0.06 g). $^1$H NMR (400 MHz, CDCl$_3$) δ 8.09 (s, 1H), 7.83 (s, 1H), 7.33 (s, 2H), 4.65 (d, J=6.7 Hz, 1H), 3.79 (m, 2H), 3.70 (dd, J=2.76 Hz, J=9.7 Hz, 1H), 3.53-3.66 (m, 4H), 3.48 (s, 3H), 3.29 (d, J=9.5 Hz, 1H), 3.16 (d, J=9.5 Hz, 1H), 2.95-2.98 (m, 2H), 2.82 (m, 1H), 2.82 (m, 1H), 2.67 (m, 4H), 2.35-2.6 (br, 2H), 2.20 (m, 2H), 2.09 (m, 1H), 1.86 (m, 2H), 1.60-1.80 (m, 2H), 1.2-1.55(m, 3H). ESI (MH$^+$) m/z 508.

Example 35

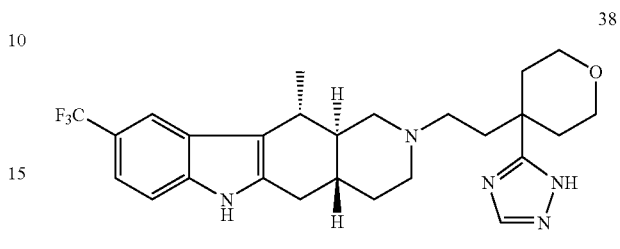

38

Synthesized in two steps: A mixture of amide 8 (0.150 g, 0.32 mmol) and (MeO)$_2$CHN(Me)$_2$ was heated to 120° C. for 15 min. After cooled to r.t., the whole was directly loaded onto a column eluted with 15-30% MeOH/DCM mixed with 1-10% NH$_4$OH to yield the corresponding acylamidine as a yellow solid (0.120 g).

The above acylamnidine was treated with NH$_2$NH$_2$.H$_2$O (0.030 mL, 0.6 mmol) in AcOH (1 mL) at 90° C. for 10 min. After cooling to r.t., the whole was directly loaded onto a column eluted with 10-30% MeOH/DCM mixed with 1-4% NH$_4$OH to yield triazole 38 as a white solid (0.050 g). $^1$H NMR δ (DMSO, 500 MHz): 11.18 (s, 1H), 7.77 (s, 1H), 7.43 (d, J=8.5 Hz, 1H), 7.28 (d, J=8.5 Hz, 1H), 3.72 (m, 2H), 3.28 (m, 3H), 3.12 (m, 1H), 2.79 (m, 1), 2.71 (m, 1H), 2.55 (m, 2H), 2.37 (m, 1H), 2.23 (m, 2H), 2.04 (m, 2H), 1.77 (m, 6H), 1.53 (m, 1H), 1.33 (m, 5H), 1.22 (m, 1H). MS (ES): 488 [M+H].

Example 36

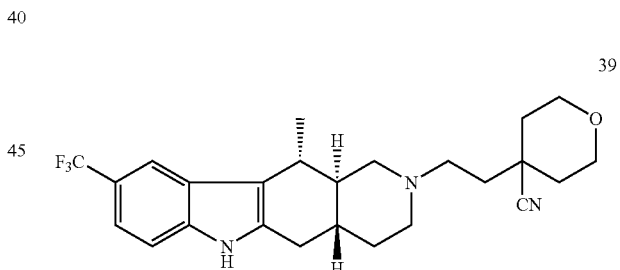

39

The mixture of amide 8 (0.695 g, 1.50 mmol) and POCl$_3$ (0.42 mL, 4.5 mmol) in anhydrous pyridine (14 mL) was heated to 120° C. in a sealed vessel for 2 h. The mixture was cooled to r.t., poured into saturated NaHCO$_3$ solution and extracted with EtOAc. The organic layer was separated, washed with brine, dried with anhydrous Na$_2$SO$_4$, concentrated by rotary evaporation and purified by flash chromatography on silica gel with a gradient elution of 5-30% MeOH/DCM to yield the corresponding nitrile as a yellowish solid (0.400 g). $^1$H NMR δ (DMSO, 500 MHz): 11.19 (s, 1H), 9.79 (s, 1H), 7.43 (d, J=8.5 Hz, 1H), 7.28 (d, J=8.5 Hz, 1H), 3.87 (m, 2H), 3.50 (m, 2H), 3.31 (m, 2H), 2.96 (m, 1H), 2.75 (m, 1H), 2.61 (m, 1H), 2.54 (m, 1H), 2.51 (m, 1H), 1.96 (m, 1H), 1.86 (m, 5H), 1.72 (m, 1H), 1.65 (m, 2H), 1.42 (m, 2H), 1.40 (d, J=6.5 Hz, 3H), 1.32 (m, 1H). MS (ES): 446 [M+H].

Example 37

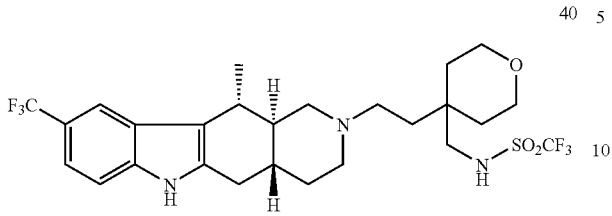

40

Synthesized in two steps: A mixture of amide 8 (0.630 g, 1.36 mmol) and LAH (4.76 mL, 1 M in THF, 4.76 mmol) was heated to 70° C. for 1 h. After cooling to r.t., the mixture was poured into dilute NH$_4$OH and extracted with EtOAc. The organic layer was separated, washed with brine, dried with anhydrous Na$_2$SO$_4$, concentrated by rotary evaporation and purified by flash chromatography on silica gel with a gradient elution of 20-50% MeOH/DCM mixed with 0-10% NH$_4$OH to yield the corresponding amine as a solid (0.500 g).

The above amine (0.060 g, 0.133 mmol) was reacted with (CF$_3$SO$_2$)$_2$O (0.067 mL, 0.4 mmol), TEA (0.084 mL, 0.6 mmol) in DCM (2 mL) at 0° C. for 10 min. The mixture was poured into water, basified with saturated NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution with 0-10% MeOH/EtOAc to yield 40 as a yellowish solid (0.045 g). $^1$H NMR δ (DMSO, 500 MHz): 11.26 (s, 1H), 7.81 (s, 1H), 7.46 (d, J=8.5 Hz, 1H), 7.30 (d, J=8.5 Hz, 1H), 3.67 (m, 1H), 3.56 (m, 4H), 3.35 (m, 1H), 2.97 (m, 4H), 2.82 (m, 2H), 2.66 (m, 2H), 2.31 (m, 2H), 1.99 (m, 1H), 1.80 (m, 4H), 1.68 (m, 1H), 1.4-1.5 (m, 4H), 1.39 (d, J=6.5 Hz, 3H). MS (ES): 582 [M+H].

Example 38

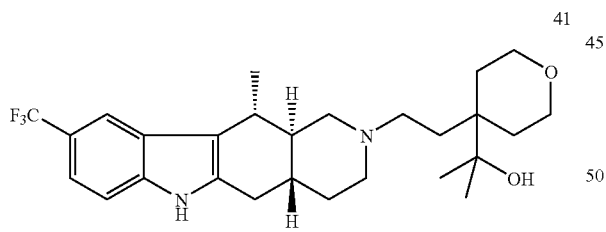

41

A mixture of ester 5 (0.070 g, 0.15 mmol) and MeLi (1.0 mL, 1.6 M in ether, 1.6 mmol) in THF (1.5 mL) was stirred at r.t. for 30 min. The mixture was poured into with saturated NaHCO$_3$ and extracted with EtOAc. The organic layer was separated, washed with brine, dried with anhydrous Na$_2$SO$_4$, concentrated by rotary evaporation and purified by flash chromatography on silica gel eluted with 20% MeOH/DCM to yield 41 as a white solid (0.012 g). $^1$H NMR δ (DMSO, 500 MHz): 11.21 (s, 1H), 7.78 (s, 1H), 7.44 (d, J=8.5 Hz, 1H), 7.29 (d, J=8.5 Hz, 1H), 5.95 (s, 1H), 3.69 (m, 2H), 3.47 (m, 2H), 3.32 (m, 2H), 2.99 (m, 1H), 2.76 (m, 1H), 2.63 (m, 1H), 2.52 (m, 1H), 2.42 (m, 2H), 1.85 (m, 4H), 1.67 (m, 2H), 1.2-1.55 (m, 5H), 1.38 (d, J=6.5 Hz, 3H), 1.08 (m, 6H). MS (ES): 479 [M+H].

Example 39

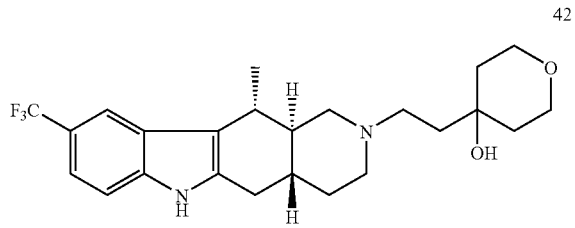

42

Synthesized in three steps: To a solution of tetrahydro-4H-pyran-4-one (5.00 g, 50 mmol) in THF (80 mL) was added allylmagnesium bromide (60 mL, 1 M/ether, 60 mmol). After stirring at r.t. for 30 min, the reaction was quenched with aqueous NH$_4$Cl and extracted with ether. The organic layer was separated, washed with brine, dried with anhydrous Na$_2$SO$_4$, concentrated by rotary evaporation and purified by flash chromatography on silica gel with a gradient elution of 50-60% EtOAc/hexanes to yield the alcohol adduct as a clear oil (2.51 g).

The obtained alkenyl alcohol (1.00 g, 7 mmol) was stirred with NaIO$_4$ (3.30 g, 15.4 mmol) and OsO$_4$ (40 mg) in MeOH (15 mL) and H$_2$O (15 mL) for 15 min. The entire mixture was directly loaded onto a column. Elution with EtOAc yielded the corresponding aldehyde as a brownish oil (0.70 g).

The above aldehyde (0.250 g, 1.7 mmol) was stirred with amine 4 (0.309 g, 1 mmol) and NaBH(OAc)$_3$ (0.856 g, 4 mmol) in ClCH$_2$CH$_2$Cl (7 mL) for 1.5 h. The mixture was poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 10-40% MeOH/DCM with 0-10% NH$_4$OH added to yield 42 as a brownish solid (0.145 g). $^1$H NMR δ (DMSO, 500 MHz): 11.22 (s, 1H), 7.79 (s, 1H), 7.44 (d, J=8.5 Hz, 1H), 7.29 (d, J=8.5 Hz, 1H), 5.11 (s, 1H), 3.62 (m, 5H), 3.36 (m, 1H), 3.03 (m, 1H), 2.76 (m, 1H), 2.62 (m, 1H), 2.51 (m, 1H), 2.42 (m, 1H), 1.87 (m, 1H), 1.65 (m, 2H), 1.25-1.6 (m, 9H), 1.39 (d, J=6.5 Hz, 3H). MS (ES): 437 [M+H].

Example 40

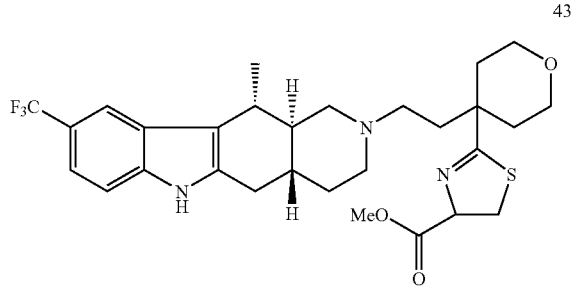

43

The mixture of acid 7 (1 g, 2.15 mmol), N-Boc-cystine methyl ester (1.06 g, 4.52 mmol), bis(2-oxo-3-oxazolidinyl)phosphinic chloride (1.096 g, 4.30 mmol) and triethylamine (0.456 g, 4.52 mmol) in DCM (0.4 M solution) was stirred at room temperature overnight. The reaction was treated with saturated sodium bicarbonate solution and extracted with ethyl acetate, the organic layer was washed with brine and dried, concentrated and purified by flash chromatography on silica gel eluted with 20:1:0.1 DCM:MeOH:NH₄OH to yield a yellow solid (0.6 g).

The resulting solid was treated with 20% trifluoroacetic acid in DCM. At the completion of the deprotection, excess reagent and solvent were removed by evaporation. The residue was refluxed in benzene (20 mL) and DCE (5 mL, to aid the solubility) overnight. The reaction was treated with saturated sodium bicarbonate solution and extracted with ethyl acetate, the organic layer was washed with brine and dried, concentrated and purified by flash chromatography on silica gel eluted with 5% MeOH/DCM to yield 43 as a yellow solid (0.16 g). ¹H NMR (400 MHz, CDCl₃) δ 8.1 (br, 1H), 7.90 (s, 1H), 7.32 (s, 2H), 5.24 (t, J=8.0 Hz, 1H), 3.80 (m, 6H), 3.53-3.66 (m, 5H), 3.48 (s, 3H), 2.66-2.74 (m, 2H), 2.52 (br, 2H), 1.80-2.10 (m, 6H), 1.73 (m, 3H), 1.45 (d, J=6.6 Hz, 3H), 0.95 (s, 1H. ESI (MH⁺) m/z 564.

Example 41

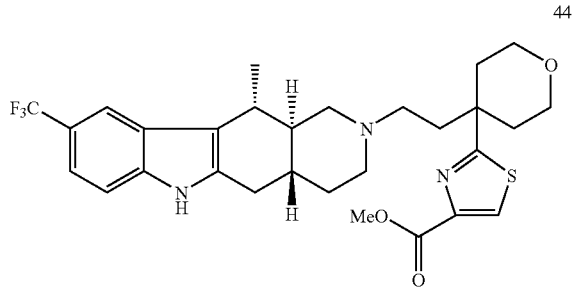

44

A sample of compound from Example 40 (0.2 g, 0.35 mmol) was treated with activated manganese dioxide (0.15 g, 1.75 mmol) in benzene refluxing overnight, to yield 44 as yellow solid (0.045 g). ¹H NMR (400 MHz, CDCl₃) δ 8.17 (s, 1H), 7.91 (s, 1H), 7.75 (s, 1H), 7.32 (s, 2H), 5.24 (t, J=8.0 Hz, 1H), 3.93 (s, 3H), 3.84 (m, 2H), 3.58(m, 2H), 3.20 (br, 1H), 2.82 (br, 1H), 2.65 (m, 2H), 2.43 (m, 1H), 2.34 (m, 2H), 1.90-2.10 (m, 5H), 1.80 (m, 2H), 1.57 (br, 4H), 1.45 (d, J=6.6 Hz, 3H). ESI (MH⁺) m/z 562.

Example 42

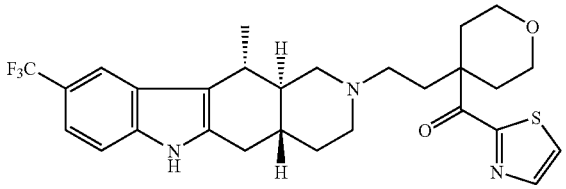

45

The mixture of amine 4 (0.107 g, 0.35 mmol), [4-(thiazole-2-carbonyl)-tetrahydro-pyran-4-yl]-acetaldehyde (0.069 g, 0.29 mmol, prepared similarly as described previously), and sodium triacetoxyborohydride (0.245 g, 1.15 mmol) in DCE (0.25 M solution) stirred at room temperature for 2 h. The reaction was treated with saturated sodium bicarbonate solution and extracted with ethyl acetate, the organic layer was washed with brine and dried, concentrated and purified by flash chromatography on silica gel eluted with 5% MeOH/DCM to yield 45 as yellow solid (0.09 g). ¹H NMR (400 MHz, CDCl₃) δ 7.9 (d, J=2.2 Hz, 2H), 7.80 (s, 1H), 7.4 J=2.2 Hz, 1H), 7.30 (s, 2H), 3.82 (m, 2H), 3.61 (t, J=9.8 Hz, 1H), 3.46 (t, J=9.8 Hz, 1H), 3.04 (d, J=9.8 Hz, 1H), 2.46-2.68 (m, 6H), 2.18-2.33 (m, 4H), 1.87 (m, 2H), 1.74 (m, 1H), 1.45-1.63 (m, 3H), 1.30 (d, J=6.6 Hz, 3H), 1.02 (m, 1H), 0.56 (br, 1H). ESI (MH⁺) m/z 532.

Example 43

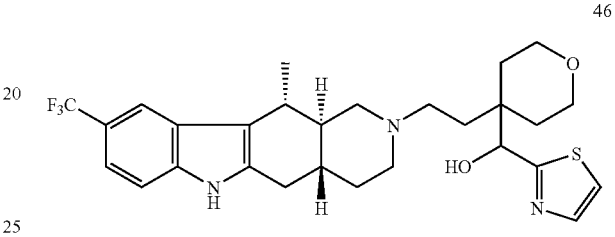

46

A sample of ketone from Example 42 (0.039 g, 0.073 mmol) was treated with sodium borohydride (0.02 g, 0.5 mmol) in THF for 30 min. The reaction was treated with saturated sodium bicarbonate solution and extracted with ethyl acetate, the organic layer was washed with brine and dried, concentrated and purified by flash chromatography on silica gel eluted with 5%-10% MeOH/DCM to yield 46 as yellow solid (0.005 g). ¹H NMR (400 MHz, CDCl₃) δ 7.95 (s, 1H), 7.80 (s, 1H), 7.79 (dd,, 3.3 Hz, J=4.6 Hz 1H), 7.38 (dd, J=3.3 Hz J=6.3 Hz, 1H), 7.35 (s, 1H), 4.91 (d, J=4.4 Hz, 1H), 3.85 (m, 2H), 3.75 (q, J=1.0 Hz, 2H), 3.41 (m, 1H), 3.46 (t, J=9.8 Hz, 1H), 3.19 (dd, J=4.7 Hz, J=7.4 Hz 2H), 3.0 (m, 1H), 2.85 (m, 1H), 2.73 (m, 1H), 2.61 (dd, J=9.0 Hz, J=14.9 Hz, 2H), 2.05-2.50 (m, 4H), 1.91 (m, 3H), 1.67 (m, 2H), 1.60 (m, 2H), 1.44 (dd, J=6.7 Hz J=9.4 Hz 3H). ESI (MH⁺) m/z 534.

Example 44

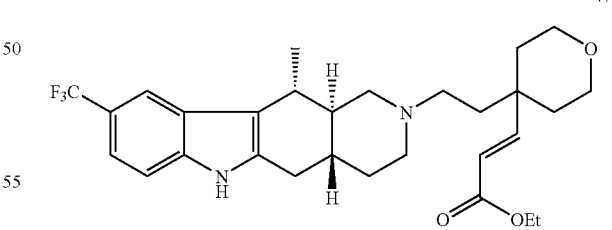

47

Step 1. LAH (0.64 g, 16.7 mL) was added to a dry THF solution (70 mL) containing the ester compound from Example 1 (4.0 g, 8.4 mmol) at room temperature. The solution was heated at reflux for 2 h. After heating, water (0.6 mL) was added followed by a 1 N solution of NaOH (0.6 mL), and a final addition of water (1.2 mL). The resulting solid was filtered washed with copious amount of dichloromethane. The filtrate was concentrated and used in the next step without purification: ESI (MH⁺) m/z 451.

Step 2. The resulting alcohol compound from above (0.6 g, 1.33 mmol) was dissolved in DMSO/Et₃N (2.5:1, 0.2 M) and was treated with SO₃.pyridine complex (0.85 g, 5.33 mmol) and at room temperature. After stirring for 2 h, the mixture was poured into water (60 mL) and extracted with dichloromethane (3×100 mL). The organic layers were washed with brine, dried over Na₂SO₃, and concentrated to give the aldehyde intermediate. ESI (MH⁺) m/z 449.

Step 3. Sodium hydride (0.96, 40 mmol) was added to a dry DMF (0.2 M) solution containing triethyl phosphonoacetate (4 mL, 20.0 mmol) at room temperature. After stirring for 10 min., the aldehyde intermediate from above (4.51 g, 10.1 mmol) was added and the mixture was stirred at room temperature overnight. Excess DMF was removed under vacuum and the remaining residue was taken up in a 10% MeOH/DCM solution, washed with water, dried with Na₂SO₃ and concentrated. A portion of this material was purified by using preparative HPLC (C18 column, 10%-90% acetonitrile/water gradient). ¹H NMR (400 MHz, MeOD) δ 7.79 (s, 1H), 7.39 (d, J=8 Hz, 1H), 7.29 (d, J=8 Hz, 1H), 6.87 (d, J=16 Hz, 1H), 6.00 (d, J=16 Hz, 1H), 4.22 (q, J=7 Hz, 2H), 3.89 (d, J=10 Hz, 1H), 3.77-3.81 (m, 3H), 3.67 (d, J=15 Hz, 1H), 3.57 (t, J=10 Hz, 3H), 3.01-3.18 (m, 4H), 2.78-2.91 (m, 4H), 2.52 (m, 1H), 2.20 (d, J=12 Hz, 1H), 2.00 (qn, J=6 Hz, 2H), 1.61-1.85 (m, 9H), 1.49 (d, J=6 Hz, 3H),1.31 (t, J=7 Hz, 3H). ESI (MH⁺) m/z 519.

Example 45

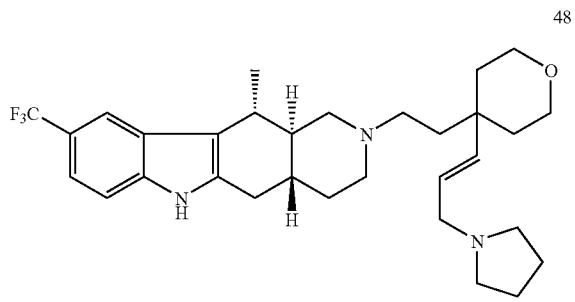

48

DIBAL (2.1 eq) was added to a dry THF solution (0.2 M) containing the ester from Example 44 (1 equiv.) at 0° C. After stirring for 4 h. the reaction was quenched at 0° C. with methanol and warmed to room temperature. The solution was concentrated under reduced pressure and the remaining residue was purified on silica eluting with 0-20% methanol/dichloromethane gradient: ESI (MH⁺) m/z 475.

Sodium triacetoxyborohydride (3 equiv.) was added to a dichloromethane solution (0.2 M) containing aldehyde intermediate from above (1 equiv.) and pyrroline (2 equiv.) at room temperature. After stirring overnight the solvent was removed using evaporation, and the remaining residue was purified using preparative HPLC (C18 column, 10%-90% acetonitrile/water gradient). ¹H NMR (400 MHz, MeOD,) δ 7.78 (s, 1H), 7.40 (d, J=8 Hz, 1H), 7.29 (d, J=8 Hz, 1H), 5.93 (d, J=16 Hz, 1H), 5.71 (td, J=7, J=16 Hz, 1H), 3.89 (m, 3H), 3.80 (m, 2H), 3.56-3.69 (m, 5H), 3.12-3.19 (m, 4H), 3.01 (t, J=14 Hz, 1H), 2.75-2.92 (m, 3H), 2.52 (dd, J=12, J=14 Hz, 1H), 2.10-2.22 (m, 3H), 2.04 (m, 2H), 1.95 (m, 2H), 1.64-1.84 (m, 7H), 1.49 (d, J=7 Hz, 3H); ESI (MH⁺) m/z 530.

Example 46

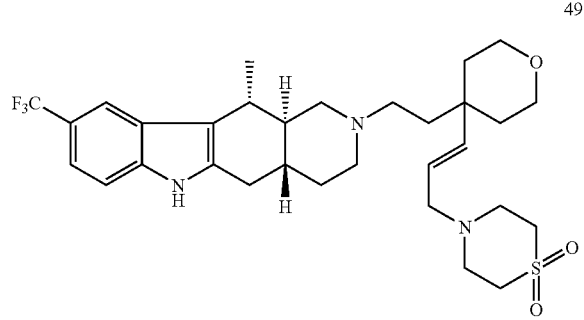

49

This compound was prepared in the same way as described in Example 45. (TFA salt). ¹H NMR (400 MHz, MeOD,) δ 7.79 (s, 1H), 7.40 (d, J=8 Hz, 1H), 7.29 (d, J=8 Hz, 1H), 5.95 (d, J=16 Hz, 1H), 5.74 (td, J=7, J=16 Hz, 1H), 3.90 (m, 3H), 3.66-3.80 (m, 7H), 3.40-3.60 (m, 6H), 3.10-3.26 (m, 2H), 2.99 (t, J=14 Hz, 1H), 2.75-2.91 (m, 3H), 2.50 (dd, J=12, J=14 1H), 2.17 (d, J=12 Hz, 1H), 1.96 (m, 2H), 1.62-1.82 (m, 7H). 1.48 (d, J=7 Hz, 3H). ESI (MH⁺) m/z 594.

Example 47

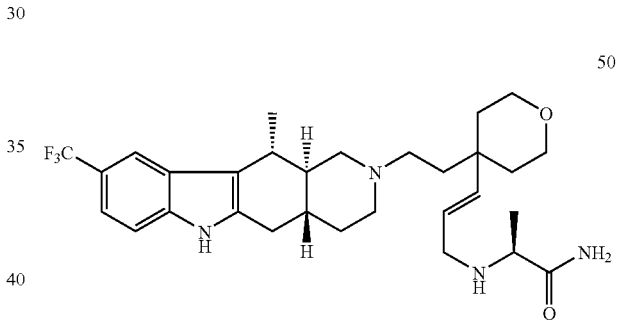

50

This compound was prepared in the same way as described in Example 45. (TFA salt). ¹H NMR (400 MHz, MeOD,) δ 7.79 (s, 1H), 7.40 (d, J=8 Hz, 1H), 7.30 (d, J=8 Hz, 1H), 5.87 (d, J=16 Hz, 1H), 5.66 (td, J=7 Hz, J=16 Hz, 1H), 3.93 (m, 3H), 3.60-3.80 (m, 7H), 3.10-3.21 (m, 2H), 3.00 (t, J=14 Hz, 1H), 2.75-2.93 (m, 3H), 2.54 (dd, J=12, J=14 Hz, 1H), 2.22 (d, J=12 Hz, 1H), 1.80-1.96 (m, 3H), 1.64-1.79 (m, 7H). 1.59 (d, J=7 Hz, 3H), 1.50 (d, J=7 Hz, 3H). ESI (MH⁺) m/z 547.

Example 48

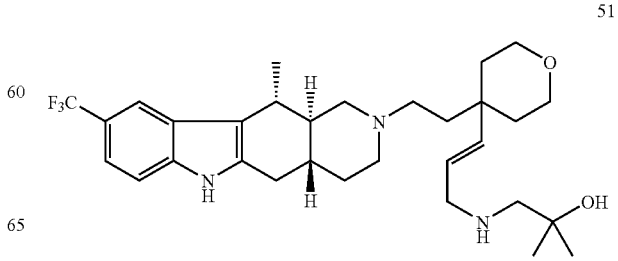

51

This compound was prepared in the same way as described in Example 45. (TFA salt). ¹H NMR (400 MHz, MeOD,) δ 7.78 (s, 1H), 7.40 (d, J=8 Hz, 1H), 7.29 (d, J=8 Hz, 1H), 5.87 (d, J=16 Hz, 1H), 5.69 (td, J=7, J=16 Hz, 1H), 3.90 (d, J=10 Hz, 1H), 3.59-3.80 (m, 7H), 3.10-3.21 (m, 2H), 3.00 (m, 3H), 2.79-2.92 (m, 3H), 2.53 (dd, J=12, J=14 Hz, 1H), 2.19 (d, J=12 Hz, 1H), 1.89-1.96 (m, 3H), 1.64-1.79 (m, 6H). 1.49 (d, J=7 Hz, 3H), 1.33 (s, 6H). ESI (MH⁺) m/z 548.

Example 49

52

This compound was prepared in the same way as described in Example 45. (TFA salt). ¹H NMR (400 MHz, MeOD,) δ 7.78 (s, 1H), 7.40 (d, J=8 Hz, 1H), 7.29 (d, J=8 Hz, 1H), 5.91 (d, J=16 Hz, 1H), 5.69 (td, J=7 Hz, J=16 Hz, 1H), 4.03 (q, J=9 Hz, 2H), 3.84-3.91 (m, 3H), 3.78 (m, 2H), 3.58-3.70 (m, 3H), 3.10-3.21 (m, 2H), 2.99 (t, J=14 Hz, 1H), 2.77-2.91 (m, 3H), 2.53 (dd, J=12, J=14 Hz, 1H), 2.19 (d, J=12 Hz, 1H), 1.78-1.97 (m, 3H), 1.57-1.78 (m, 6H). 1.48 (d, J=7 Hz, 3H). ESI (MH⁺) m/z 558.

Example 50

53

A sample of the aldehyde intermediate obtained in Step 1 in Example 44 was treated methyl Grinard reagent (2.5 equiv.) in dry THF (0.2 M) at room temperature. After stirring overnight the solvent was removed using evaporation, and the remaining residue was purified using preparative HPLC (C18 column, 10%-90% acetonitrile/water gradient). (TFA salt). ¹H NMR (400 MHz, MeOD,) δ 7.79 (s, 1H), 7.40 (d, J=8 Hz, 1H), 7.29 (d, J=8 Hz, 1H), 5.62 (ddd, J=2, J=6, J=16 Hz, 1H), 5.51 (d, J=16 Hz, 1H), 4.33 (qn, J=6 Hz, 1H), 3.89 (d, J=12 Hz, 1H) 3.77 (m, 2H), 3.59-3.69 (m, 3H), 3.10-3.21 (m, 2H), 3.00 (t, J=14 Hz, 1H), 2.77-2.92 (m, 3H), 2.52 (dd, J=12, J=14 Hz, 1H), 2.20 (d, J=12 Hz, 1H), 1.83-1.90 (m, 3H), 1.59-1.74 (m, 6H). 1.50 (d, J=7 Hz, 3H), 1.30 (d, J=7 Hz, 3H). ESI (MH⁺) m/z 491.

Example 51

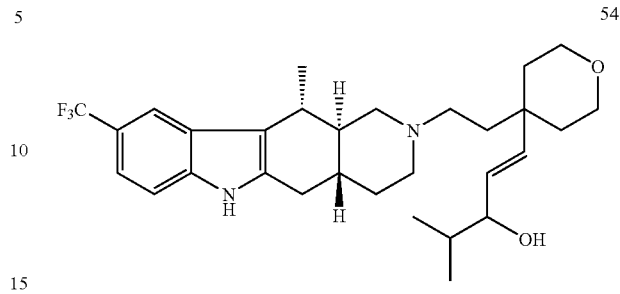

54

Obtained from treatment of aldehyde intermediate from Step 1 in Example 44 with an isopropyl Grinard. (TFA salt). ¹H NMR (400 MHz, MeOD,) δ 7.79 (s, 1H), 7.40 (d, J=8 Hz, 1H), 7.29 (d, J=8 Hz, 1H), 5.43-5.60 (m, 2H), 3.88 (m, 2H), 3.77 (m, 2H), 3.59-3.69 (m, 3H), 3.10-3.21 (m, 2H), 3.01 (t, J=14 Hz, 1H). 2.80-2.92 (m, 3H), 2.52 (dd, J=12, J=14 Hz, 1H), 2.20 (d, J=12 Hz, 1H), 1.63-1.93 (m, 10H), 1.49 (d, J=7 Hz, 3H), 0.97 (d, J=6 Hz, 3H), 0.94 (d, J=6 Hz, 3H). ESI (MH⁺) m/z 519.

Example 52

55

Obtained from treatment of aldehyde intermediate from Step 1 in Example 44 with a t-butyl Grinard. (TFA salt). ¹H NMR (400 MHz, MeOD,) δ 7.79 (s, 1H), 7.40 (d, J=8 Hz, 1H), 7.29 (d, J=8 Hz, 1H), 5.65 (dd, J=7, J=16 Hz, 1H), 5.51 (d, J=16 Hz, 1H), 3.85 (m, 1H), 3.78 (m, 3H), 3.59-3.69 (m, 3H), 3.10-3.21 (m, 2H), 3.02 (t, J=14 Hz, 1H), 2.80-2.93 (m, 3H), 2.53 (dd, J=12, J=14 Hz, 1H), 2.19 (d, J=12 Hz, 1H), 1.80-1.90 (m, 3H), 1.62-1.77 (m. 6H), 1.50 (d, J=7 Hz, 3H), 0.96 (s, 9H). ESI (MH⁺) m/z 533.

Example 53

56

Lithium hydroxide (30 mg, 1.3 mmol) was added to a THF/water solution (1:1, 0.2 M) containing ester intermediate from Example 44 (0.54 g, 1.0 mmol) and heated at reflux for 3 h. After cooling to room temperature, the solution was titrated with a 3 N HCl solution to neutral pH and concentrated to dryness using reduced pressure. This material was used in the next step without purification. ESI (MH$^+$) m/z 491.

General synthesis for analogs amide formation. HBTU (3 equiv.) was added to a dichloromethane solution (0.2 M) containing, triethylamine (3 equiv.), acid intermediate from above(1 equiv.), and the respective amine (2 equiv.) at room temperature. After stirring overnight the solvent was removed using evaporation, and the remaining residue was purified using preparative HPLC (C18 column, 10%-90% acetonitrile/water gradient).

R=Et, (TFA Salt). $^1$H NMR (400 MHz, MeOD,) δ 7.79 (s, 1H), 7.40 (d, J=8 Hz, 1H), 7.29 (d, J=8 Hz, 1H), 6.62 (d, J=16 Hz, 1H), 6.03 (d, J=16 Hz, 1H), 3.89 (d, J=10 Hz, 1H), 3.79(m, 2H), 3.50-3.73 (m, 4H), 3.13-3.21 (m, 2H), 3.02 (m, 1H), 2.80-3.0 (m, 3H), 2.53 (dd, J=12, J=14 Hz, 1H), 2.20 (d, J=12 Hz, 1H), 1.90-2.0 (m, 3H), 1.60-1.87 (m. 7H), 1.50 (m, 4H), 1.57 (t, J=7 Hz, 3H). ESI (MH$^+$) m/z 518.5.

Example 54

57

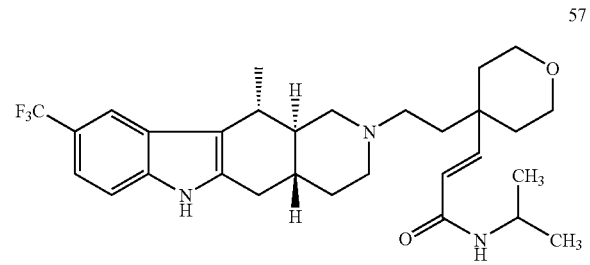

(TFA salt). $^1$H NMR (400 MHz, MeOD,) δ 7.79 (s, 1H), 7.40 (d, J=8 Hz, 1H), 7.29 (d, J=8 Hz, 1H), 6.63 (d, J=16 Hz, 1H), 6.02 (d, J=16 Hz, 1H), 4.06 (qn, J=7 Hz, 1H), 3.84 (d, J=10 Hz, 1H), 3.70 (m, 2H), 3.56-3.69 (m, 3H), 3.10-3.19 (m, 2H), 3.02 (t, J=14 Hz, 1H), 2.80-2.93 (m, 3H), 2.52 (dd, J=12, J=14 Hz, 1H), 2.19 (d, J=12 Hz, 1H), 1.62-1.99 (m. 9H), 1.50 (d, J=7 Hz, 3H), 1.19 (d, J=7 Hz, 6H). ESI (MH$^+$) m/z 532.5.

Example 55

58

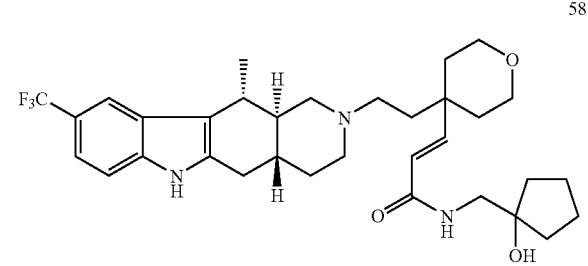

(TFA salt) $^1$H NMR (400 MHz, MeOD,) δ 7.76 (s, 1H), 7.35 (d, J=8 Hz, 1H), 7.24 (d, J=8 Hz, 1H), 6.70 (d, J=16 Hz, 1H), 6.07 (d, J=16 Hz, 1H), 3.76 (m, 2H), 3.58 (t, J=9 Hz, 2H), 3.40 (s, 2H), 3.31 (m, 1H), 3.02 (d, J=10 Hz, 1H), 2.75 (dd, J=3 Hz, J=16 Hz, 1H), 2.64 (qn, J=7 Hz, 1H), 2.40 (m, 3H), 2.04 (t, J=10 Hz, 1H), 1.69-1.93 (m, 9H), 1.63 (m, 6H), 1.49 (m, 2H), 1.43 (d, J=7 Hz, 3H), 1.34 (m, 1H). ESI (MH$^+$)m/z 588.

Example 56

59

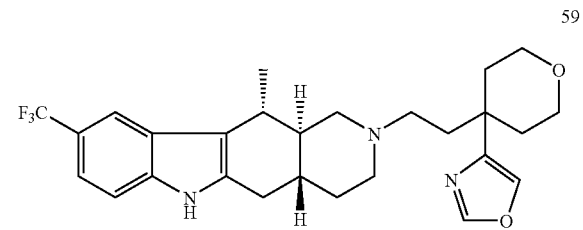

Tosylmethyl isocyanide (22 mg, 0.1 mmol) was added to a methanol solution (5 mL) containing potassium carbonate (19 mg, 1.2 mmol) and aldehyde intermediate from Step 2 of Example 44 (50 mg, 0.1 mmol). The solution was heated at reflux for 24 h. After cooling, the product was purified using preparative HPLC (C18 column, 10%-90% acetonitrile/water gradient): $^1$H NMR (400 MHz, MeOD,) δ 8.23 (s, 1H), 7.75 (s, 1H), 7.39 (d, J=8 Hz, 1H), 7.25 (d, J=8 Hz, 1H), 7.11 (s, 1H), 7.11 (s, 1H), 3.81 (d, J=12 Hz, 3H), 3.59 (d, J=12 Hz, 1H), 3.45 (t, J=11 Hz, 2H), 2.72-3.06 (m, 6H), 2.47(dd, J=12, J=14 Hz, 1H), 2.13 (m, 4H), 1.77-1.88 (m, 3H), 1.55-1.67 (m, 2H), 1.44 (d, J=7 Hz, 3H). ESI (MH$^+$) m/z 488.

Example 57

60

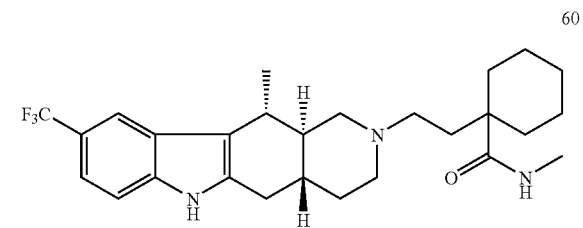

To a mixture of acid 12 (0.150 g, 0.32 mmol), DMF (2 drops) and DCM (4 mL) was added (COCl)$_2$ (1.0 mL, 2 M in DCM, 7.2 mmol). When the gas release ceased, the mixture was placed under high vacuum to obtain a solid. To this solid was added DCM (4 mL) and MeNH$_2$ (8 mL, 2 M/THF, 16 mmol). The mixture was stirred for 1 h at r.t., poured into brine and extracted with EtOAc. The organic layer was separated, washed with brine, dried with anhydrous Na$_2$SO$_4$, concentrated by rotary evaporation and purified by flash chromatography on silica gel eluted with a gradient elution of 20-40% MeOH/DCM mixed with 0-7% NH$_4$OH to yield 60 as a yellowish solid (0.095 g). MS (ES): 476 [M+H].

Example 58

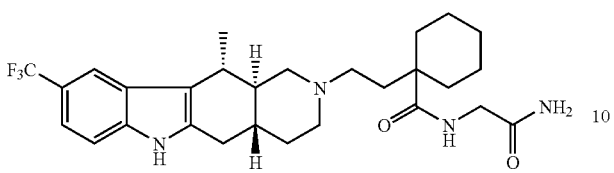

61

A mixture of acid 12 (0.926 g, 2 mmol), glycinamide HCl (0.442 g, 4 mmol), EDC.HCl (0.960 g, 5 mmol), HOBt (0.676 g, 5 mmol), NMP (2.0 mL, 18 mmol), DCM (10 mL) and DMF (10 mL) was stirred at r.t. for 3 h. The mixture was poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 20-40% MeOH/DCM mixed with 1-8% NH$_4$OH to yield 61 as a brownish solid (0.650 g). $^1$H NMR δ (DMSO, 500 MHz): 11.19 (s, 1H), 7.89 (t, J=7.5 Hz, 1H), 7.78 (s, 1H), 7.43 (d, J=8.5 Hz, 1H), 7.28 (d, J=8.5 Hz, 1H), 7.20 (s, 1H), 6.97 (s, 1H), 3.66 (m, 4H), 3.39 (m, 2H), 3.24 (m, 1H), 3.29 (m, 1H), 2.74 (m, 1H), 2.60 (m, 1H), 2.40 (m, 1H), 2.28 (m, 2H), 2.12 (m, 1H), 2.03 (m, 2H), 1.89 (m, 1H), 1.80 (m, 1H), 1.71 (m, 2H), 1.63 (m, 1H), 1.42 (m, 5H), 1.38 (d, J=6.5 Hz, 3H), 1.27 (m, 1). MS (ES): 519 [M+H].

Example 59

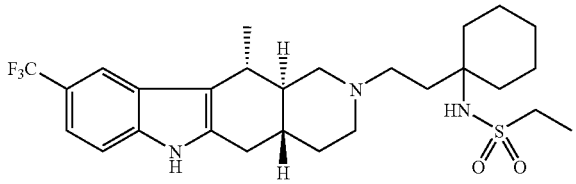

62

The corresponding amine compound was prepared following the same procedures as depicted for Example 15, with the exception of substituting 4-allyl-tetrahydropyran carboxylic acid methyl ester with 1-allyl-1-cyclohexyl carboxylic acid methyl ester.

A mixture of this amine (0.235 g, 0.54 mmol), EtSO$_2$Cl (0.139 g, 1.08 mmol), TEA (0.109 g, 1.08 mmol) in DCM (5 mL) was stirred at r.t. for 45 min. The mixture was poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 20% MeOH/DCM mixed with 0-1% NH$_4$OH to yield 62 as a solid (0.037 g). $^1$H NMR δ (DMSO, 500 MHz): 11.20 (s, 1H), 7.79 (s, 1H), 7.44 (d, J=8.5 Hz, 1H), 7.29 (d, J=8.5 Hz, 1H), 7.16 (s, 1H), 3.33 (m, 2H), 3.00 (m, 3H), 2.74 (m, 1H), 2.63 (m, 1H), 2.37-2.55 (m, 4H), 1.95 (m, 1H), 1.84 (m, 6H), 1.72 (m, 1H), 1.55 (m, 2H), 1.40 (m, 6H), 1.39 (d, J=6.5 Hz, 3H), 1.25 (t, J=7.2 Hz, 3H). MS (ES): 526 [M+H].

Example 60

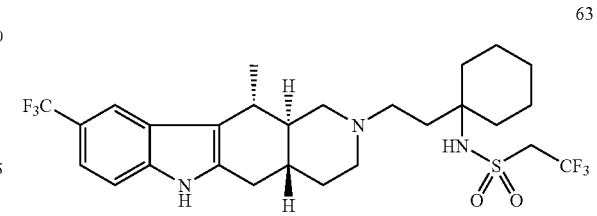

63

A mixture of amine intermediate from Example 59 (0.056 g, 0.13 mmol), CF$_3$CH$_2$SO$_2$Cl (0.036 g, 0.15 mmol), TEA (0.042 mL, 0.3 mmol) in DCM (1 mL) was stirred at r.t. for 15 min. The mixture was poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 20% MeOH/DCM mixed with 0-1% NH$_4$OH to yield 63 as a solid (0.030 g). $^1$H NMR δ (DMSO, 500 MHz): 11.20 (s, 1H), 8.19 (s, 1H), 7.79 (s, 1H), 7.44 (d, J=8.5 Hz, 1H), 7.28 (d, J=8.5 Hz, 1H), 4.31 (m, 2H), 3.28 (m, 2H), 2.97 (m, 1H), 2.75 (m, 1H), 2.63 (m, 1H), 2.48 (m, 2H), 2.37 (m, 1H), 1.95 (m, 1H), 1.84 (m, 5H), 1.74 (m, 1H), 1.5-1.68 (m, 5H), 1.2-1.5 (m, 6H), 1.38 (d, J=6.5 Hz, 3H). MS (ES): 580 [M+H].

Example 61

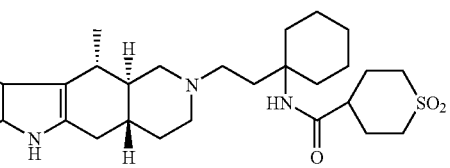

64

A mixture of amine intermediate from Example 59 (0.097 g, 0.224 mmol), 4,4-dioxo-tetrahydrothiopyranyl carboxylic acid (0.040 g, 0.224 mmol), EDC.HCl (0.107 g, 0.56 mmol), HOBt (0.076 g, 0.56 mmol), NMP (0.275 mL, 2.5 mmol), DCM (1.5 mL) and DMF (1.5 mL) was stirred at r.t. overnight. The mixture was poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 10-20% MeOH/DCM mixed with 0-3% NH$_4$OH to yield 64 as a white solid (0.023 g). $^1$H NMR δ (DMSO, 500 MHz): 11.25 (s, 1H), 7.79 (s, 1H), 7.45 (d, J=8.5 Hz, 1H), 7.29 (d, J=8.5 Hz, 1H), 3.13 (m, 5H), 2.78 (m, 2H), 2.64 (m, 1H), 2.55 (m, 1H), 2.43 (m, 2H), 2.08 (m, 1OH), 1.2-1.55 (m, 16H). MS (ES): 594 [M+H].

Example 62

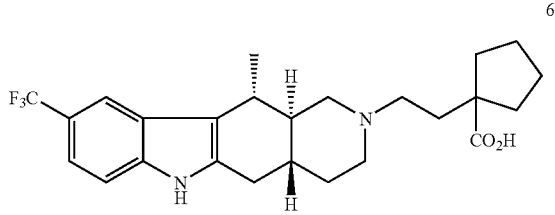

65

Synthesized according to the same sequence as used for the synthesis of compound in Example 4. $^1$H NMR δ (DMSO, 500 MHz): 11.20 (s, 1H), 7.78 (s, 1H), 7.44 (d, J=8.5 Hz, 1H), 7.29 (d, J=8.5 Hz, 1H), 3.58 (s, 1H), 3.30 (m, 2H), 2.97 (m, 1H), 2.75 (m, 1H), 2.61 (m, 1H), 2.39 (m, 3H), 2.02 (m, 3H), 1.80 (m, 4H), 1.59 (m, 4H), 1.45 (m, 3H), 1.38 (d, J=6.5 Hz, 3H), 1.32 (m, 1H). MS (ES): 449 [M+H].

Example 63

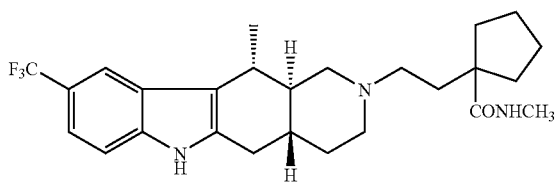

66

To a mixture of acid 65 (0.070 g, 0.15 mmol), DMF (1 drop) and DCM (2 mL) was added (COCl)$_2$ (0.5 mL, 2 M in DCM, 1 mmol). When the gas release ceased, the mixture was placed under high vacuum to obtain a solid. To this solid was added DCM (2 mL), MeNH$_2$(2 mL, 2 M in THF, 2 mmol). The mixture was stirred at r.t. for 1 h, poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel eluted with a gradient elution of 5-30% MeOH/DCM mixed with 0-5% NH$_4$OH to yield 66 as a white solid (0.060 g). $^1$H NMR δ (DMSO, 500 MHz): 11.21 (s, 1H), 7.79 (s, 1H), 7.59 (s, 1H), 7.44 (d, J=8.5 Hz, 1H), 7.29 (d, J=8.5 Hz, 1H), 2.76 (m, 1H), 2.55 (m, 1H), 2.60 (d, J=4.0 Hz, 3H), 2.41 (m, 2H), 2.19 (m, 1H), 2.01 (m, 2H), 1.81 (m, 4H), 1.33-1.58 (m, 1OH), 1.39 (d, J=6.5 Hz, 3H). MS (ES): 462 [M+H].

Example 64

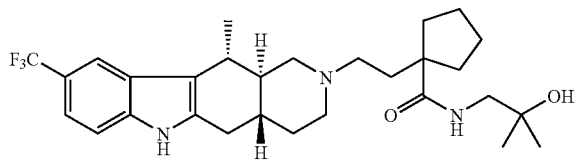

67

A mixture of acid 65 (0.100 g, 0.22 mmol), 2-aminomethyl-2-propanol (0.120 g, 0.67 mmol), EDC.HCl (0.127 g, 0.66 mmol), HOBt (0.089 g, 0.66 mmol), NMP (0.25 mL, 2.3 mmol), DCM (2 mL) and DMF (2 mL) was stirred at r.t. overnight. The mixture was poured into saturated NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 10-20% MeOH/DCM mixed with 1-2% NH$_4$OH to yield 67 as a white solid (0.100 g). MS (ES): 520 [M+H].

Example 65

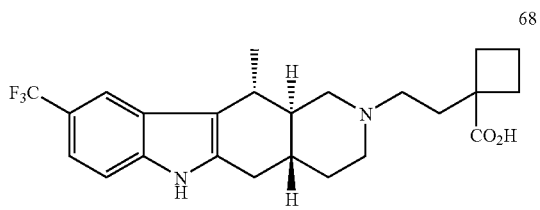

68

Synthesized according to the same sequence as was used for the synthesis of compound 12 (Example 9). $^1$H NMR δ (DMSO, 500 MHz): 11.21 (s, 1H), 7.78 (s, 1H), 7.44 (d, J=8.5 Hz, 1H), 7.29 (d, J=8.5 Hz, 1H), 3.31 (m, 2H), 2.99 (m, 1H), 2.75 (m, 1H), 2.61 (m, 1H), 2.37 (m, 6H), 1.8-2.05 (m, 8H), 1.25-1.50 (m, 6H). MS (ES): 435 [M+H].

Example 66

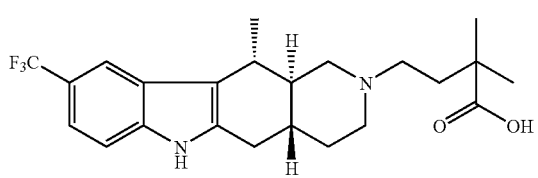

69

Synthesized according to the same sequence as was used for the synthesis of example 2 $^1$H NMR (400 MHz, CD$_3$OD) δ 7.78 (s, 1H), 7.39 (d, J=8.0 Hz, 1H), 7.27 (d, J=8.0 Hz, 1H), 3.75 (m, 1H), 3.40 (m, 1H), 3.14 (m, 2H), 3.00 (m, 2H), 2.60(m, 1H), 2.40-2.50 (m, 4H), 1.50-2.00 (m, 4H) 1.44 (d, J=6.4 Hz, 3H), 1.22 (s, 6H). ESI (MH$^+$) m/z 423.

Example 67

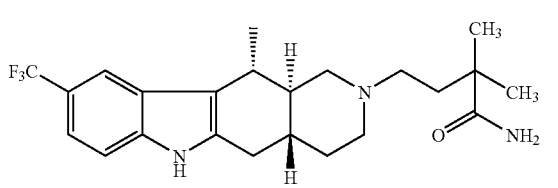

70

Compound 69 from Example 66 (1.03 g, 2.43 mmol) in 5 mL DCM was treated with oxalyl chloride (2.1 mL, 24.3 mmol) and two drops of dry DMF. After 30 min., the reaction was brought to dryness under low pressure. DCM (15 mL) was added and the flask was put into an ice bath. Much excess ammonia in dry DCM was added slowly to react with the previously formed carbonyl chloride. In around 20 min., the reaction showed completion by LC-MS. Water (30 mL) was added and the aqueous layer was extracted with DCM (3×20 mL). The organic layers were combined, dried and concentrated. Purification by flash chromatography on silica gel with 5-10% MeOH/DCM afforded 70 (800 mg, 1.90 mmol) as light brown film. $^1$H NMR (400 MHz, CD$_3$OD) δ 7.78 (s, 1H), 7.39 (d, J=8.0 Hz, 1H), 7.26 (d, J=8.0 Hz, 1H), 3.77 (m, 1H), 3.41 (m, 1H), 2.98 (m, 2H), 2.55(m, 1H), 2.10-2.50 (m, 4H), 1.45-2.00 (m, 4H) 1.41 (d, J=6.4 Hz, 3H), 1.21 (s, 6H). ESI (MH$^+$) m/z 422.

Example 68

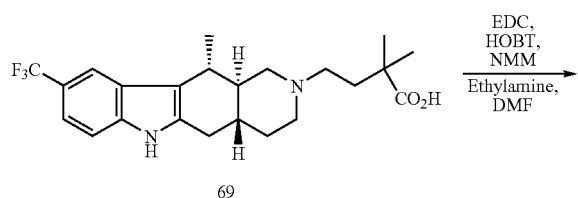

69

-continued

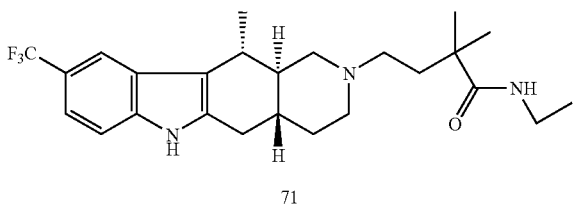

71

The mixture of the acid 69 (Example 66) (50 mg, 0.118 mmol), EDC (68 mg, 0.354 mmol), HOBT (16 mg, 0.118 mmol), NMM (0.039 mL, 0.354 mmol) and excess ethylamine (~10 equiv.) in 2 mL DCM was stirred at room temperature overnight. The solvent was removed under vacuum and 1 mL DMF and 0.2 mL water were added. The solution was injected directly to HPLC (reverse phase) to render 30 mg (0.066 mmol) of 71 as yellow film. $^1$H NMR (400 MHz, CD$_3$OD) δ 7.77 (s, 1H), 7.37 (d, J=8.4 Hz, 1H), 7.26 (d, J=8.4 Hz, 1H), 3.30 (m, 2H), 3.21 (q, J=7.2 Hz, 1H), 3.10-3.20 (m, 4H), 2.55(m, 1H), 2.15-2.50 (m, 4H), 1.50-2.00 (m, 4.44 (d, J=6.4 Hz, 3H), 1.22 (s, 6H), 1.13 (t, J=7.2 Hz, 3H). ESI (MH$^+$) m/z 450.

Example 69

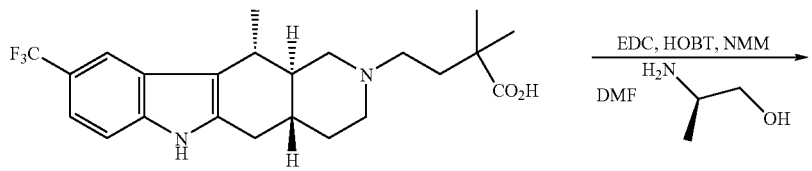

T0918766
69

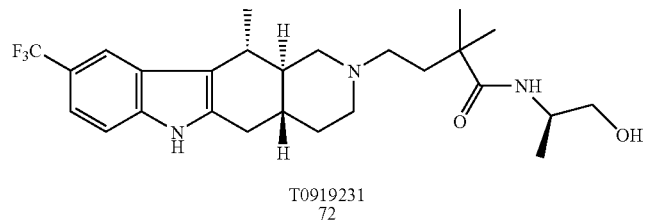

T0919231
72

Compound 72 was prepared following same procedures as described for Example 67. $^1$H NMR (400 MHz, CD$_3$OD) δ 7.79 (s, 1H), 7.39 (d, J=8.4 Hz, 1H), 7.28 (d, J=8.4 Hz, 1H), 7.07 (d, J=8.4 Hz, 2H), 6.75 (d, J=8.4 Hz, 2H), 3.82 (m, 1H), 3.61 (m, 1H), 3.20 (m, 2H), 2.65-3.00 (m, 6H), 2.50 (m, 1H), 2.15 (m, 3H),1.60-1.90 (m, 3H) 1.45 (d, J=6.4 Hz, 3H). ESI (MH$^+$) m/z 443.

Example 70

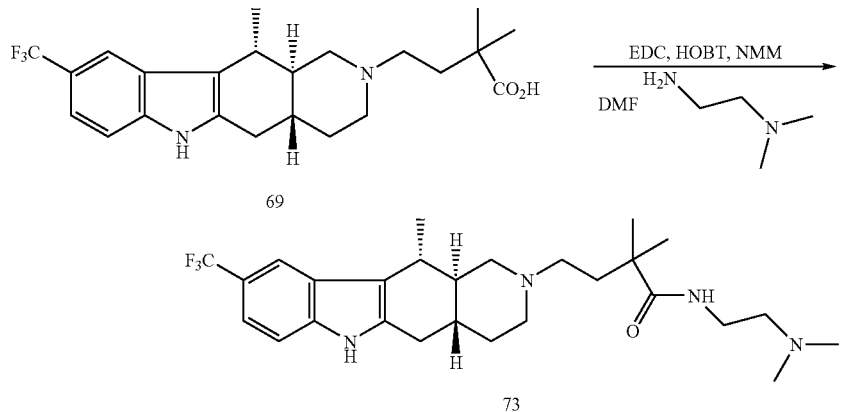

The same procedure was followed as for compound 71 (Example 68). $^1$H NMR (400 MHz, CD$_3$OD) δ 7.78 (s, 1H), 7.39 (d, J=8.4 Hz, 1H), 7.29 (d, J=8.4 Hz, 1H), 3.90 (m, 1H), 3.70 (m, 1H), 3.5 (m, 2H), 3.30 (m, 3H), 2.95 (s, 6H), 2.50-2.90 (m, 5H), 2.50 (m, 1H), 2.00-2.20 (m, 4H), 1.60-1.90 (m, 2H) 1.49 (d, J=6.8 Hz, 3H), 1.27 (s, 6H). ESI (MH$^+$) m/z 493.

Example 71

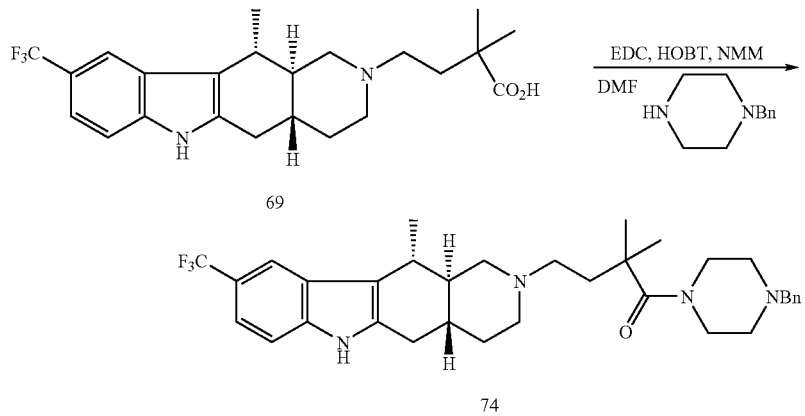

The same procedure was followed as for compound 71 (Example 68). $^1$H NMR (400 MHz, CD$_3$OD) δ 7.77 (s, 1H), 7.38 (d, J=8.4 Hz, 1H), 7.27 (d, J=8.4 Hz, 1H), 7.20-7.40 (m, 5H), 3.90 (m, 1H), 3.70 (br, 2H), 3.30-3.65 (m, 8H), 3.20 (m, 2H), 2.50-2.90 (m, 5H), 2.50 (m, 1H), 2.00-2.20 (m, 3H), 1.60-1.90 (m, 3H) 1.49 (d, J=6.8 Hz, 3H), 1.27 (s, 6H). ESI (MH$^+$) m/z 582.

Example 72

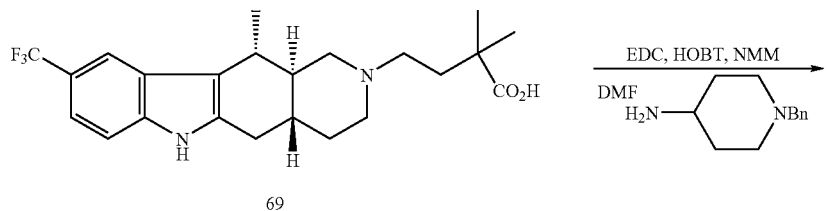

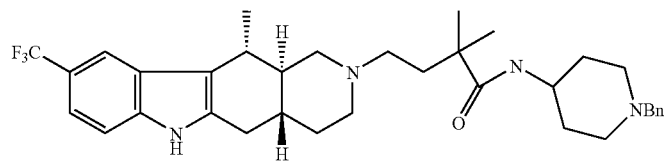

The same procedure was followed as for compound 71 (Example 68). $^1$H NMR (400 MHz, CD$_3$OD) δ 7.77 (s, 1H), 7.38 (d, J=8.4 Hz, 1H), 7.27 (d, J=8.4 Hz, 1H), 7.20-7.40 (m, 5H), 3.88 (m, 1H), 3.69 (br, 2H), 3.30-3.65 (m, 5H), 3.21 (m, 2H), 2.50-2.90 (m, 5H), 2.50 (m, 1H), 2.00-2.20 (m, 4H), 1.60-1.90 (m, 6H) 1.48 (d, J=6.8 Hz, 3H), 1.26 (s, 6H). ESI (MH$^+$) m/z 596.

Example 73

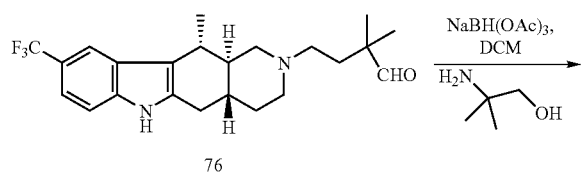

Compound 76 was prepared by reducing compound 69 and oxidizing the corresponding alcohol with SO$_3$.pyridine in DMSO/TEA as described in Example 44. To the solution of compound 76 (25 mg, 0.061 mmol) in 2 mL DCM was added NaBH(OAc)$_3$ (26.0 mg, 0.122 mmol) followed by the addition of amine (11 mg, 0.122 mmol). The reaction mixture was kept stirring for overnight. The solvent was removed and 1 mL DMF was added to dissolve the mixture. After filtration, the solution was injected directly to reverse HPLC to render pure yellow film 77 (18 mg, 0.038 mmol) as the product. $^1$H NMR (400 MHz, CD$_3$OD) δ 7.78 (s, 1H), 7.40 (d, J=8.4 Hz, 1H), 7.30 (d, J=8.4 Hz, 1H), 3.93 (m, 1H), 3.68 (m, 1H), 3.60 (s, 2H), 3.30-3.40 (m, 4 H),2.75-3.10(m, 4H), 2.50(m, 1H),2.00-2.20(m,3H), 1.60-1.90(m,3H) 1.49 (d, J=6.4 Hz, 3H), 1.38 (s, 6H), 1.14 (s, 6H). ESI (MH$^+$) m/z 480.

Example 74

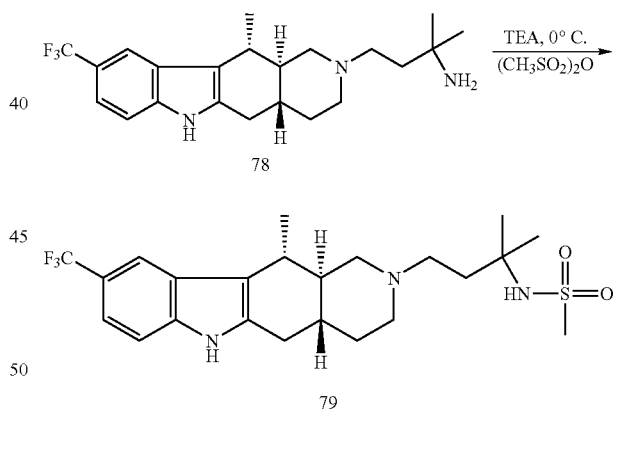

Compound 78 was obtained in several steps following a sequence similar to that of Example 10. At 0° C., to the solution of compound 78 (6 mg, 0.015 mmol) and triethylamine (6 mg, 0.06 mmol), was added methansulfonic anhydride (7.8 mg, 0.045 mmol). The reaction was kept stirring for overnight. The solvent was removed under vacuum and the resulted residue was subjected to reverse HPLC to render pure yellow solid 79 (2.0 mg, 0.004 mmol). $^1$H NMR (400 MHz, CD3OD) δ 7.78 (s, 1H), 7.40 (d, J=8.4 Hz, 1H), 7.30 (d, J=8.4 Hz, 1H), 3.50-3.70 (m, 2H), 3.00-3.30 (m, 3H), 2.70 (s, 3H), 2.60-3.00 (m, 4H), 1.60-2.20 (m, 6 H), 1.47 (d, J=6.4 Hz, 3H), 1.20 (s, 6H). ESI (MH$^+$) m/z 472.

Example 75

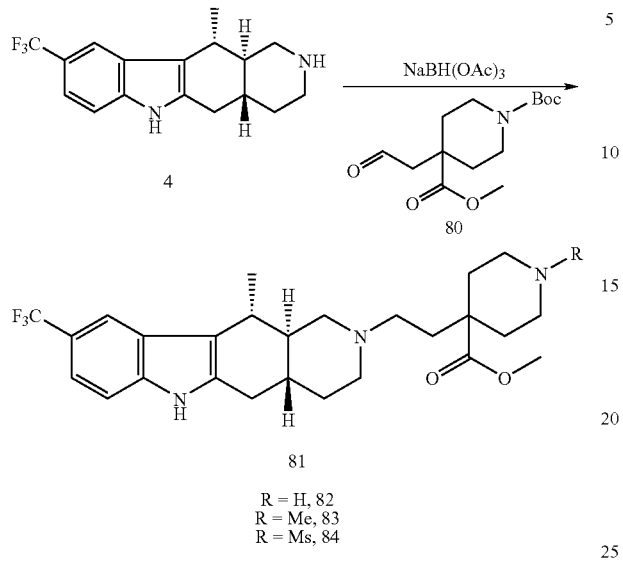

R = H, 82
R = Me, 83
R = Ms, 84

A mixture of amine 4 (0.9 g, 2.92 mmol), sodium triacetoxborohydride (2.5 g, 11.7 mmol) and aldehyde 80 (1.0 g, 3.5 mmol) in DCE (0.25 M solution) was stirred at room temperature for 3 h. The reaction mixture was treated with saturated sodium bicarbonate solution and extracted with ethyl acetate, the organic layer was washed with brine and dried, concentrated and purified by flash chromatography on silica gel eluted with 3% MeOH/DCM to yield 81 as yellow solid (0.73 g). Compound 81 was treated with trifloroacetic acid in DCM for 0.5 h, concentrated and purified by flash chromatography on silica gel eluted with 20:1:0.1 DCM:MeOH:NH$_4$OH to yield 82 as pale yellow solid (0.49 g). $^1$H NMR (400 MHz, DMSO) δ 11.2 (s, 1H), 8.03 (s, 1H), 7.41 (d, J=8.4 Hz, 1H), 7.25 (d, J=8.4 Hz, 1H), 3.64 (s, 3H), 3.2 (dd, J=2.4 Hz, J=9.2 Hz, 1H), 2.86 (m, 2H), 2.84 (dd, J=2.4 Hz J=9.2 Hz, 1H), 2.50-2.75 (m, 4H), 2.10-2.45 (m, 4H), 2.0 (d, J=12 Hz ,2H), 1.55-1.90 (m, 5H), 1.47 (m, 2 H), 1.35-1.4 (m, 2H), 1.35 (d, J=6.6 Hz, 3H), 1.25 (m, 1H). ESI (MH$^+$) m/z 478.

Compound 82 (0.1 g, 0.21 mmol) was treated with formaldehyde (0.01 g, 0.3 mmol) and sodium triacetoxborohydride (0.178 g, 0.84 mmol) in DCE for 3 h. at room temperature. The reaction was treated with saturated sodium bicarbonate solution and extracted with ethyl acetate, the organic layer was washed with brine and dried, concentrated and purified by flash chromatography on silica gel eluted with 20:1:0.1 DCM:MeOH:NH$_4$OH to yield 83 as yellow solid (0.01 g). $^1$H NMR (400 MHz, CDCl$_3$) δ 7.93 (s, 1H), 7.84 (s, 1H), 7.33 (s, 2H), 3.71 (s, 3H), 3.4 (d, J=6.4 Hz, 1 H), 2.96 (d, J=6.4 Hz, 1H), 2.67 (m, 4H), 2.47 (dd, J=8.0 Hz J=12 Hz, 1H), 2.10-2.40 (m, 7H), 1.45-1.95 (m, 11H), 1.35 (d, J=6.6 Hz, 3H). ESI (MH+) m/z 492.

Compound 82 (0.05 g, 0.105 mmol) was treated with mesyl chloride (0.012 g, 0.105 mmol) and triethylamine (0.013 g, 0.013 mmol) in DCM for 2 h. at 0° C. The reaction was treated with saturated sodium bicarbonate solution and extracted with ethyl acetate, the organic layer was washed with brine and dried, concentrated and purified by flash chromatography on silica gel eluted with 20:1:0.1 DCM: MeOH:NH4OH to yield 84 as yellow solid (0.055 g). $^1$H NMR (400 MHz, CDCl3) δ 8.10 (s, 1H), 7.86 (s, 1H), 7.32 (s, 2H), 3.74 (s, 3H), 3.63 (d, J=9.5 Hz, 1 H), 2.93 (d, J=9.5 Hz, 1H), 2.60-2.80 (m, 7H), 2.20-2.50 (m, 5H), 1.96 (t, J=10.8 Hz, 1H), 1.8 (m, 4H), 1.73 (t, J=7.8 Hz, 1H), 1.60 (t, J=12 Hz, 2H), 1.30-1.50 (m, 3H), 1.35 (d, J=6.6 Hz, 3H). ESI (MH$^+$) m/z 556.

Example 76

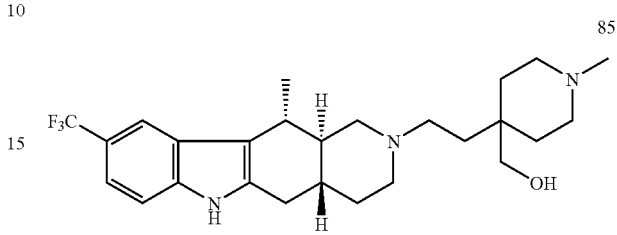

Compound 83 (0.02 g, 0.04 mmol) was treated with lithium aluminumhydride (0.02 g, 0.042 mmol) in THF for 2 h. at room temperature. The reaction was treated with saturated sodium bicarbonate solution and extracted with ethyl acetate, the organic layer was washed with brine and dried, concentrated and purified by flash chromatography on silica gel eluted with 20:1:0.1 DCM:MeOH:NH$_4$OH to yield 85 as yellow solid (0.055 g). $^1$H NMR (400 MHz, CDCl$_3$) δ 8.1 (s, 1H), 7.80 (s,1H), 7.33 (s, 2H), 3.41 (s, 3H), 3.15 (d, J=10.5 Hz, 1 H), 2.35-2.65 (m, 7H), 2.67 (m, 4H), 2.05 (m, 2H), 1.5-1.9 (m, 12H), 1.40 (d, J=6.6 Hz, 3H). ESI (MH$^+$) m/z 464.

Example 77

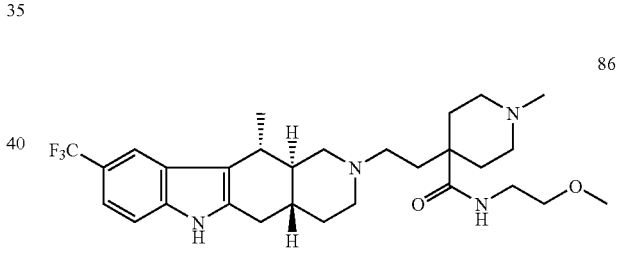

Compound 83 (4 g, 8.15 mmol) was treated with lithium hydroxide (0.391 g, 16.3 mmol) in THF, MeOH and water reflux overnight. The reaction was treated with 1 N HCl solution and extracted with isopropyl alcohol and chloroform, the organic layer was washed with brine and dried, concentrated and purified by flash chromatography on silica gel eluted with 10:1:0.1 DCM:MeOH:HOAc to yield 2 g pink powder (acid). The acid (0.052 g, 0.11 mmol) was reacted with 2-methoxyethylamine (0.0098 g, 0.13 mmol), under the condition of EDC (0.063 g, 0.33 mmol), HOBt (0.0147 g, 0.11 mmol), and NMM (0.033 g, 0.33 mmol) in DMF (1 mL) at room temperature overnight. The reaction was treated with saturated sodium bicarbonate solution and extracted with ethyl acetate, the organic layer was washed with brine and dried, concentrated and purified by flash chromatography on silica gel eluted with 20:1:0.1 DCM: MeOH:NH$_4$OH to yield 86 as brown oil (0.003 g). $^1$H NMR (400 MHz, CDCl$_3$) δ 8.05 (s, 1H), 7.83 (s, 1H), 7.34 (s, 2H), 3.48 (s, 3H), 3.35 (s, 3H), 3.05 (d, J=11.2 Hz, 1H), 2.88 (m, 2H), 2.60-2.75 (m, 3H), 2.35-2.55 (m, 9H), 2.05 (m, 2H), 1.48-1.60 (m, 5H), 1.22 (s, 6H), 0.85 (m, 2H). ESI (MH$^+$) m/z 464.

Example 78

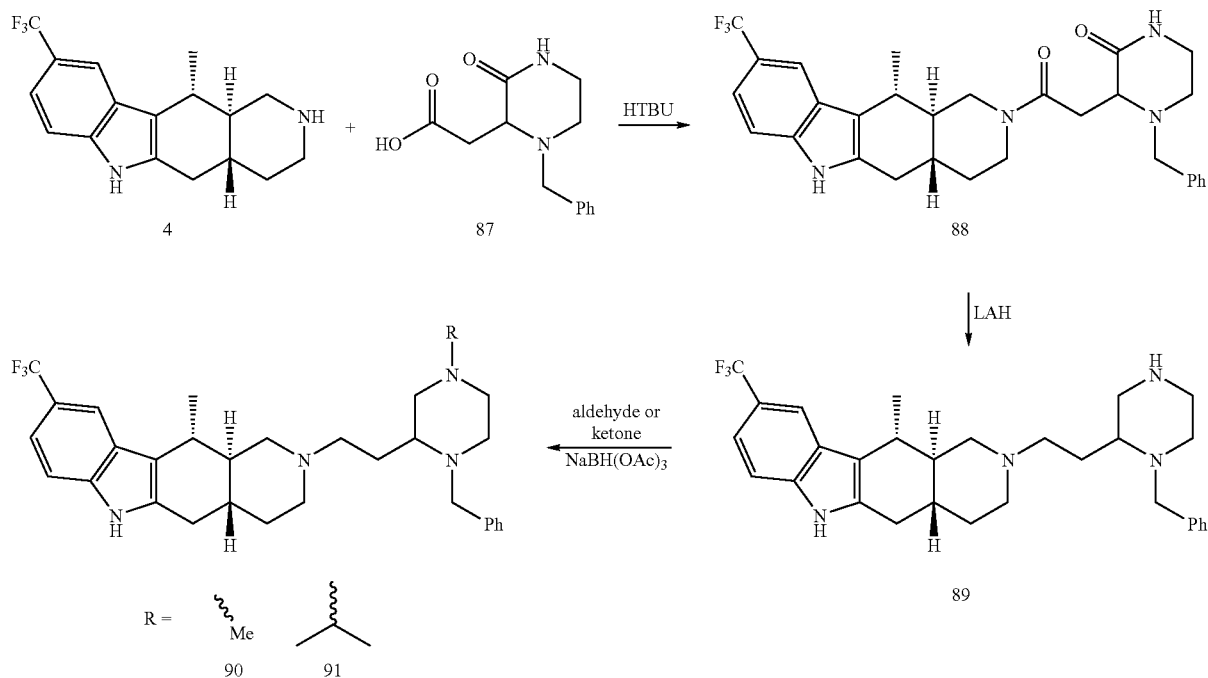

Intermediate 88. EDC (1.12 g, 5.9 mmol) was added to a dichloromethane solution (0.2 M) containing, triethylamine (1 mL.), amine 4 (1.2 g, 3.9 mmol), and the carboxylic acid 87 (0.97 g, 3.9 mmol) at room temperature. After stirring overnight the mixture was washed with water, dried over $Na_2SO_4$, and concentrated to give intermediate 88. This material was used in the next step without purification. ESI (MH$^+$) m/z 539.

Analog 89 (TFA Salt). LAH (200 mg) was added to a dry THF solution (10 mL) containing 88 (2.0 g, 3.9 mmol) at room temperature. The solution was heated at reflux for 2 h. After heating, water (0.2 mL) was added followed by a 1 N solution of NaOH (0.2 mL), and a final addition of water (0.4 mL). The resulting solid was filtered washed with copious amounts of dichloromethane. A portion of this material was purified by using preparative HPLC (C18 column, 10%-90% acetonitrile/water 15 gradient). $^1$H NMR (400 MHz, MeOD) δ 7.79 (s, 1H), 7.36-7.42 (m, 5H), 7.25-7.32 (m, 2H), 4.14 (d, J=13 Hz, 1H), 3.90 (t, J=11 Hz, 1H), 3.67 (d, J=11 Hz, 1H) 3.32-3.52 (m, 3H), 2.81-3.14 (m, 8H), 2.53 (m, 2H), 2.19-2.31 (m, 3H), 1.66-1.89 (m, 3H), 1.50 (m, 3H). ESI (MH$^+$) m/z 511.

General synthesis for analogs 90 and 91. Sodium triacetoxyborohydride (3 equiv.) was added to a dichloromethane solution (0.2 M) containing amine 89 (1 equiv.) and the respective ketone or aldehyde (3 equiv.) at room temperature. After stirring overnight the solvent was removed using evaporation, and the remaining residue was purified using preparative HPLC (C18 column, 10%-90% acetonitrile/water gradient).

Analog 90 (TFA Salt). $^1$H NMR (400 MHz, MeOD) δ 7.79 (s, 1H), 7.36-7.42 (m, 5H), 7.25-7.32 (m, 2H), 4.14 (d, J=13 Hz, 1H), 3.86 (t, J=11 Hz, 1), 3.62(d,J=11 Hz, 1H) 3.32-3.52(m, 3H),2.81-3.14(m, 13H),2.51 (dd, J=12, J=14 Hz, 2H), 2.20 (m, 3H), 1.68-1.87 (m, 3H), 1.50 (m, 3H); ESI (MH$^+$) m/z 525.

Analog 29 (TFA Salt). $^1$H NMR (400 MHz, MeOD) δ 7.79 (s, 1H), 7.36-7.42 (m, 5H), 7.25-7.32 (m, 2H), 4.14 (d, J=13 Hz, 1H), 3.86 (t, J=11 Hz, 1H), 3.62 (d, J=11 Hz, 1H 3.32-3.52 (m, 5H), 2.81-3.14 (m, 8H), 2.51 (m, 3H), 2.20 (m, 2H), 1.68-1.87 (m, 4H), 1.50 (m, 3H), 1.42 (m, 6H). ESI (MH$^+$) m/z 553.

Example 79

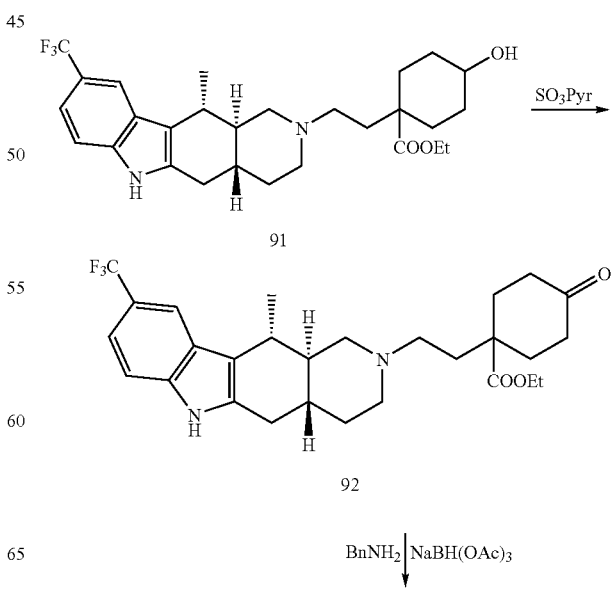

-continued

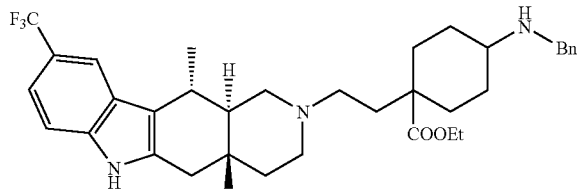

93

Analog 91 (TFA Salt). $^1$H NMR (400 MHz, MeOD) δ 7.79 (s, 1H), 7.40 (d, J=8 Hz, 1H), 7.29 (d, J=8 Hz, 1H), 4.25 (q, J=7 Hz, 2H), 3.88 (d, J=12 Hz, 1H), 3.67 (d, J=12 Hz, 1H), 3.57 (m, 1H), 3.10-3.21 (m, 2H), 3.02 (t, J=14 Hz, 1H), 2.80-2.93 (m, 3H), 2.53 (dd, J=12, J=14 Hz, 1H), 2.19-2.25 (m, 3H), 1.99 (m, 2H), 1.86 (m, 3H), 1.62-1.70 (m. 2H), 1.49 (d, J=7 Hz, 3H), 1.24-1.38 (m, 7H); ESI (MH$^+$) m/z 507.

Intermediate 92. SO$_3$ pyridine complex (42 g, 2.7 mmol) was added to a DMSO/Et$_3$N (2.5:1, 0.2 M) solution containing compound 91 (0.34 g, 0.65 mmol) at room temperature. After stirring for 2 h, the mixture was poured into water (25 mL) and extracted with dichloromethane (3×75 mL). The organic layers were washed with brine, dried over Na$_2$SO$_3$, and concentrated to give intermediate 92. Compound 31 was used in the next step without purification: ESI (MH$^+$) m/z 505.

Analog 93 (TFA Salt). Sodium triacetoxyborohydride (3 equiv.) was added to a dichloromethane solution (0.1 M) containing benzylamine (2 equiv.) and the ketone 92 (1 equiv.) at room temperature. After stirring overnight the solvent was removed using evaporation, and the remaining residue was purified using preparative HPLC (C18 column, 10%-90% acetonitrile/water gradient). $^1$H NMR (400 MHz, MeOD,) δ 7.79 (s, 1H), 7.44-7.53 (m, 5H), 7.40 (d, J=8 Hz, 1H), 7.29 (d, J=8 Hz, 1H), 4.25 (m, 4H), 3.88 (t, J=15 Hz, 1H). 3.75 (d, J=14 Hz, 1H), 3.60 (d, J=14 Hz, 1H), 2.75-3.26 (m, 7H), 2.55 (m, 1H), 2.41 (m, 1H), 2.03-2.26 (m, 5H), 1.5-1.9 (m, 7H), 1.40-1.50 (m, 4H), 1.31 (m, 3H). ESI (MH$^+$) m/z 596.5.

Example 80

The MCHR modulatory activity of the compounds of the invention can be assessed using the in vitro and in vivo assay methods described above.

Exemplary in vitro methods include fluorometric imaging plate reader (FLIPR) functional assays (see, e.g., *G Protein-Coupled Receptors* (1999) pp. 105-108 (T. Haga, G. Bernstein, eds.) CRC Press; Lembo et al. (1999) *Nature Cell Biol.* 1:267-271; Saito et al. (1999) *Nature* 400:265-269; Wood et al. (2000) *Eur. J. Pharmacol.* 396:1-8 and Miller et al. (1999) *J. Biomol. Screen.* 4:249-258) and radioligand binding assays (see, e.g., *Receptor Binding Techniques* (1999) pp. 37-47 (M. Keen, ed.) Humana Press; Buckley et al. (1989) *Mol. Pharmacol.* 35:469-476; Mihara et al. (1994) *J. Pharmacol. Exp. Ther.* 268:1122-1128; Newman et al. (2000) *Eur. J. Pharmacol.* 397:255-262 and Audinot et al. (2001) *Br. J. Pharmacol.* 133:371-378).

Exemplary compounds demonstrated MCHR1 modulatory activity.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula (I):

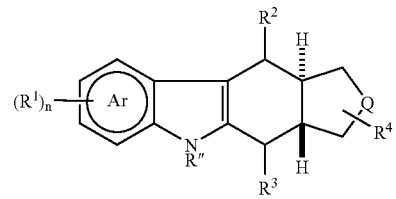

I or a pharmaceutically acceptable salt, thereof, wherein

represents a single or fused aryl or heteroaryl ring;

Q is —N(R) (C$_1$)alkylene-;

R is

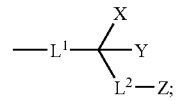

L$^1$ is a bond, (C$_1$-C$_4$)alkylene, (C$_1$-C$_4$)alkylenoxy and (C$_1$-C$_4$)alkylenamino;

L$^2$ is a bond, (C$_1$-C$_4$)alkylene, (C$_2$-C$_4$)alkenylene, (C$_2$-C$_4$)alkynylene, (C$_1$-C$_4$)alkylenoxy (e.g. —OCH$_2$CH$_2$—) or (C$_1$-C$_4$)alkylenamino (e.g. —NH—CH$_2$CH$_2$—);

R″ is hydrogen or (C$_1$-C$_8$)alkyl;

each R$^1$ is independently selected from the group consisting of halogen, (C$_1$-C$_8$)alkyl, (C$_2$-C$_8$)alkenyl, (C$_2$-C$_8$)alkynyl, fluoro(C$_1$-C$_4$)alkyl, —OR$^5$, —SR$^5$, fluoro(C$_1$-C$_4$)alkoxy, aryl, aryl(C$_1$-C$_4$)alkyl, —NO$_2$, —NR$^5$R$^6$, —C(O)R$^5$, —CO$_2$R$^5$, —C(O)NR$^5$R$^6$, —N(R$^6$)C(O)R$^5$, —N(R$^6$)CO$_2$R$^5$, —N(R$^7$)C(O)NR$^5$R$^6$, —S(O)$_m$NR$^5$R$^6$, —S(O)$_m$R$^5$, —CN and —N(R$^6$)S(O)$_m$R$^5$;

R$^2$ and R$^3$ are independently selected from the group consisting of hydrogen, halogen, (C$_1$-C$_8$)alkyl, (C$_2$-C$_8$)alkenyl, (C$_2$-C$_8$)alkynyl, fluoro(C$_1$-C$_4$)alkyl, —OR$^8$, —SR$^8$, fluoro(C$_1$-C$_4$)alkoxy, aryl, aryl(C$_1$-C$_4$)alkyl, —NO$_2$, —NR$^8$R$^9$, =O, —C(O)R$^8$, —CO$_2$R$^8$, —C(O) NR$^8$R$^9$, —N(R$^9$)C(O)R$^8$, —N(R$^9$)CO$_2$R$^8$, —N(R$^{10}$)C (O)NR$^8$R$^9$, —S(O)$_m$NR$^8$R$^9$, —S(O)$_m$R$^8$, —CN and —N(R$^9$)S(O)$_m$R$^8$;

R$^4$ is selected from the group consisting of hydrogen, —OR$^{11}$, —C(O)R$^{11}$, —CO$_2$R$^{11}$, —C(O)NR$^{11}$R$^{12}$, —CN, (C$_1$-C$_4$)alkyl and aryl;

X and Y are independently selected from the group consisting of (C$_1$-C$_8$)alkyl, (C$_2$-C$_8$)alkenyl, (C$_2$-C$_8$)alkynyl, —CO$_2$R$^{13}$ and —C(O)NR$^{13}$R$^{14}$;

optionally, X and Y may be combined to form a 3-, 4-, 5-, 6- or 7-membered ring containing from 0 to 2 heteroatoms independently selected from the group consisting of N, O and S;

Z is selected from the group consisting of —$OR^{15}$, —$NR^{15}R^{16}$, —$NR^{15}R^{18}$, —$C(O)R^{15}$, —$CO_2R^{15}$, —$R^{18}$, —$C(O)NR^{15}R^{16}$, —$C(O)NR^{15}R^{18}$, —$SO_2NR^{15}R^{16}$, —$SO_2NR^{15}R^{18}$, —$NR^{16}SO_2R^{15}$, —$N(R^{15})N(R^{16})SO_2R^{17}$, —$C(O)N(R^{16})OR^{15}$, hydroxy($C_1$-$C_8$)alkyl, fluoro($C_1$-$C_4$)alkyl, heteroaryl, —$C(=NOR^{15})NR^{16}R^{17}$, —$C(R^{16})=NOR^{15}$, —$NR^{16}(OR^{15})$, —$C(O)NR^{17}C(O)NR^{15}R^{16}$, —$NR^{17}C(O)NR^{16}C(O)R^{15}$ and —$NR^{17}C(O)NR^{15}R^{16}$;

$R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are independently selected from the group consisting of hydrogen, ($C_1$-$C_8$)alkyl, ($C_2$-$C_8$)alkenyl, ($C_2$-$C_8$)alkynyl, cyclo($C_3$-$C_6$)alkyl, fluoro($C_1$-$C_4$)alkyl, hetero($C_1$-$C_4$)alkyl, cyclohetero($C_3$-$C_6$)alkyl, aryl and aryl($C_1$-$C_4$)alkyl;

$R^{18}$ is a 5- or 6-membered ring containing from 0 to 4 heteroatoms selected from the group consisting of N, O and S;

optionally, when two variables selected from the group of variables consisting of $R^5$, $R^6$, $R^8$, $R^9$, $R^{11}$, $R^{12}$, $R^{13}$, $R^{14}$, $R^{15}$, $R^{16}$ and $R^{17}$ are attached to the same nitrogen atom, the two variables may be combined to form a 3-, 4-, 5-, 6- or 7-membered ring containing the nitrogen atom and from 0 to 2 additional heteroatoms selected from the group consisting of N, O and S;

the subscript m is 1 or 2; and the subscript n is 0, 1 or 2.

2. The compound of claim 1 wherein

represents a benzene ring.

3. The compound of claim 1 wherein $R^3$ is hydrogen or =O.

4. The compound of claim 1 wherein

represents a benzene ring, R" is hydrogen and $R^3$ is hydrogen.

5. A compound having the formula (II):

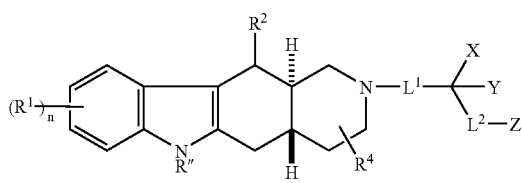

II or a pharmaceutically acceptable salt, thereof, wherein $L^1$ is a bond, ($C_1$-$C_4$)alkylene, ($C_1$-$C_4$)alkylenoxy or ($C_1$-$C_4$)alkylenamino;

$L^2$ is a bond, ($C_1$-$C_4$)alkylene, ($C_2$-$C_4$)alkenylene, ($C_2$-$C_4$)alkynylene, ($C_1$-$C_4$)alkylenoxy or ($C_1$-$C_4$)alkylenamino;

R" is hydrogen or ($C_1$-$C_8$)alkyl;

each $R^1$ is independently selected from the group consisting of halogen, ($C_1$-$C_8$)alkyl, ($C_2$-$C_8$)alkenyl, ($C_2$-$C_8$)alkynyl, fluoro($C_1$-$C_4$)alkyl, —$OR^5$, —$SR^5$, fluoro($C_1$-$C_4$)alkoxy, aryl, aryl($C_1$-$C_4$)alkyl, —$NO_2$, —$NR^5R^6$, —$C(O)R^5$, —$CO_2R^5$, —$C(O)NR^5R^6$, —$N(R^6)C(O)R^5$, —$N(R^6)CO_2R^5$, —$N(R^7)C(O)NR^5R^6$, —$S(O)_mNR^5R^6$, —$S(O)_mR^5$, —CN and —$N(R^6)S(O)_mR^5$;

$R^2$ is selected from the group consisting of hydrogen, halogen, ($C_1$-$C_8$)alkyl, ($C_2$-$C_8$)alkenyl, ($C_2$-$C_8$)alkynyl, fluoro($C_1$-$C_4$)alkyl, —$OR^8$, —$SR^8$, fluoro($C_1$-$C_4$)alkoxy, aryl, aryl($C_1$-$C_4$)alkyl, —$NO_2$, —$NR^8R^9$, =O, —$C(O)R^8$, —$CO_2R^8$, —$C(O)NR^8R^9$, —$N(R^9)C(O)R^8$, —$N(R^9)CO_2R^8$, —$N(R^{10})C(O)NR^8R^9$, —$S(O)_mNR^8R^9$, —$S(O)_mR^8$, —CN and —$N(R^9)S(O)_mR^8$;

$R^4$ is selected from the group consisting of hydrogen, —$OR^{11}$, —$C(O)R^{11}$, —$CO_2R^{11}$, —$C(O)NR^{11}R^{12}$, —CN, ($C_1$-$C_4$)alkyl and aryl;

X and Y are independently selected from the group consisting of ($C_1$-$C_8$)alkyl, ($C_2$-$C_8$)alkenyl, ($C_2$-$C_8$)alkynyl, —$CO_2R^{13}$ and —$C(O)NR^{13}R^{14}$;

optionally, X and Y may be combined to form a 3-, 4-, 5-, 6- or 7-membered ring containing from 0 to 2 heteroatoms selected from the group consisting of N, O and S;

Z is selected from the group consisting of —$OR^{15}$, —$NR^{15}R^{16}$, —$CO_2R^{15}$, —$R^{18}$, —$C(O)NR^{15}R^{16}$, —$C(O)NR^5R^{18}$, —$SO_2NR^{15}R^{16}$, —$SO_2NR^{15}R^{18}$, —$NR^{16}SO_2R^{15}$, —$N(R^{15})N(R^{16})SO_2R^{17}$, —$C(O)N(R^{16})OR^{15}$, fluoro($C_1$-$C_4$)alkyl, heteroaryl, —$C(=NOR^{15})NR^{16}R^{17}$, —$C(R^{16})=NOR^{15}$, —$NR^{16}(OR^{15})$, —$C(O)NR^{17}C(O)NR^{15}R^{16}$, —$NR^{17}C(O)NR^{16}C(O)R^{15}$ and —$NR^{17}C(O)NR^{15}R^{16}$;

$R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are independently selected from the group consisting of hydrogen, ($C_1$-$C_8$)alkyl, ($C_2$-$C_8$)alkenyl, ($C_2$-$C_8$)alkynyl, fluoro($C_1$-$C_4$)alkyl, hetero($C_1$-$C_4$)alkyl, aryl and aryl($C_1$-$C_4$)alkyl;

$R^{18}$ is a 5- or 6-membered ring containing from 1 to 3 heteroatoms selected from the group consisting of N, O and S;

optionally, when two variables selected from the group of variables consisting of $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are attached to the same nitrogen atom, the two groups may be combined to form a 3-, 4-, 5-, 6- or 7-membered ring containing the nitrogen atom and from 0 to 2 additional heteroatoms selected from the group consisting of N, O and S;

the subscript m is 1 or 2; and the subscript n is 0, 1 or 2.

6. The compound of claim 5, wherein $R^4$ is hydrogen.

7. The compound of claim 5, wherein R" is hydrogen.

8. The compound of claim 7, wherein $R^2$ is ($C_1$-$C_4$)alkyl or aryl.

9. The compound of claim 8, wherein $R^1$ is independently selected from the group consisting of halogen, ($C_1$-$C_4$)alkyl, fluoro($C_1$-$C_4$)alkyl, —$OR^5$, fluoro($C_1$-$C_4$)alkoxy, —$CO_2R^5$, —$S(O)_mNR^5R^6$, —$S(O)_mR^5$ and —CN.

10. The compound of claim 9, wherein $R^1$ is halogen or fluoro($C_1$-$C_4$)alkyl.

11. The compound of claim 9, wherein n is 0 or 1.

12. The compound of claim 11, wherein $L^1$ is $(C_1-C_4)$ alkylene.

13. The compound of claim 12, having the formula (III):

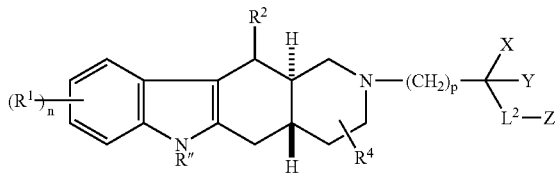

III wherein the subscript p is an integer of from 1 to 4.

14. The compound of claim 13, wherein p is 1, 2 or 3.

15. The compound of claim 14, wherein $L^2$ is a bond.

16. The compound of claim 15, wherein Z is —$CO_2R^{15}$ or —$CO_2NR^{15}R^{16}$.

17. The compound of claim 14, wherein X and Y are combined to form a 3-, 4-, 5-, 6- or 7-membered ring containing from 0 to 2 heteroatoms selected from the group consisting of O, N and S.

18. The compound of claim 17, wherein X and Y are combined to form a 5- or 6-membered ring containing from 0 to 2 heteroatoms selected from the group consisting of O, N and S.

19. The compound of claim 18, wherein X and Y are combined to form a 5- or 6-membered ring containing 0 heteroatoms, 1 nitrogen atom or 1 oxygen atom.

20. The compound of claim 5, having the formula (IV):

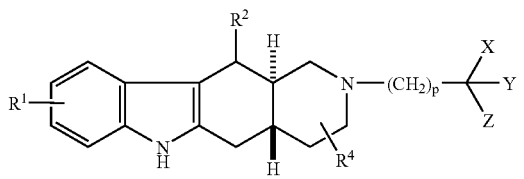

IV wherein the subscript p is an integer of from 1 to 4.

21. The compound of claim 20, wherein p is 1, 2 or 3.

22. The compound of claim 21, wherein p is 2.

23. The compound of claim 22, wherein Y is —$CO_2H$.

24. The compound of claim 22, wherein X and Y are combined to form a 3-, 4-, 5-, 6- or 7-membered ring containing from 0 to 2 heteroatoms selected from the group consisting of O, N and S.

25. The compound of claim 22, wherein X and Y are combined to form a 5- or 6-membered ring containing from 0 to 2 heteroatoms selected from the group consisting of O, N and S.

26. The compound of claim 22, wherein X and Y are combined to form a 5- or 6-membered ring containing 0 heteroatoms, 1 nitrogen atom or 1 oxygen atom.

27. The compound of claim 22, wherein X and Y are combined to form a 5- or 6-membered ring containing 0 heteroatoms, 1 nitrogen atom or 1 oxygen atom and Y is —$CO_2H$.

28. The compound of claim 22, wherein $R^2$ is methyl.

29. The compound of claim 22, wherein $R^1$ is $CF_3$.

30. The compound of claim 29, wherein $R^1$ is 9-trifluoromethyl.

31. The compound of claim 22, wherein $R^1$ is $CF_3$ and $R^2$ is methyl.

32. The compound of claim 22, wherein $R^1$ is $CF_3$, $R^2$ is methyl and Y is —$CO_2H$.

33. The compound of claim 32, wherein said compound is selected from the group consisting of:

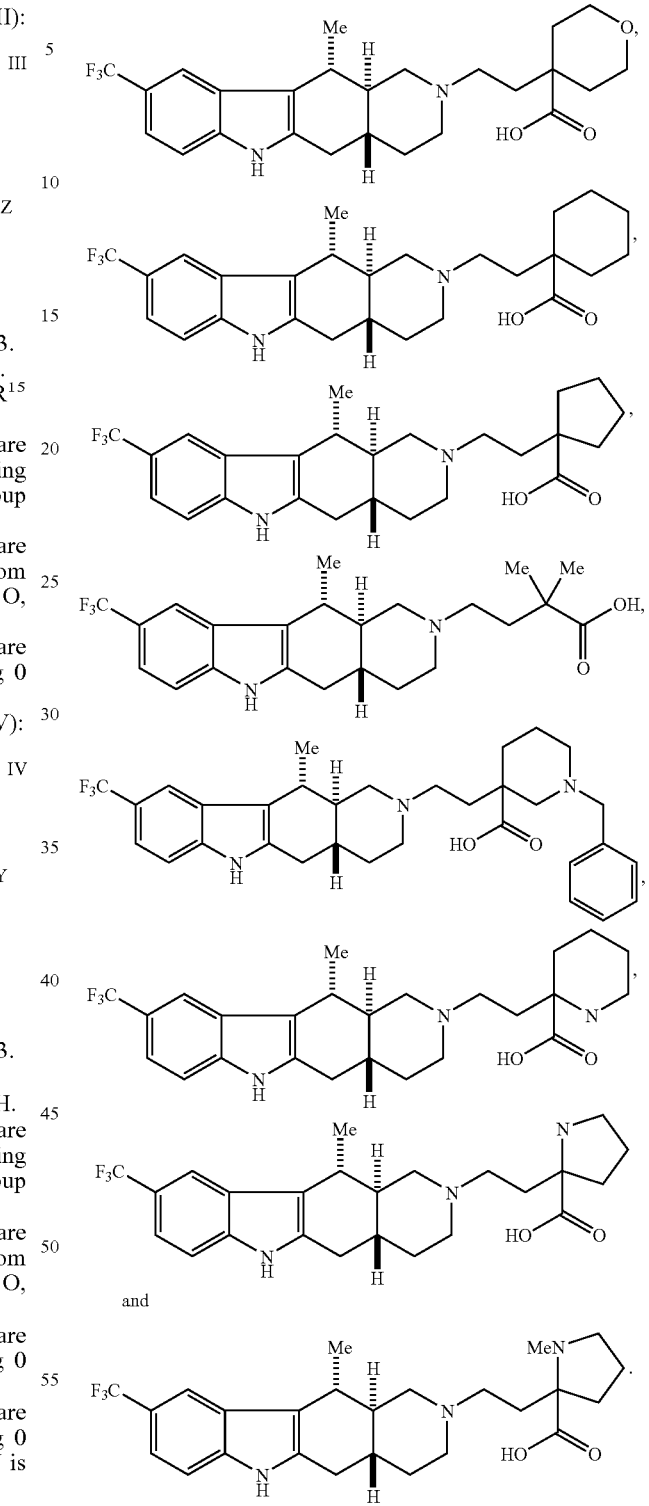

and

34. A pharmaceutical composition comprising a pharmaceutically acceptable carrier or excipient and a compound of any one of claims 1, 2 or 33.

35. The compound of claim 1, wherein $R^{18}$ is tetrazole.

* * * * *

UNITED STATES PATENT AND TRADEMARK OFFICE
CERTIFICATE OF CORRECTION

PATENT NO. : 7,253,179 B2
APPLICATION NO. : 10/705173
DATED : August 7, 2007
INVENTOR(S) : Chen et al.

It is certified that error appears in the above-identified patent and that said Letters Patent is hereby corrected as shown below:

Col. 78, Claim 1, line 20, the text reading "salt, thereof" should be --salt thereof--.

Col. 78, Claim 1, line 29, the formula should appear as follows:

--N(R)-($C_1$)alkylene--

Col. 78, Claim 1, line 42-44, the phrases "(e.g. -$OCH_2CH_2$-)" and "(e.g. -NH-$CH_2CH_2$-)" should be deleted.

Col. 80, Claim 5, line 1, the text reading "salt, thereof" should be --salt thereof--.

Col. 81, Claim 20, lines 31-41, formula IV should appear without "$R^4$" as follows:

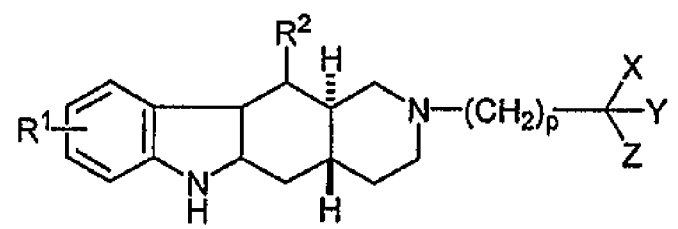

Signed and Sealed this

Fourth Day of December, 2007

JON W. DUDAS
*Director of the United States Patent and Trademark Office*